US007585996B2

(12) United States Patent
Gallop et al.

(10) Patent No.: US 7,585,996 B2
(45) Date of Patent: Sep. 8, 2009

(54) ACYLOXYALKYL CARBAMATE PRODRUGS, METHODS OF SYNTHESIS AND USE

(75) Inventors: Mark A. Gallop, Los Altos, CA (US); Feng Xu, Palo Alto, CA (US); Thu Phan, Fremont, CA (US); Usha Dilip, Sunnyvale, CA (US); Ge Peng, Mountain View, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

(21) Appl. No.: 11/901,194

(22) Filed: Sep. 13, 2007

(65) Prior Publication Data

US 2008/0146526 A1 Jun. 19, 2008

Related U.S. Application Data

(60) Provisional application No. 60/844,640, filed on Sep. 15, 2006.

(51) Int. Cl.
*C07C 271/06* (2006.01)
*A61K 31/662* (2006.01)

(52) U.S. Cl. ........................ 560/115; 514/119
(58) Field of Classification Search ................ 560/115; 514/119
See application file for complete search history.

(56) References Cited

U.S. PATENT DOCUMENTS

| 2,996,431 A | 8/1961 | Barry |
| 3,139,383 A | 6/1964 | Neville |
| 3,402,240 A | 9/1968 | Cain et al. |
| 3,803,112 A | 4/1974 | Engelhardt et al. |
| 3,811,444 A | 5/1974 | Heller et al. |
| 3,845,770 A | 11/1974 | Theeuwes et al. |
| 3,916,899 A | 11/1975 | Theeuwes et al. |
| 3,962,414 A | 6/1976 | Michaels |
| 3,992,518 A | 11/1976 | Chien et al. |
| 4,063,064 A | 12/1977 | Saunders et al. |
| 4,066,747 A | 1/1978 | Capozza |
| 4,070,347 A | 1/1978 | Schmitt |
| 4,079,038 A | 3/1978 | Choi et al. |
| 4,083,949 A | 4/1978 | Benedikt |
| 4,088,864 A | 5/1978 | Theeuwes et al. |
| 4,093,709 A | 6/1978 | Choi et al. |
| 4,126,684 A | 11/1978 | Robson et al. |
| 4,200,098 A | 4/1980 | Ayer et al. |
| 4,285,987 A | 8/1981 | Ayer et al. |
| 4,421,736 A | 12/1983 | Walters |
| 4,434,153 A | 2/1984 | Urquhart et al. |
| 4,656,298 A | 4/1987 | Dingwall et al. |
| 4,721,613 A | 1/1988 | Urquhart et al. |
| 4,752,470 A | 6/1988 | Mehta |
| 4,816,263 A | 3/1989 | Ayer et al. |
| 4,820,523 A | 4/1989 | Shtohryn et al. |
| 4,853,229 A | 8/1989 | Theeuwes |
| 4,996,058 A | 2/1991 | Sinnreich |
| 5,006,560 A | 4/1991 | Kreutner et al. |
| 5,013,863 A | 5/1991 | Baylis et al. |
| 5,051,524 A | 9/1991 | Baylis et al. |
| 5,091,184 A | 2/1992 | Khanna |
| 5,190,933 A | 3/1993 | Baylis et al. |
| 5,229,135 A | 7/1993 | Philippon et al. |
| 5,229,379 A | 7/1993 | Marescaux et al. |
| 5,281,747 A | 1/1994 | Hall et al. |
| 5,300,679 A | 4/1994 | Baylis et al. |
| 5,332,729 A | 7/1994 | Mickel et al. |
| 5,376,684 A | 12/1994 | Mickel |
| 5,407,922 A | 4/1995 | Marescaux et al. |
| 5,424,441 A | 6/1995 | Mickel et al. |
| 5,461,040 A | 10/1995 | Hall et al. |
| 5,545,631 A | 8/1996 | Marescaux et al. |
| 5,567,840 A | 10/1996 | Hall et al. |
| 5,698,155 A | 12/1997 | Grosswald et al. |
| 5,719,185 A | 2/1998 | Bountra et al. |
| 6,117,908 A | 9/2000 | Andrews et al. |

(Continued)

FOREIGN PATENT DOCUMENTS

WO   WO 00/57862 A2   10/2000

(Continued)

OTHER PUBLICATIONS

Bardgett, M. E., Boeckman, R., Krochmal, D., Fernando, H., Ahrens, R., & Csernansky, J. G. (2003). NMDA receptor blockade and hippocampal neuronal loss impair fear conditioning and position habit reversal in C57B1/6 mice. *Brain Res Bull.* 60(1-2), 131-142.

(Continued)

*Primary Examiner*—Sikarl A Witherspoon
(74) *Attorney, Agent, or Firm*—Finnegan, Henderson, Farabow, Garrett & Dunner, LLP

(57) ABSTRACT

Acyloxyalkyl carbamate prodrugs of 3-aminopropylphosphinic acid and analogs thereof, methods of making acyloxyalkyl carbamate prodrugs of 3-aminopropylphosphinic acid and analogs thereof, methods of using acyloxyalkyl carbamate prodrugs of 3-aminopropylphosphinic acid and analogs thereof, and pharmaceutical compositions comprising acyloxyalkyl carbamate prodrugs 3-aminopropylphosphinic acid and analogs thereof for treating diseases or disorders such as mild cognitive impairment, cognitive impairment associated with Alzheimer's disease Alzheimer's disease, depression, anxiety, and epilepsy are disclosed. Acyloxyalkyl carbamate prodrugs of 3-aminopropylphosphinic acid and analogs thereof, which are suitable for oral administration and sustained release oral dosage forms are also disclosed.

27 Claims, No Drawings

U.S. PATENT DOCUMENTS

| | | |
|---|---|---|
| 6,171,615 B1 | 1/2001 | Roussin et al. |
| 6,375,987 B1 | 4/2002 | Farah et al. |
| 6,379,700 B2 | 4/2002 | Joachim et al. |
| 6,627,223 B2 | 9/2003 | Percel et al. |
| 6,664,069 B1 | 12/2003 | Andrews et al. |
| 7,319,110 B2 | 1/2008 | Lange et al. |
| 2002/0187977 A1 | 12/2002 | Pearlman et al. |
| 2003/0162754 A1 | 8/2003 | Ligon |
| 2004/0152775 A1 | 8/2004 | Fitzpatrick et al. |
| 2006/0111325 A1 | 5/2006 | Gallop |
| 2006/0111439 A1 | 5/2006 | Gallop |
| 2008/0242723 A1 | 10/2008 | Gallop |

FOREIGN PATENT DOCUMENTS

| | | |
|---|---|---|
| WO | WO 01/08675 A1 | 2/2001 |
| WO | WO 01/26638 A2 | 4/2001 |
| WO | WO 01/42252 A1 | 6/2001 |
| WO | WO 01/54481 A2 | 8/2001 |
| WO | WO 02/096404 A1 | 12/2002 |
| WO | WO 02/100347 A2 | 12/2002 |
| WO | WO 02/100392 A1 | 12/2002 |
| WO | WO 02/100823 A1 | 12/2002 |
| WO | WO 02/100869 A1 | 12/2002 |
| WO | WO 02/100870 A1 | 12/2002 |
| WO | WO 02/100871 A1 | 12/2002 |
| WO | WO 03/011255 A1 | 2/2003 |
| WO | WO 2004/000855 A1 | 12/2003 |
| WO | WO 2004/000856 A1 | 12/2003 |
| WO | WO 2005/010011 A2 | 2/2005 |
| WO | WO 2005/019163 A2 | 3/2005 |
| WO | WO 2005/019163 A3 | 3/2005 |
| WO | WO 2005/066122 A2 | 7/2005 |
| WO | WO 2006/050471 A2 | 5/2006 |
| WO | WO 2006/050471 A3 | 5/2006 |
| WO | WO 2006/050472 A2 | 5/2006 |
| WO | WO 2006/050472 A3 | 5/2006 |

OTHER PUBLICATIONS

Bowery, N. (1989). $GABA_B$ receptors and their significance in mammalian pharmacology. *Trends Pharmacol Sci*, 10(10), 401-407.

Datamonitor. (2004). *Commercial and Pipeline Perspectives : Upper GI Disorders* (No. DMHC2005, pp. 147): Datamonitor.

Brown, J. S., Kalish, H. I., & Farber, I. E. (1951). Conditioned fear as revealed by magnitude of startle response to an auditory stimulus. *J Exp Psychol*, 41(5), 317-328.

Cercos-Fortea, T., Polache, A., Nacher, A., Cejudo-Ferragud, E., Casabo, V. G., & Merino, M. (1995). Influence of leucine on intestinal baclofen absorption as a model compound of neutral alpha-aminoacids. *Biopharm Drug Dispos*, 16(7), 563-577.

Conn, P. M. (Ed.). (2006). *Handbook of models for human aging*. Amsterdam ; Boston: Elsevier Academic Press.

Cryan, J. F., Markou, A., & Lucki, I. (2002). Assessing antidepressant activity in rodents: recent developments and future needs. *Trends Pharmacol Sci*, 23(5), 238-245.

Cryan, J. F., & Mombereau, C. (2004). In search of a depressed mouse: utility of models for studying depression-related behavior in genetically modified mice. *Mol Psychiatry*, 9(4), 326-357.

Czuczwar, S. J., & Patsalos, P. N. (2001). The new generation of GABA enhancers. Potential in the treatment of epilepsy. *CNS Drugs*, 15(5), 339-350.

Deguchi, Y., Inabe, K., Tomiyasu, K., Nozawa, K., Yamada, S., & Kimura, R. (1995). Study on brain interstitial fluid distribution and blood-brain barrier transport of baclofen in rats by microdialysis. *Pharm Res*, 12(12), 1838-1844.

Deprele, S., & Montchamp, J. L. (2001). Triethylborane-initiated room temperature radical addition of hypophosphites to olefins: synthesis of monosubstituted phosphinic acids and esters. *J Org Chem*, 66(20), 6745-6755.

Dingwall, J. G., Ehrenfreund, J., & Hall, R. G. (1989). Diethoxymethylphosphonites and phosphinates. Intermediates for the synthesis of alpha, beta- and gamma-aminoalkylphosphonous acids. *Tetrahedron*, 45(12), 3787-3808.

Froestl, W., Mickel, S. J., Von Sprecher, G., Diel, P. J., Hall, R. G., Maier, L., et al. (1995). Phosphinic acid analogues of GABA. 2. Selective, orally active $GABA_B$ antagonists. *J Med Chem*, 38(17), 3313-3331.

Froestl, W., Gallagher, M., Jenkins, H., Madrid, A., Melcher, T., Teichman, S., et al. (2004). SGS742: the first $GABA_B$ receptor antagonist in clinical trials. *Biochem Pharmacol*, 68(8), 1479-1487.

Getova, D., Bowery, N. G., & Spassov, V. (1997). Effects of $GABA_B$ receptor antagonists on learning and memory retention in a rat model of absence epilepsy. *Eur J Pharmacol*, 320(1), 9-13.

Gijsman, H. J., Geddes, J. R., Rendell, J. M., Nolen, W. A., & Goodwin, G. M. (2004). Antidepressants for bipolar depression: a systematic review of randomized, controlled trials. *Am J Psychiatry*, 161(9), 1537-1547.

Gleiter, C. H., Farger, G., & Mobius, H. J. (1996). Pharmacokinetics of CGP 36, 742, an orally active $GABA_B$ antagonist, in humans. *J Clin Pharmacol*, 36(5), 428-438.

Helm, K. A., Haberman, R. P., Dean, S. L., Hoyt, E. C., Melcher, T., Lund, P. K., et al. (2005). $GABA_B$ receptor antagonist SGS742 improves spatial memory and reduces protein binding to the cAMP response element (CRE) in the hippocampus. *Neuropharmacology*, 48(7), 956-964.

Higgins, G. A., & Jacobsen, H. (2003). Transgenic mouse models of Alzheimer's disease:phenotype and application. *Behavioral Phrmacology*, 14(5-6), 419-438.

Janus, C., & Westaway, D. (2001). Transgenic mouse models of Alzheimer's disease. *Physiology & Behav*, 73(5), 873-886.

Marescaux, C., Vergnes, M., & Bernasconi, R. (1992). $GABA_B$ receptor antagonists: potential new anti-absence drugs. *J Neural Transm Suppl*, 35, 179-188.

Marino, M., Peris-Ribera, J. E., Torres-Molina, F., Sanchez-Pico, A., Garcia-Carbonell, M. C., Casabo, V. G., et al. (1989). Evidence of a specialized transport mechanism for the intestinal absorption of baclofen. *Biopharm Drug Dispos*, 10(3), 279-297.

Misgeld, U., Bijak, M., & Jarolimek, W. (1995). A physiological role for $GABA_B$ receptors and the effects of baclofen in the mammalian central nervous system. *Prog in Neurobiology*, 46(4), 423-462.

Moll-Navarro, M. J., Merino, M., Casabo, V. G., Nacher, A., & Polache, A. (1996). Interaction of taurine on baclofen intestinal absorption: a nonlinear mathematical treatment using differential equations to describe kinetic inhibition models. *J Pharm Sci*, 85(11), 1248-1254.

Mondadori, C., Moebius, H. J., & Zingg, M. (1996). CGP 36, 742, an orally active $GABA_B$ receptor antagonist, facilitates memory in a social recognition test in rats. *Behav Brain Res*, 77(1-2), 227-229.

Mondadori, C., Jaekel, J., & Preiswerk, G. (1993). CGP 36742: the first orally active $GABA_B$ blocker improves the cognitive performance of mice, rats, and rhesus monkeys. *Behav & Neural Biol*, 60(1), 62-68.

Nakagawa, Y., & Takashima, T. (1997). The $GABA_B$ receptor antagonist CGP36742 attenuates the baclofen- and scopolamine-induced deficit in Morris water maze task in rats. *Brain Res*, 766(1-2), 101-106.

Nakagawa, Y., Sasaki, A., & Takashima, T. (1999). The $GABA_B$ receptor antagonist CGP36742 improves learned helplessness in rats. *Eur J Pharmacol*, 381(1), 1-7.

Porsolt, R. D., Le Pichon, M., & Jalfre, M. (1977). Depression: a new animal model sensitive to antidepressant treatments. *Nature*, 266, 730-732.

Porsolt, R. D., Bertin, A., & Jalfre, M. (1977). Behavioral despair in mice: a primary screening test for antidepressants. *Arch Int Pharmacodyn Ther*, 229(2), 327-336.

Porsolt, R. D. (2000). Animal models of depression: utility for transgenic research. *Rev Neurosci*, 11(1), 53-58.

Post, R. M., Altshuler, L. L., Frye, M. A., Suppes, T., McElroy, S. L., Keck, P. E., Jr., et al. (2005). Preliminary observations on the effectiveness of levetiracetam in the open adjunctive treatment of refractory bipolar disorder. *J Clin Psychiatry*, 66(3), 370-374.

Remington, J. P., & Beringer, P. (2005). *Remington: the science and practice of pharmacy*. Easton, Pa.: Mack Pub. Co.

Simpkins, J. W., Wen, Y., Perez, E., Yang, S., & Wang, X. (2005). Role of nonfeminizing estrogens in brain protection from cerebral ischemia: an animal model of Alzheimer's disease neuropathology. *Ann N Y Acad Sci*, 1052, 233-242.

Slattery, D. A., Desrayaud, S., & Cryan, J. F. (2005). $GABA_B$ receptor antagonist-mediated antidepressant-like behavior is serotonin-dependent. *J Pharmacol Exp Ther*, 312(1), 290-296.

Van Bree, J. B., Audus, K. L., & Borchardt, R. T. (1988). Carrier-mediated transport of baclofen across monolayers of bovine brain endothelial cells in primary culture. *Pharm Res*, 5(6), 369-371.

Van Dam, D., & De Deyn, P. P. (2006). Drug discovery in dementia: the role of rodent models. *Nat Rev Drug Discov*, 5(11), 956-970.

Verma, R. K., Mishra, B., & Garg, S. (2000). Osmotically controlled oral drug delivery. *Drug Dev Ind Pharm*, 26(7), 695-708.

Vergnes, M., Boehrer, A., Simler, S., Bernasconi, R., & Marescaux, C. (1997). Opposite effects of $GABA_B$ receptor antagonists on absences and convulsive seizures. *Eur J Pharmacol*, 332(3), 245-255.

Alderman, A review of cellulose ethers in hydrophilic matrices for oral controlled-release dosage forms, *Int. J. Pharm. Tech. & Prod. Mfr.* 1984, 5(3), 1-9).

Bamba et al., Release mechanisms in gelforming sustained release preparations, *Int. J. Pharm.* 1979, 2, 307.

Bowery, supra; "Commercial and Pipeline Perspectives: Upper GI Disorders", Data Monitor Report, Sep. 2004, p. 147.

Cange et al., Baclofen-mediated gastro-oesophageal acid reflux control in patients with established reflux disease, *Aliment. Pharmacol. Ther.* 2002, 16, 869-873.

Carruthers et al., Synthesis and resolution of β-(aminomethyl)-4-chlorobenzenethanesulfinic acid—a potent GABAB receptor ligand, *Bioorg Med Chem Lett* 1995, 5(3,) 237-40.

Carruthers et al., Synthesis of a series of sulfinic acid analogs of GABA and evaluation of their GABAB receptor affinities, *Bioorg med Chem Lett* 1998, 8, 3059-64.

Ciccaglione and Marzio, Effect of acute and chronic administration of the GABAB agonist baclofen on 24 hour pH metry and symptoms in control subjects and in patients withgastro-oesophageal reflux disease, *Gut* 2003, 52, 464-470.

Coleman et al., Polymer reviews: a practical guide to polymer miscibility, *Polymers* 1990, 31, 1187-1231.

During et al., Controlled release of dopamine from a polymeric brain implant: in vivo characterization, *Ann. Neurol.* 1989, 25, 351.

Fincher, Particle size of drugs and its relationship to adsorption and activity, *J. Pharm. Sci.* 1968, 57, 1825-1835.

Froestl et al., Phosphonic acid analogues of GABA. 1. New potentanad selective $GABA_B$ agonists, *J. Med. Chem.* 1995, 38, 3297-3312.

Goodson, in "Medical Applications of Controlled Release," supra, vol. 2, pp. 115-138 (1984).

Greene et al., "Protective Groups in Organic Chemistry," (Wiley, $2^{nd}$ ed. 1991).

Harrison and Harrison, "Compendium of Synthetic Organic Methods," vols. 1-8 (John Wiley and Sons, 1971-1996).

Howard et al., Intracerebral drug delivery in rats with lesion-induced memory deficits, *J. Neurosurg.* 1989, 71, 105-12.

Koek et al., Effect of the GABAB agonist baclofen inpatients with symptoms and duodeno-gastro-oesophageal reflux refractory to proton pump inhibitors, *Gut* 2003, 52, 1397-1402.

Langer et al., Chemical and physical structure of polymers as carriers for controlled release of bioactive agents: a review, *J Macromol. Sci. Rev. Macromol Chem.* 1983, C23(1), 61-126.

Langer, New methods of drug delivery, *Science* 1990, 249, 1527-33.

Langer and Wise (eds.), Medical Applications of Controlled Release, CRC Press., Boca Raton, Florida (1974).

Larock, "Comprehensive Organic Transformations," VCH Publishers, 1989.

Leong and Langer, Polymeric controlled drug delivery, *Adv. Drug Delivery Rev.* 1987, 1, 199-233.

Levy et al., Inhibition of calcification of bioprosthetic heart valves by local controlled-release diphosphonate, *Science* 1985, 228, 190.

Li et al., Synthesis of (alkoxycarbonyloxy)methyl, (acyloxy)methyl and (oxodioxolenyl)methyl carbamates as bioreversible prodrug moieties for amines, *Bioorganic & Medicinal Chemistry Letters* 1997, 7, 2909-12.

Lidums et al., Control of transient lower esophageal sphincter relaxations and reflux by the GABAB agonist baclofen in normal subjects, *Gastroenterology* 2000, 118, 7-13.

Lu and Yu, Dimensionless presentation for drug release from a coated pure drug bead: 2. Experiment, *Int. J. Pharm.* 1994, 112, 117-24.

Mittal et al., Transient lower esophageal sphincter relaxation, *Gastroenterology* 1995, 109, 601-10.

Moll-Navarro et al., Interaction of taurine on baclofen intestinal absorption: a nonlinear mathematical treatment using differential equations to describe kinetic inhibition models, *J. Pharm. Sci.* 1996, 85(11), 1248-54.

Paquette, "Encyclopedia of Reagents for Organic Synthesis," John Wiley & Sons, 1995.

Remington's Pharmaceutical Sciences, Lippincott Williams & Wilkins, 21st Edition, 2005.

Roerdink et al., *Horizons in Biochemistry and Biophysics Series*, Drug Carrier Systems 1989, 9, 57-10.

Roff et al., *Handbook of Common Polymers* 1971, CRC Press.

Rosoff, *Controlled Release of Drugs* Chap. 2, pp. 53-95 (1989).

Saudek et al., A preliminary trial of the programmable implantable medication system for insulin delivery, *N. Engl. J Med.* 1989, 321(9), 574-9.

Sefton, Implantable pumps, *CRC Crit Ref Biomed Engl.* 1987, 14(3), 201-39.

Shue et al., A study of 3-amino-N-hydroxypropanesulfonamide derivatives as potential GABAB agonists and their fragmentation to 3-aminopropanesulfinic acid, *Bioorg Med Chem Lett* 1996, 6(14), 1709-14.

Smolen and Ball (eds.), Controlled Drug Bioavailability, Drug Product Design and Performance, Wiley, New York (1984).

Tonini et al., Progress with novel pharmacological strategies for gastro-oesophageal reflux disease, *Drugs.* 2004, 64(4), 347-61.

Van Herwaarden et al., The effect of baclofen on gastro-oesophageal reflux, lower oesophageal sphincter function and reflux symptoms in patients with reflux disease, *Aliment. Pharmacol. Ther.* 2002, 16, 1655-62.

Vela et al., Baclofen decreases acid and non-acid post-prandial gastro-oesophageal reflux measured by combined multichannel intraluminal impedance and pH, *Aliment. Pharmacol. Ther.* 2003, 17, 243-51.

Zhang et al., Control of transient lower oesophageal sphincter relaxations and reflux by the GABAB agonist baclofen in patients with gastro-oesophageal reflux disease, *Gut* 2002, 50, 19-24.

Wikipedia, Spasticity, encyclopedia on line version.

International Preliminary Report on Patentability and Written Opinion of the International Searching Authority, issued May 8, 2007 for International Application No. PCT/US2005/039871, international filing date Nov. 3, 2005.

International Preliminary Report on Patentability and Written Opinion of the International Searching Authority, issued May 8, 2007 for International Application No. PCT/US2005/039872, international filing date Nov. 3, 2005.

International Search Report and Written Opinion of the International Searching Authority mailed Feb. 19, 2008 for International Application No. PCT/US2007/020210 international filing date Sep. 13, 2007.

Office Action mailed Apr. 9, 2008 in U.S. Appl. No. 11/265,203, filed Nov. 3, 2005.

Office Action mailed Jun. 6, 2007 in U.S. Appl. No. 11/265,204, filed Nov. 3, 2005.

Office Action mailed Aug. 13, 2007 in U.S. Appl. No. 11/265,204, filed Nov. 3, 2005.

Notice of Allowance mailed Feb. 7, 2008 in U.S. Appl. No. 11/265,204, filed Nov. 3, 2005.

Examiner Interview Summary mailed Jul. 9, 2008 in U.S. Appl. No. 11/265,204, filed Nov. 3, 2005.

Notice of Allowance mailed Oct. 14, 2008 in U.S. Appl. No. 11/265,203, filed Nov. 3, 2005.

ACYLOXYALKYL CARBAMATE PRODRUGS, METHODS OF SYNTHESIS AND USE

This application claims the benefit under 35 U.S.C. § 119 (e) of U.S. Provisional Application Ser. No. 60/844,640 filed Sep. 15, 2006, which is incorporated by reference herein in its entirety.

FIELD

The disclosure relates to acyloxyalkyl carbamate prodrugs of 3-aminopropylphosphinic acid and analogs thereof, methods of making acyloxyalkyl carbamate prodrugs of 3-aminopropylphosphinic acid and analogs thereof, methods of using acyloxyalkyl carbamate prodrugs of 3-aminopropylphosphinic acid and analogs thereof, and pharmaceutical compositions comprising acyloxyalkyl carbamate prodrugs of 3-aminopropylphosphinic acid and analogs thereof to treat disease. The disclosure also relates to acyloxyalkyl carbamate prodrugs of 3-aminopropylphosphinic acid and analogs thereof suitable for oral administration and sustained release dosage forms.

BACKGROUND (±)-4-Amino-3-(4-chlorophenyl)butanoic acid (baclofen), (1), is an analog of gamma-aminobutyric acid (i.e., GABA) that selectively activates $GABA_B$ receptors, resulting in neuronal hyperpolarization. $GABA_B$ receptors are located in laminae I-IV of the spinal cord, where primary sensory fibers end. These G-protein coupled receptors activate conductance by $K^+$-selective ion channels and may reduce currents mediated by $Ca^{2+}$ channels in certain neurons. Baclofen has a presynaptic inhibitory effect on the release of excitatory neurotransmitters and also acts postsynaptically to decrease motor neuron firing (see Bowery, *Trends Pharmacol. Sci.* 1989, 10, 401-407; Misgeld et al., *Prog. Neurobiol.* 1995, 46, 423-462).

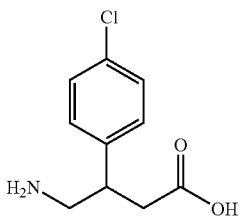

Baclofen (1)

Many examples of compounds having antagonistic activity at $GABA_B$ receptors exist and block the effects of baclofen in vitro and in vivo. Examples of $GABA_B$ antagonists include certain aminophosphonic acids (e.g. phaclofen), aminosulfonic acids (e.g. saclofen and 2-hydroxysaclofen), and aminophosphinic acids, particularly certain 3-aminopropylphosphinic acids.

Certain 3-aminopropylphosphinic acid analog $GABA_B$ antagonists are described in Froestl et al., *J. Med. Chem.* 1995, 38, 3313-3331; Dingwall et al., *Tetrahedron* 1989, 45, 3787-3808; Deprele and Montchamp, *J. Org. Chem.* 2001, 66, 6745-6755; Dingwall et al., U.S. Pat. No. 4,656,298; Baylis et al., U.S. Pat. No. 5,013,863; Baylis et al., U.S. Pat. No. 5,051,524; Baylis et al., U.S. Pat. No. 5,300,679; Marescaux et al., U.S. Pat. No. 5,229,379; Marescaux et al., U.S. Pat. No. 5,407,922; Mickel et al., U.S. Pat. No. 5,332,729; Mickel, U.S. Pat. No. 5,376,684; and Mickel et al., U.S. Pat. No. 5,424,441. Examples of aminopropylphosphinic analog $GABA_B$ antagonists include:

3-Aminopropyl(n-butyl)phosphinic acid;
3-Aminopropyl(diethoxymethyl)phosphinic acid;
3-Aminopropyl(benzyl)phosphinic acid;
3-Amino-2(S)-hydroxypropyl(benzyl)phosphinic acid;
3-Amino-2-hydroxypropyl(cyclohexylmethyl)phosphinic acid;
3-Amino-2(S)-hydroxypropyl(cyclohexylmethyl)phosphinic acid;
3-(4-Chlorobenzylamino)-2(R)-hydroxypropyl(benzyl)phosphinic acid;
3-(4-Chlorobenzylamino)propyl(diethoxymethyl)phosphinic acid;
3-(4-Chlorobenzylamino)-2-hydroxypropyl(n-butyl)phosphinic acid;
3-(3,4-Dichlorobenzylamino)-2(S)-hydroxypropyl(benzyl)phosphinic acid;
3-(3,4-Dichlorobenzylamino)-2(S)-hydroxypropyl(diethoxymethyl)phosphinic acid;
3-(4-Chlorobenzylamino)propyl(cyclohexylmethyl)phosphinic acid;
3-{N-[1-(3,4-Dichlorophenyl)ethyl]amino}-2-hydroxy-propyl-(cyclohexylmethyl)-phosphinic acid;
3-{N-[1-(3,4-Dichlorophenyl)ethyl]amino}-2(S)-hydroxy-propyl-(cyclohexylmethyl)-phosphinic acid;
3-{N-[1-(3,4-Dichlorophenyl)ethyl]amino}-2(R)-hydroxy-propyl-(cyclohexylmethyl)-phosphinic acid;
3-{N-[1(R)-(3,4-Dichlorophenyl)ethyl]amino}-2(S)-hydroxy-propyl-(cyclohexylmethyl)-phosphinic acid;
3-{N-[1(S)-(3,4-Dichlorophenyl)ethyl]amino}-2(S)-hydroxy-propyl-(cyclohexylmethyl)-phosphinic acid;
3-{N-[1(R)-(3,4-Dichlorophenyl)ethyl]amino}-2(R)-hydroxy-propyl-(cyclohexylmethyl)-phosphinic acid;
3-{N-[1(S)-(3,4-Dichlorophenyl)ethyl]amino}-2(R)-hydroxy-propyl-(cyclohexylmethyl)-phosphinic acid;
3-{N-[1-(3,4-Dichlorophenyl)ethyl]amino}-2-hydroxy-propyl-(benzyl)-phosphinic acid;
3-{N-[1-(3,4-Dichlorophenyl)ethyl]amino}-2(S)-hydroxy-propyl-(benzyl)-phosphinic acid;
3-{N-[1-(3,4-Dichlorophenyl)ethyl]amino}-2(R)-hydroxy-propyl-(benzyl)-phosphinic acid;
3-{N-[1(R)-(3,4-Dichlorophenyl)ethyl]amino}-2(S)-hydroxy-propyl-(benzyl)-phosphinic acid;
3-{N-[1(S)-(3,4-Dichlorophenyl)ethyl]amino}-2(S)-hydroxy-propyl-(benzyl)-phosphinic acid;
3-{N-[1(R)-(3,4-Dichlorophenyl)ethyl]amino}-2(R)-hydroxy-propyl-(benzyl)-phosphinic acid;
3-{N-[1(S)-(3,4-Dichlorophenyl)ethyl]amino}-2(R)-hydroxy-propyl-(benzyl)-phosphinic acid;
3-{N-[1-(3-Carboxyphenyl)ethyl]amino}-2-hydroxy-propyl-(cyclohexylmethyl)-phosphinic acid;
3-{N-[1-(3-Carboxyphenyl)ethyl]amino}-2(S)-hydroxy-propyl-(cyclohexylmethyl)-phosphinic acid;
3-{N-[1-(3-Carboxyphenyl)ethyl]amino}-2(R)-hydroxy-propyl-(cyclohexylmethyl)-phosphinic acid;
3-{N-[1(R)-(3-Carboxyphenyl)ethyl]amino}-2(S)-hydroxy-propyl-(cyclohexylmethyl)-phosphinic acid;
3-{N-[1(S)-(3-Carboxyphenyl)ethyl]amino}-2(S)-hydroxy-propyl-(cyclohexylmethyl)-phosphinic acid;
3-{N-[1(R)-(3-Carboxyphenyl)ethyl]amino}-2(R)-hydroxy-propyl-(cyclohexylmethyl)-phosphinic acid;
3-{N-[1(S)-(3-carboxyphenyl)ethyl]amino}-2(R)-hydroxy-propyl-(cyclohexylmethyl)-phosphinic acid;
3-{N-[1-(3-Carboxyphenyl)ethyl]amino}-2-hydroxy-propyl-(benzyl)-phosphinic acid;

3-{N-[1-(3-Carboxyphenyl)ethyl]amino}-2(S)-hydroxy-propyl-(benzyl)-phosphinic acid;
3-{N-[1-(3-Carboxyphenyl)ethyl]amino}-2(R)-hydroxy-propyl-(benzyl)-phosphinic acid;
3-{N-[1(R)-(3-Carboxyphenyl)ethyl]amino}-2(S)-hydroxy-propyl-(benzyl)-phosphinic acid;
3-{N-[1(S)-(3-Carboxyphenyl)ethyl]amino}-2(S)-hydroxy-propyl-(benzyl)-phosphinic acid;
3-{N-[1(R)-(3-Carboxyphenyl)ethyl]amino}-2(R)-hydroxy-propyl-(benzyl)-phosphinic acid;
3-{N-[1(S)-(3-Carboxyphenyl)ethyl]amino}-2(R)-hydroxy-propyl-(benzyl)-phosphinic acid;
pharmaceutically acceptable salts of any of the foregoing, and pharmaceutically acceptable solvates of any of the foregoing.

$GABA_B$ antagonists are useful in the treatment of cognitive or memory disorders including Mild Cognitive Impairment (MCI) and cognitive impairment associated with Alzheimer's disease (see e.g., Baylis et al., U.S. Pat. No. 5,190,933; Pearlman et al., U.S. Application Publication No. 2002/0187977; Froestl et al., *Biochem. Pharmacol.* 2004, 68, 1479-1487; Helm et al., *Neuropharmacol.* 2005, 48, 956-964; Mondadori et al., *Behav. Brain Res.* 1996, 77, 227-229; Mondadori et al., *Behav. Neural Biol.* 1993, 60, 62-68; and Nakagawa et al., *Brain Res.* 1997, 766, 101-106).

$GABA_B$ antagonists are also useful in the treatment of depressive moods or anxiety states (see e.g., Slattery et al., *J. Pharmacol. Exp. Ther.* 2005, 312, 290-296; and Nakagawa et al., *Eur. J. Pharmacol.* 1999, 381, 1-7).

$GABA_B$ antagonists are also useful in the treatment of epilepsy, particularly "petit-mal" type epilepsy, including spontaneous absence epilepsy and atypical absence epilepsy (see e.g., Marescaux et al., U.S. Pat. No. 5,407,922; Marescaux et al., U.S. Pat. No. 5,545,631; Czuczwar and Patsalos, *CNS Drugs*, 2001, 15, 339-350; Getova et al., *Eur. J. Pharmacol.* 1997, 320, 9-13; Vergnes et al., *Eur. J. Pharmacol.* 1997, 332, 245-255; and Marescaux et al., *J. Neural Transm.* 1992, 35, 179-188).

Typical ligands for $GABA_B$ receptors such as baclofen and the zwitterionic 3-aminopropylphosphinic acids noted above are polar molecules that lack the requisite physicochemical characteristics for effective passive permeability across cellular membranes. For baclofen, passage of the drug across the gastrointestinal (GI) tract and the blood-brain barrier (BBB) is mediated primarily by active transport processes rather than by passive diffusion. Accordingly, baclofen is a substrate for active transport mechanisms shared by neutral α-amino acids such as leucine and β-amino acids such as β-alanine and taurine (van Bree et al., *Pharm. Res.* 1988, 5, 369-371; Cercos-Fortea et al., *Biopharm. Drug. Disp.* 1995, 16, 563-577; Deguchi et al., *Pharm. Res.* 1995, 12, 1838-1844; Moll-Navarro et al., *J. Pharm. Sci.* 1996, 85, 1248-1254). 3-Aminopropylphosphinic acids are also likely to exploit related active transport mechanisms to permeate the GI mucosa following oral administration.

Another common feature shared by baclofen and 3-aminopropylphosphinic acid $GABA_B$ receptor antagonists is their rapid clearance from the systemic circulation, which leads to the necessity for frequent dosing in humans (e.g. three or four times daily) (see Bowery, supra; "Commercial and Pipeline Perspectives: Upper GI Disorders", Data Monitor Report, September 2004, p. 147; Gleiter et al., *J. Clin. Pharm.* 1996, 36, 428-438; and Froestl et al., *Biochem. Pharmacol.* 2004, 68, 1479-1487). Sustained release oral dosage formulations are a conventional solution to the problem of rapid systemic drug clearance, as is well known in the art (see e.g., "Remington's Pharmaceutical Sciences," Philadelphia College of Pharmacy and Science, 19th Edition, 1995). Osmotic delivery systems are also recognized methods for sustained drug delivery (see e.g., Verma et al., *Drug Dev. Ind. Pharm.* 2000, 26, 695-708). Successful application of these technologies depends on the drug of interest having an effective level of absorption from the large intestine (also referred to herein as the colon), where the dosage form spends a majority of its time during its passage down the gastrointestinal tract. Baclofen, and likely other zwitterionic $GABA_B$ receptor ligands, is poorly absorbed following administration into the colon in animal models (Merino et al., *Biopharm. Drug. Disp.* 1989, 10, 279-297), presumably because the transporter proteins mediating baclofen absorption in the upper region of the small intestine are not expressed in the large intestine. Development of an oral controlled release formulation for zwitterionic $GABA_B$ receptor antagonists should considerably improve the convenience, efficacy, and side effect profile of $GABA_B$ antagonist therapy. However, the rapid passage of conventional dosage forms through the proximal absorptive region of the small intestine has thus far prevented the successful application of sustained release technologies to these drugs. A number of exploratory delivery technologies that rely on either mucoadhesion or gastric retention have been suggested to achieve sustained delivery of baclofen (Sinnreich, U.S. Pat. No. 4,996,058; Khanna, U.S. Pat. No. 5,091,184; Fara et al., supra; Dudhara et al., International Publication No. WO 03/011255) though to date none of these appear to be able to achieve sustained blood levels of baclofen in human subjects. More recently, acyloxyalkyl carbamate prodrugs of baclofen and analogs thereof have been shown to provide enhanced bioavailability of baclofen following oral administration as described in co-pending application Gallop et al., International Publication No. WO 2005/019163 entitled "Acyloxyalkyl Carbamate Prodrugs, Methods, Synthesis and Use," filed Aug. 20, 2004. Thus, there is a need for new prodrugs of 3-aminopropylphosphinic acid $GABA_B$ receptor antagonists, which are well absorbed in the large intestine/colon and hence are suitable for oral sustained release formulations, thus improving the convenience, efficacy, and side effect profile of $GABA_B$ antagonist therapy.

SUMMARY

These and other needs are satisfied by the disclosure herein of acyloxyalkyl carbamate prodrugs of 3-aminopropylphosphinic acid and analogs thereof, pharmaceutical compositions of acyloxyalkyl carbamate prodrugs of 3-aminopropylphosphinic acid and analogs thereof, methods of making acyloxyalkyl carbamate prodrugs of 3-aminopropylphosphinic acid and analogs thereof, and methods of using acyloxyalkyl carbamate prodrugs of 3-aminopropylphosphinic acid and analogs thereof and/or pharmaceutical compositions thereof to treat various medical disorders.

In a first aspect, a compound of Formula (I) is provided:

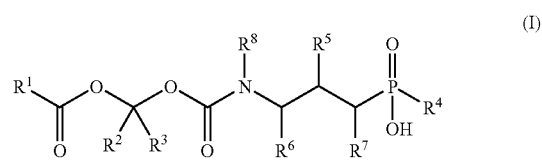

pharmaceutically acceptable salts thereof, and pharmaceutically acceptable solvates of any of the foregoing, wherein:

$R^1$ is chosen from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^2$ and $R^3$ is chosen from hydrogen, alkyl, substituted alkyl, alkoxycarbonyl, substituted alkoxycarbonyl, aryl, substituted aryl, arylalkyl, substituted arylalkyl, cycloalkyl, substituted cycloalkyl, heteroaryl, substituted heteroaryl, heteroarylalkyl, and substituted heteroarylalkyl, or $R^2$ and $R^3$ together with the carbon atom to which they are bonded form a cycloalkyl, substituted cycloalkyl, cycloheteroalkyl, or substituted cycloheteroalkyl ring;

$R^4$ is chosen from $C_{2-6}$ alkyl, substituted $C_{2-6}$ alkyl, benzyl, substituted benzyl, $C_{4-7}$ cycloalkyl, $C_{3-7}$ cycloalkylmethyl, and dialkoxymethyl;

$R^5$ is chosen from hydrogen, hydroxy, mercapto, fluoro, oxo, $C_{1-4}$ alkyl, substituted $C_{1-4}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl;

$R^6$ and $R^7$ is chosen from hydrogen, $C_{1-6}$ alkyl, $C_{1-6}$ alkoxy, aryl, substituted aryl, $C_{3-6}$ cycloalkyl, heteroaryl, substituted heteroaryl, $C_{7-9}$ phenylalkyl, and substituted $C_{7-9}$ phenylalkyl; and $R^8$ is chosen from hydrogen, $C_{1-6}$ alkyl, substituted $C_{1-6}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl.

In a second aspect, pharmaceutical compositions comprising a therapeutically effective amount of a compound of Formula (I), or a pharmaceutically acceptable salt, hydrate, or solvate thereof, and a pharmaceutically acceptable vehicle such as a diluent, carrier, excipient, or adjuvant are provided. The choice of diluent, carrier, excipient, or adjuvant will depend upon, among other factors, the desired mode of administration.

In a third aspect, methods are provided for treating cognitive or memory disorders such as mild cognitive impairment and cognitive impairment associated with Alzheimer's disease, mood disorders such as depression and anxiety, and movement disorders such as epilepsy. The methods generally involve administering to a patient in need of such treatment a therapeutically effective amount of a compound of Formula (I) and/or a pharmaceutical composition comprising a compound of Formula (I).

In a fourth aspect, a method of maintaining a therapeutically effective concentration of a 3-aminopropylphosphinic acid analog in the blood plasma of a patient for a time period chosen from at least about 4 hours, at least about 8 hours, and at least about 12 hours, comprising orally administering a pharmaceutical composition comprising the corresponding compound of Formula (I) to the patient is provided.

DETAILED DESCRIPTION

Definitions

A dash ("-") that is not between two letters or symbols is used to indicate a point of attachment for a moiety or substituent. For example, —CONH$_2$ is a moiety bonded through the carbon atom.

"1-Acyloxy-Alkyl Carbamate" refers to an N-1-acyloxyalkoxycarbonyl derivative of a 3-aminopropylphosphinic acid analog as encompassed by compounds of Formula (I) disclosed herein.

"Alkyl," by itself or as part of another substituent, refers to a saturated or unsaturated, branched or straight-chain monovalent hydrocarbon radical derived by the removal of one hydrogen atom from a single carbon atom of a parent alkane, alkene or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the expressions "alkanyl," "alkenyl," and "alkynyl" are used. In certain embodiments, alkyl groups comprise from 1 to 20 carbon atoms, in certain embodiments, from 1 to 10 carbon atoms, and in certain embodiments, from 1 to 6 carbon atoms.

"Alkanyl," by itself or as part of another substituent, refers to a saturated, branched or straight-chain alkyl radical derived by the removal of one hydrogen atom from a single carbon atom of a parent alkane. Examples of alkanyl groups include, but are not limited to, methanyl; ethanyl; propanyls such as propan-1-yl, propan-2-yl (isopropyl), etc.; butanyls such as butan-1-yl, butan-2-yl (sec-butyl), "Alkenyl," by itself or as part of another substituent, refers to an unsaturated, branched or straight-chain alkyl radical having at least one carbon-carbon double bond derived by the removal of one hydrogen atom from a single carbon atom of a parent alkene. The group may be in either the cis or trans conformation about each double bond. Examples of alkenyl groups include, but are not limited to, ethenyl; propenyls such as prop-1-en-1-yl, prop-1-en-2-yl, prop-2-en-1-yl (allyl), prop-2-en-2-yl, butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, etc.; and the like.

"Alkynyl," by itself or as part of another substituent, refers to an unsaturated, branched or straight-chain alkyl radical having at least one carbon-carbon triple bond derived by the removal of one hydrogen atom from a single carbon atom of a parent alkyne. Examples of alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to the radical —C(O)R$^{30}$, where R$^{30}$ is chosen from hydrogen, alkyl, cycloalkyl, cycloheteroalkyl, aryl, arylalkyl, heteroalkyl, heteroaryl, and heteroarylalkyl as defined herein. Examples of acyl groups include, but are not limited to, formyl, acetyl, cyclohexylcarbonyl, cyclohexylmethylcarbonyl, benzoyl, benzylcarbonyl, and the like.

"Alkoxy," by itself or as part of another substituent, refers to the radical —OR$^{31}$ where R$^{31}$ represents an alkyl or cycloalkyl group as defined herein. Examples of alkoxy groups include, but are not limited to, methoxy, ethoxy, propoxy, butoxy, cyclohexyloxy, and the like.

"Alkoxycarbonyl," by itself or as part of another substituent, refers to the radical —C(O)OR$^{32}$ where R$^{32}$ represents an alkyl or cycloalkyl group as defined herein. Examples of alkoxycarbonyl groups include, but are not limited to, methoxycarbonyl, ethoxycarbonyl, propoxycarbonyl, butoxycarbonyl, cyclohexyloxycarbonyl, and the like.

"Alkylamino," by itself or as part of another substituent, refers to the radical —NHR$^{31}$ where R$^{31}$ is chosen from alkyl and cycloalkyl, as defined herein.

"3-Aminopropylphosphinic acid analog" refers to a compound of Formula (II):

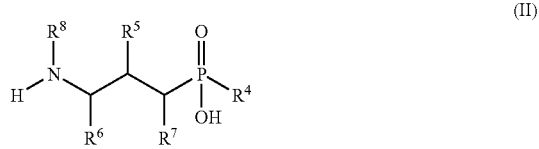

wherein R$^4$ is chosen from C$_{2-6}$ alkyl, substituted C$_{2-6}$ alkyl, benzyl, substituted benzyl, C$_{4-7}$ cycloalkyl, C$_{3-7}$ cycloalkylmethyl, and dialkoxymethyl;

R$^5$ is chosen from hydrogen, hydroxy, mercapto, fluoro, oxo, C$_{1-4}$ alkyl, substituted C$_{1-4}$ alkyl, aryl, substituted aryl, C$_{3-6}$ cycloalkyl, substituted C$_{3-6}$ cycloalkyl, heteroaryl, substituted heteroaryl, C$_{7-9}$ phenylalkyl, and substituted C$_{7-9}$ phenylalkyl;

R$^6$ and R$^7$ is chosen from hydrogen, C$_{1-6}$ alkyl, C$_{1-6}$ alkoxy, aryl, substituted aryl, C$_{3-6}$ cycloalkyl, heteroaryl, substituted heteroaryl, C$_{7-9}$ phenylalkyl, and substituted C$_{7-9}$ phenylalkyl; and R$^8$ is chosen from hydrogen, C$_{1-6}$ alkyl, substituted C$_{1-6}$ alkyl, aryl, substituted aryl, C$_{3-6}$ cycloalkyl, substituted C$_{3-6}$ cycloalkyl, heteroaryl, substituted heteroaryl, C$_{7-9}$ phenylalkyl, and substituted C$_{7-9}$ phenylalkyl.

In certain embodiments of compounds of Formula (II), each of the one or more substituent groups is independently chosen from halogen, C$_{1-3}$ alkyl, —OH, —NH$_2$, —SH, —COOH, C$_{1-3}$ alkoxy, C$_{1-3}$ acyl, C$_{1-3}$ thioalkyl, C$_{1-3}$ alkoxycarbonyl, C$_{1-3}$ alkylamino, and C$_{1-3}$ dialkylamino.

Within the scope of this disclosure, it is to be understood that when R$^5$ is an oxo group the bond between R$^5$ and the carbon to which it is bonded is a double bond.

"Aryl," by itself or as part of another substituent, refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocylic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, aryl groups have from 5 to 20 carbon atoms, and in certain embodiments, from 5 to 12 carbon atoms. In certain embodiments, aryl has from 6 to 10 carbon atoms.

"Arylalkyl," by itself or as part of another substituent, refers to an acyclic alkyl radical in which one of the hydrogen atoms bonded to a carbon atom, typically a terminal or sp$^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, and/or arylalkynyl is used. In certain embodiments, an arylalkyl group is (C$_7$-C$_{30}$) arylalkyl, e.g., the alkanyl, alkenyl or alkynyl moiety of the arylalkyl group is (C$_1$-C$_{10}$) and the aryl moiety is (C$_6$-C$_{20}$), and in certain embodiments, an arylalkyl group is (C$_7$-C$_{20}$) arylalkyl, e.g., the alkanyl, alkenyl, or alkynyl moiety of the arylalkyl group is (C$_1$-C$_8$) and the aryl moiety is (C$_6$-C$_2$).

"AUC" is the area under a curve representing the concentration of a compound or metabolite thereof in a biological fluid in a patient as a function of time following administration of the compound to the patient. In certain embodiments, the compound is a prodrug and the metabolite is a drug. Examples of biological fluids include plasma and blood. The AUC may be determined by measuring the concentration of a compound or metabolite thereof in a biological fluid such as the plasma or blood using methods such as liquid chromatography-tandem mass spectrometry (LC/MS/MS), at various time intervals, and calculating the area under the plasma concentration-versus-time curve. Suitable methods for calculating the AUC from a drug concentration-versus-time curve are well known in the art. For example, an AUC for an α-amino acid may be determined by measuring the concentration of the α-amino acid in the plasma or blood of a patient following administration of a compound of Formula (I) to the patient.

"C$_{max}$" is the maximum concentration of a drug in the plasma or blood of a patient following administration of a dose of the drug or prodrug to the patient.

"Compounds" of Formula (I) disclosed herein include any specific compounds within the formula whose structure is disclosed herein. Compounds may be identified by their chemical structure and/or chemical name. If the chemical structure and chemical name conflict, the chemical structure is determinative of the identity of the compound.

The compounds described herein may comprise one or more chiral centers and/or double bonds and therefore may exist as stereoisomers such as double-bond isomers (i.e., geometric isomers), enantiomers, and diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques and stereoisomerically pure forms may be synthesized using chiral synthesis techniques well known to the skilled artisan.

Compounds of Formula (I) include, but are not limited to, optical isomers of compounds of Formula (I), racemates thereof, and other mixtures thereof. In such embodiments, the single enantiomers or diastereomers, i.e., optically active forms may be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column. In addition, compounds of Formula (I) include Z- and E-forms (or cis- and trans-forms) of compounds with double bonds. In embodiments in which compounds of Formula (I) exist in various tautomeric forms, compounds of Formula (I) include any and all tautomeric forms of the compound.

The compounds of Formula (I) may also exist in several tautomeric forms including the enol form, the keto form, and mixtures thereof. Accordingly, the chemical structures depicted herein encompass any and all possible tautomeric forms of the illustrated compounds. The compounds of Formula (I) also include isotopically labeled compounds where one or more atoms have an atomic mass different from the atomic mass conventionally found in nature. Examples of isotopes that may be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrates, solvates, or N-oxides. Certain compounds may exist in multiple crystalline or amorphous forms. Compounds of Formula (I) include pharmaceutically acceptable salts thereof, pharmaceutically acceptable solvates of the free acid form of any of the foregoing, as well as crystalline forms of any of the foregoing.

In general, all physical forms are equivalent for the uses contemplated herein and are intended to be within the scope of the present disclosure. Further, it should be understood, when partial structures of the compounds are illustrated, that an asterisk indicates the point of attachment of the partial structure to the rest of the molecule.

"Corresponding 3-aminopropylphosphinic acid analog" refers to a compound of Formula (II) having the same $R^4$, $R^5$, $R^6$, $R^7$, and $R^8$ groups as the acyloxyalkyl carbamate prodrug of the 3-aminopropylphosphinic acid analog of Formula (I). The "corresponding acyloxyalkyl carbamate prodrug" refers to the compound of Formula (I) having the same $R^4$, $R^5$, $R^6$, $R^7$, and $R^8$ groups as the 3-aminopropylphosphinic acid analog of Formula (II)

"Cycloalkoxycarbonyl," by itself or as part of another substituent, refers to the radical —C(O)OR$^{36}$ where R$^{36}$ represents an cycloalkyl group as defined herein. Examples of cycloalkoxycarbonyl groups include, but are not limited to, cyclobutyloxycarbonyl, cyclohexyloxycarbonyl, and the like.

"Cycloalkyl," by itself or as part of another substituent, refers to a saturated or partially unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, the cycloalkyl group is $C_{3-10}$ cycloalkyl, and in certain embodiments $C_{3-7}$ cycloalkyl.

"Cycloheteroalkyl," by itself or as part of another substituent, refers to a saturated or partially unsaturated cyclic alkyl radical in which one or more carbon atoms (and any associated hydrogen atoms) is replaced with the same or different heteroatom. Examples heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Examples of cycloheteroalkyl groups include, but are not limited to, groups derived from epoxides, azirines, thiiranes, imidazolidine, morpholine, piperazine, piperidine, pyrazolidine, pyrrolidine, quinuclidine, and the like.

"Dialkylamino" by itself or as part of another substituent refers to the radical —NR$^{43}$R$^{44}$ where R$^{43}$ and R$^{44}$ are independently chosen from alkyl, cycloalkyl, cycloheteroalkyl, arylalkyl, heteroalkyl, and heteroarylalkyl, or R$^{43}$ and R$^{44}$ together with the nitrogen to which they are bonded form a cycloheteroalkyl ring.

"Halogen" refers to a fluoro, chloro, bromo, or iodo group.

"Heteroalkyl, heteroalkanyl, heteroalkenyl, and heteroalkynyl," by themselves or as part of another substituent, refer to alkyl, alkanyl, alkenyl, and alkynyl groups, respectively, in which one or more of the carbon atoms (and any associated hydrogen atoms) is replaced with the same or different heteroatomic groups. Typical heteroatomic groups which may be included in these groups include, but are not limited to, —O—, —S—, —O—O—, —S—S—, —O—S—, —NR$^{37}$R$^{38}$—, =N—N=, —N=N—, —N=N—NR$^{39}$R$^{40}$, —PR$^{41}$—, —P(O)$_2$—, —POR$^{42}$—, —O—P(O)$_2$—, —SO—, —SO$_2$—, —SnR$^{43}$R$^{44}$— and the like, where R$^{37}$, R$^{38}$, R$^{39}$, R$^{40}$, R$^{41}$R$^{42}$, and R$^{44}$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, or substituted heteroarylalkyl.

"Heteroaryl," by itself or as part of another substituent, refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which may be aromatic or non-aromatic. Heteroaryl encompasses 5- to 7-membered aromatic, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is a 5- to 20-membered heteroaryl, and in certain embodiments a 5- to 10-membered heteroaryl.

In certain embodiments, heteroaryl groups are those derived from thiophene, pyrrole, benzothiophene, benzofuran, indole, pyridine, quinoline, imidazole, oxazole, and pyrazine.

"Heteroarylalkyl," by itself or as part of another substituent, refers to an acyclic alkyl radical in which one of the hydrogen atoms bonded to a carbon atom, typically a terminal or $Sp^3$ carbon atom, is replaced with a heteroaryl group. Where specific alkyl moieties are intended, the nomenclature heteroarylalkanyl, heteroarylalkenyl, and heterorylalkynyl is used. In certain embodiments, the heteroarylalkyl group is a 6-30 membered heteroarylalkyl, e.g., the alkanyl, alkenyl, or alkynyl moiety of the heteroarylalkyl is 1-10 membered and the heteroaryl moiety is a 5-20-membered heteroaryl, and in certain embodiments, 6-20 membered heteroarylalkyl, e.g., the alkanyl, alkenyl, or alkynyl moiety of the heteroarylalkyl is 1-8 membered and the heteroaryl moiety is a 5-12-membered heteroaryl.

"Parent Aromatic Ring System" refers to an unsaturated cyclic or polycyclic ring system having a conjugated $\pi$ (pi) electron system. Specifically included within the definition of "parent aromatic ring system" are fused ring systems in which one or more of the rings are aromatic and one or more of the rings are saturated or unsaturated, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent Heteroaromatic Ring System" refers to a parent aromatic ring system in which one or more carbon atoms (and any associated hydrogen atoms) is replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Patient" includes mammals, such as for example, humans.

"Pharmaceutical composition" refers to at least one compound of Formula (I) and at least one pharmaceutically acceptable vehicle with which the compound is to be administered to a patient.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and (2) salts formed when an acidic proton present in the parent compound is replaced by a metal ion, e.g., an alkali metal ion, an alkaline earth metal ion, or an aluminum ion; or coordinates with an organic base such as ethanolamine, diethanolamine, triethanolamine, N-methylglucamine, and the like.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which the compound of Formula (I) may be administered to a patient and which does not destroy the pharmacological activity thereof, and which is nontoxic when administered in doses sufficient to provide a therapeutically effective amount of the compound.

"Pharmaceutically acceptable" refers to approved or approvable by a regulatory agency of a federal or a state government, listed in the U.S. Pharmacopoeia, or listed other generally recognized pharmacopoeia for use in mammals, including humans.

"Prodrug" refers to a derivative of an active compound (drug) that undergoes a transformation under the conditions of use, such as within the body, to release an active drug. Prodrugs are frequently, but not necessarily, pharmacologically inactive until converted into the active drug. Prodrugs may be obtained by bonding a promoiety (defined herein), typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach, or the agent may be supplied exogenously. In certain embodiments, the drug is 3-aminopropylphosphinic acid or analog thereof of Formula (II) and the promoiety is an acyloxyalkyloxycarbonyl group having the structure:

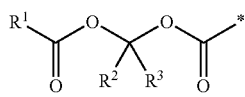

where $R^1$, $R^2$, and $R^3$ are defined herein.

"Protecting group" refers to a group of atoms, which when attached to a reactive functional group in a molecule, masks, reduces, or prevents reactivity of the functional group. Examples of protecting groups can be found in Green et al., "Protective Groups in Organic Chemistry," (Wiley, $2^{nd}$ ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers, and allyl ethers.

"Pharmaceutically acceptable solvate" refers to a molecular complex of a compound with one or more solvent molecules in a stoichiometric or non-stoichiometric amount. Such solvent molecules are those commonly used in the pharmaceutical arts, e.g., water, ethanol, and the like. A molecular complex of a compound or moiety of a compound and a solvent can be stabilized by non-covalent intra-molecular forces such as, electrostatic forces, van der Waals forces, and hydrogen bonds. The term "hydrate" refers to a complex in which the one or more solvent molecules are water including monohydrates and hemi-hydrates.

"Substantially one diastereomer" refers to a compound containing 2 or more stereogenic centers such that the diastereomeric excess (d.e.) of the compound is greater than or equal to 90%. In some embodiments, the d.e. is, for example, greater than or equal to 91%, 92%, 93%, 94%, 95%, 96%, 97%, 98%, and 99%.

"Substituted" refers to a group in which one or more hydrogen atoms are independently replaced with the same or different substituent(s). Examples of substituents include, but are not limited to, —X, —$R^{60}$, —$O^-$, =O, —$OR^{60}$, —$SR^{60}$, —$S^-$, =S, —$NR^{60}R^{61}$, =$NR^{60}$, —$CX_3$, —CN, —$CF_3$, —OCN, —SCN, —NO, —$NO_2$, =$N_2$, —$N_3$, —$S(O)_2O^-$, —$S(O)_2OH$, —$S(O)_2R^{60}$, —$OS(O_2)O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —(S)$OR^{60}$, —$NR^{62}C(O)NR^{60}R^{61}$, —$NR^{62}C(S)NR^{60}R^{61}$, —$NR^{62}C(NR^{63})NR^{60}R^{61}$, —$C(NR^{62})NR^{60}OR^{61}$, —$S(O)_2$, $NR^{60}R^{61}$, —$NR^{63}S(O)_2R^{60}$, —$NR^{63}C(O)R^{10}$, and —$S(O)R^{60}$ where each X is independently a halogen; each $R^{60}$ and $R^{61}$ are independently chosen from hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl, substituted heteroaryl, arylalkyl, substituted arylalkyl, heteroarylalkyl, and substituted heteroarylalkyl, or $R^{60}$ and $R^{61}$, together with the nitrogen atom to which they are bonded, form a cycloheteroalkyl, substituted cycloheteroalkyl, heteroaryl, or substituted heteroaryl ring; and each $R^{62}$ and $R^{63}$ are independently chosen from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, and substituted heteroarylalkyl, or $R^{62}$ and $R^{63}$, together with the atom to which they are bonded, form one or more cycloheteroalkyl, substituted cycloheteroalkyl, heteroaryl, or substituted heteroaryl rings. In certain embodiments, a tertiary amine or aromatic nitrogen may be substituted with one or more oxygen atoms to form the corresponding nitrogen oxide.

In certain embodiments of the compounds of Formula (I) and Formula (II), each of the one or more substituent groups is independently chosen from halogen, $C_{1-3}$ alkyl, —OH, —$NH_2$, —SH, —COOH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

"Thioalkyl," by itself or as part of another substituent, refers to the radical —$SR^{41}$ where $R^{41}$ is alkyl as defined herein. "Mercapto," by itself or as part of another substituent, refers to the radical —$SR^{41}$ where $R^{41}$ is hydrogen.

"Treating" or "treatment" of a disease refers to arresting or ameliorating a disease, disorder, or at least one of the clinical symptoms of a disease or disorder. In certain embodiments, "treating" or "treatment" refers to arresting or ameliorating at least one physical parameter of the disease or disorder, which may or may not be discernible by the patient. In certain embodiments, "treating" or "treatment" refers to inhibiting or controlling the disease or disorder, either physically (e.g., stabilization of a discernible symptom), physiologically (e.g., stabilization of a physical parameter), or both. In certain embodiments, "treating" or "treatment" refers to delaying, in some cases indefinitely, the onset of a disease or disorder.

"Therapeutically effective amount" refers to the amount of a compound that, when administered to a subject for treating a disease, or disorder, or at least one of the clinical symptoms of a disease or disorder, is sufficient to affect such treatment of the disease, disorder, or symptom. The "therapeutically effective amount" may vary depending, for example, on the compound, the disease, disorder, and/or symptoms of the disease, severity of the disease, disorder, and/or symptoms of the disease, the age, weight, and/or health of the patient to be treated, and the judgment of the prescribing physician. An appropriate amount in any given instance may be readily ascertained by those skilled in the art or capable of determination by routine experimentation.

Reference is now be made in detail to certain embodiments of compounds and methods of the present disclosure. The disclosed embodiments are not intended to be limiting of the claims. To the contrary, the claims are intended to cover all alternatives, modifications, and equivalents.

Compounds

In a first aspect, compounds of Formula (I) are provided:

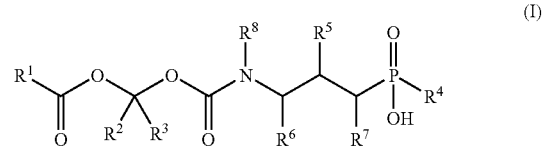

and pharmaceutically acceptable salts of any of the foregoing, and pharmaceutically acceptable solvates of any of the foregoing, wherein:

$R^1$ is chosen from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^2$ and $R^3$ is chosen from hydrogen, alkyl, substituted alkyl, alkoxycarbonyl, substituted alkoxycarbonyl, aryl, substituted aryl, arylalkyl, substituted arylalkyl, cycloalkyl, substituted cycloalkyl, heteroaryl, substituted heteroaryl, heteroarylalkyl, and substituted heteroarylalkyl, or $R^2$ and $R^3$ together with the carbon atom to which they are bonded form a cycloalkyl, substituted cycloalkyl, cycloheteroalkyl, or substituted cycloheteroalkyl ring;

$R^4$ is chosen from $C_{2-6}$ alkyl, substituted $C_{2-6}$ alkyl, benzyl, substituted benzyl, $C_{4-7}$ cycloalkyl, $C_{3-7}$ cycloalkylmethyl, and dialkoxymethyl;

$R^5$ is chosen from hydrogen, hydroxy, mercapto, fluoro, oxo, $C_{1-4}$ alkyl, substituted $C_{1-4}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl;

$R^6$ and $R^7$ is chosen from hydrogen, $C_{1-6}$ alkyl, $C_{1-6}$ alkoxy, aryl, substituted aryl, $C_{3-6}$ cycloalkyl, heteroaryl, substituted heteroaryl, $C_{7-9}$ phenylalkyl, and substituted $C_{7-9}$ phenylalkyl; and $R^8$ is chosen from hydrogen, $C_{1-6}$ alkyl, substituted $C_{1-6}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl.

In certain embodiments of compounds of Formula (I), each of the one or more substituent groups is independently chosen from halogen, $C_{1-3}$ alkyl, —OH, —NH$_2$, —SH, —COOH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

Within the scope of this disclosure, it is to be understood that when $R^5$ is an oxo group the bond between $R^5$ and the carbon to which it is bonded is a double bond.

In certain embodiments, each of $R^6$, $R^7$ and $R^8$ is hydrogen.

In certain embodiments, $R^4$ is chosen from ethyl, n-propyl, isopropyl, n-butyl, isobutyl, sec-butyl, tert-butyl, n-pentyl, isopentyl, sec-pentyl, neopentyl, n-hexyl, n-heptyl, allyl, 2-methylallyl, but-3-enyl, propargyl, but-2-ynyl, but-3-ynyl, pent-3-ynyl, cyclohexyl, cyclopropylmethyl, cyclobutylmethyl, cyclopentylmethyl, cyclohexylmethyl, cycloheptylmethyl, 2-methoxyethyl, 3-methoxypropyl, 3-ethoxypropyl, 1-hydroxyethyl, 1-hydroxybutyl, 1-hydroxyisobutyl, benzyl, 1-hydroxybenzyl, and diethoxymethyl.

In certain embodiments, $R^4$ is ethyl.
In certain embodiments, $R^4$ is n-propyl.
In certain embodiments, $R^4$ is n-butyl.
In certain embodiments, $R^4$ is diethoxymethyl.
In certain embodiments, $R^4$ is cyclohexylmethyl.
In certain embodiments, $R^4$ is benzyl.

In certain embodiments, $R^5$ is hydrogen, hydroxy, fluoro, oxo, or 4-chlorophenyl. In other embodiments, $R^4$ is ethyl, n-propyl, isopropyl, n-butyl, isobutyl, sec-butyl, tert-butyl, n-pentyl, isopentyl, sec-pentyl, neopentyl, n-hexyl, n-heptyl, allyl, 2-methylallyl, but-3-enyl, propargyl, but-2-ynyl, but-3-ynyl, pent-3-ynyl, cyclohexyl, cyclopropylmethyl, cyclobutylmethyl, cyclopentylmethyl, cyclohexylmethyl, cycloheptylmethyl, 2-methoxyethyl, 3-methoxypropyl, 3-ethoxypropyl, 1-hydroxyethyl, 1-hydroxybutyl, 1-hydroxyisobutyl, benzyl, 1-hydroxybenzyl, or diethoxymethyl, $R^5$ is hydrogen, hydroxy, fluoro, oxo, or 4-chlorophenyl, and each of $R^6$, $R^7$, and $R^8$ is hydrogen.

In certain embodiments of a compound of Formula (I), the carbon to which $R^5$ is bonded is of the R configuration. In other embodiments of a compound of Formula (I), the carbon to which $R^5$ is bonded is of the S configuration.

In certain embodiments of compounds of Formula (I), $R^1$ is chosen from $C_{1-6}$ alkyl, substituted $C_{1-6}$ alkyl, $C_{3-6}$ cycloalkyl, phenyl, substituted phenyl, $C_{7-9}$ phenylalkyl, and pyridyl. In other embodiments of compounds of Formula (I), $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, or 4-pyridyl. In certain embodiments of compounds of Formula (I), $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, or 3-pyridyl.

In certain embodiments of compounds of Formula (I), $R^1$ is chosen from propyl, isopropyl, tert-butyl, cyclohexyl, and phenyl.

In certain embodiments of compounds of Formula (I), $R^2$ is chosen from hydrogen, methyl, and isopropyl; and $R^3$ is hydrogen.

In certain embodiments of compounds of Formula (I), $R^3$ is hydrogen.

In certain embodiments of compounds of Formula (I), $R^4$ is n-butyl.

In certain embodiments of compounds of Formula (I), $R^5$ is chosen from hydrogen and hydroxy.

In certain embodiments of compounds of Formula (I), $R^1$ is chosen from propyl, isopropyl, tert-butyl, cyclohexyl, and phenyl; $R^2$ is chosen from hydrogen, methyl, and isopropyl; $R^4$ is n-butyl; and each of $R^3$, $R^5$, $R^6$, $R^7$, and $R^8$ is hydrogen.

In certain embodiments of compounds of Formula (I), $R^2$ and $R^3$ is chosen from hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl and substituted heteroarylalkyl. In certain embodiments of compounds of Formula (I), $R^2$ and $R^3$ is chosen from hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl, and pyridyl. In certain embodiments of compounds of Formula (I), $R^2$ and $R^3$ is chosen from hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl, and 4-pyridyl. In certain embodiments of compounds of Formula (I), $R^2$ is hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl, or 4-pyridyl, and $R^3$ is hydrogen. In certain embodiments of compounds of Formula (I), $R^2$ is hydrogen, methyl, ethyl, n-propyl, isopropyl, n-butyl, isobutyl, sec-butyl, phenyl, or cyclohexyl, and $R^3$ is hydrogen. In certain embodiments of a compound of Formula (I), $R^2$ is methyl, methoxycarbonyl, ethoxycarbonyl, isopropoxycarbonyl, or cyclohexyloxycarbonyl, and $R^3$ is methyl.

In certain embodiments of a compound of Formula (I), $R^2$ and $R^3$ together with the carbon atom to which they are bonded form a cycloalkyl, substituted cycloalkyl, cycloheteroalkyl, or substituted cycloheteroalkyl ring. In certain embodiments of compounds of Formula (I), $R^2$ and $R^3$ together with the carbon atom to which they are bonded form a cyclobutyl, cyclopentyl, or cyclohexyl ring.

In certain embodiments of a compound of Formula (I), $R^1$ is chosen from $C_{1-6}$ alkyl, substituted $C_{1-6}$ alkyl, $C_{3-6}$ cycloalkyl, phenyl, substituted phenyl, $C_{7-9}$ phenylalkyl and pyridyl, and $R^2$ and $R^3$ is chosen from hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl and pyridyl. In certain of the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, or 4-pyridyl, and in certain embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, or 3-pyridyl. In certain of the above embodiments of a compound of Formula (I), $R^4$ is ethyl, n-propyl, n-butyl, diethoxymethyl, cyclohexylmethyl, or benzyl, and $R^5$ is hydrogen, hydroxy, fluoro, oxo, or 4-chlorophenyl.

In certain embodiments of a compound of Formula (I), $R^1$ is chosen from $C_{1-6}$ alkyl, substituted $C_{1-6}$ alkyl, $C_{3-6}$ cycloalkyl, phenyl, substituted phenyl, $C_{7-9}$ phenylalkyl, and pyridyl, $R^2$ and $R^3$ is chosen from hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl, and 4-pyridyl. In certain of the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, or 4-pyridyl, and in certain embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, or 3-pyridyl. In certain of the above embodiments of a compound of Formula (I), $R^4$ is ethyl, n-propyl, isopropyl, n-butyl, isobutyl, sec-butyl, tert-butyl, n-pentyl, isopentyl, sec-pentyl, neopentyl, n-hexyl, n-heptyl, allyl, 2-methylallyl, but-3-enyl, propargyl, but-2-ynyl, but-3-ynyl, pent-3-ynyl, cyclohexyl, cyclopropylmethyl, cyclobutylmethyl, cyclopentylmethyl, cyclohexylmethyl, cycloheptylmethyl, 2-methoxyethyl, 3-methoxypropyl, 3-ethoxypropyl, 1-hydroxyethyl, 1-hydroxybutyl, 1-hydroxyisobutyl, benzyl, 1-hydroxybenzyl, or diethoxymethyl, in certain embodiments, $R^4$ is ethyl, n-propyl, n-butyl, diethoxymethyl, cyclohexylmethyl, or benzyl, $R^5$ is hydrogen, hydroxy, fluoro, oxo, or 4-chlorophenyl, and each of $R^6$, $R^7$, and $R^8$ is hydrogen.

In certain embodiments of a compound of Formula (I), $R^1$ is chosen from $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ is hydrogen, methyl, ethyl, n-propyl, isopropyl, n-butyl, isobutyl, phenyl, or cyclohexyl, and $R^3$ is hydrogen. In certain of the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, or 4-pyridyl, and in certain embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, or 3-pyridyl. In certain of the above embodiments of a compound of Formula (I), $R^4$ is ethyl, n-propyl, isopropyl, n-butyl, isobutyl, sec-butyl, tert-butyl, n-pentyl, isopentyl, sec-pentyl, neopentyl, n-hexyl, n-heptyl, allyl, 2-methylallyl, but-3-enyl, propargyl, but-2-ynyl, but-3-ynyl, pent-3-ynyl, cyclohexyl, cyclopropylmethyl, cyclobutylmethyl, cyclopentylmethyl, cyclohexylmethyl, cycloheptylmethyl, 2-methoxyethyl, 3-methoxypropyl, 3-ethoxypropyl, 1-hydroxyethyl, 1-hydroxybutyl, 1-hydroxyisobutyl, benzyl, 1-hydroxybenzyl, or diethoxymethyl, and in certain embodiments, $R^4$ is ethyl, n-propyl, n-butyl, diethoxymethyl, cyclohexylmethyl, or benzyl, $R^5$ is hydrogen, hydroxy, fluoro, oxo, or 4-chlorophenyl, and each of $R^6$, $R^7$, and $R^8$ is hydrogen.

In certain embodiments of a compound of Formula (I) $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, or 4-pyridyl, $R^2$ is hydrogen, methyl, ethyl, n-propyl, isopropyl, n-butyl, isobutyl, sec-butyl, phenyl, or cyclohexyl, $R^3$ is hydrogen, $R^4$ is ethyl, n-propyl, isopropyl, n-butyl, isobutyl, sec-butyl, tert-butyl, n-pentyl, isopentyl, sec-pentyl, neopentyl, n-hexyl, n-heptyl, allyl, 2-methylallyl, but-3-enyl, propargyl, but-2-ynyl, but-3-ynyl, pent-3-ynyl, cyclohexyl, cyclopropylmethyl, cyclobutylmethyl, cyclopentylmethyl, cyclohexylmethyl, cycloheptylmethyl, 2-methoxyethyl, 3-methoxypropyl, 3-ethoxypropyl, 1-hydroxyethyl, 1-hydroxybutyl, 1-hydroxyisobutyl, benzyl, 1-hydroxybenzyl, or diethoxymethyl, $R^5$ is hydrogen, and each of $R^6$, $R^7$, and $R^8$ is hydrogen. In certain embodiments of compounds of Formula (I), $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, or 4-pyridyl, $R^2$ is hydrogen, methyl, n-propyl, or isopropyl, $R^3$ is hydrogen, $R^4$ is ethyl, n-propyl, isopropyl, n-butyl, isobutyl, sec-butyl, tert-butyl, n-pentyl, isopentyl, sec-pentyl, neopentyl, n-hexyl, n-heptyl, allyl, 2-methylallyl, but-3-enyl, propargyl, but-2-ynyl, but-3-ynyl, pent-3-ynyl, cyclohexyl, cyclopropylmethyl, cyclobutylmethyl, cyclopentylmethyl, cyclohexylmethyl, cycloheptylmethyl, 2-methoxyethyl, 3-methoxypropyl, 3-ethoxypropyl, 1-hydroxyethyl, 1-hydroxybutyl, 1-hydroxyisobutyl, benzyl, 1-hydroxybenzyl, or diethoxymethyl, $R^5$ is hydrogen, and each of $R^6$, $R^7$, and $R^8$ is hydrogen. In certain embodiments of compounds of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, methyl, n-propyl, or isopropyl, $R^3$ is hydrogen, $R^4$ is ethyl, n-propyl, isopropyl, n-butyl, isobutyl, sec-butyl, tert-butyl, n-pentyl, isopentyl, sec-pentyl, neopentyl, n-hexyl, n-heptyl, allyl, 2-methylallyl, but-3-enyl, propargyl, but-2-ynyl, but-3-ynyl, pent-3-ynyl, cyclohexyl, cyclopropylmethyl, cyclobutylmethyl, cyclopentylmethyl, cyclohexylmethyl, cycloheptylmethyl, 2-methoxyethyl, 3-methoxypropyl, 3-ethoxypropyl, 1-hydroxyethyl, 1-hydroxybutyl, 1-hydroxyisobutyl, benzyl, 1-hydroxybenzyl, or diethoxymethyl, $R^5$ is hydrogen, and each of $R^6$, $R^7$, and $R^8$ is hydrogen. In certain embodiments of compounds of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, methyl, n-propyl, or isopropyl, $R^3$ is hydrogen, $R^4$ is ethyl, n-propyl, n-butyl, cyclohexylmethyl, benzyl, or diethoxymethyl, $R^5$ is hydrogen, and each of $R^6$, $R^7$, and $R^8$ is hydrogen. In certain embodiments of compounds of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, methyl, n-propyl, or isopropyl, $R^3$ is hydrogen, $R^4$ is ethyl, n-propyl, isopropyl, n-butyl, isobutyl, sec-butyl, tert-butyl, n-pentyl, isopentyl, sec-pentyl, neopentyl, n-hexyl, n-heptyl, allyl, 2-methylallyl, but-3-enyl, propargyl, but-2-ynyl, but-3-ynyl, pent-3-ynyl, cyclohexyl, cyclopropylmethyl, cyclobutylmethyl, cyclopentylmethyl, cyclohexylmethyl, cycloheptylmethyl, 2-methoxyethyl, 3-methoxypropyl, 3-ethoxypropyl, 1-hydroxyethyl, 1-hydroxybutyl, 1-hydroxyisobutyl, benzyl, 1-hydroxybenzyl, or diethoxymethyl, $R^5$ is hydrogen, and each of $R^6$, $R^7$, and $R^8$ is hydrogen. In certain embodiments of compounds of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, methyl, n-propyl, or isopropyl, $R^3$ is hydrogen, $R^4$ is n-butyl, $R^5$ is hydrogen, and each of $R^6$, $R^7$, and $R^8$ is hydrogen. In certain embodiments of compounds of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, methyl, n-propyl, or isopropyl, $R^3$ is hydrogen, $R^4$ is cyclohexylmethyl, $R^5$ is hydrogen, and each of $R^6$, $R^7$ and $R^8$ is hydrogen. In certain embodiments of compounds of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, methyl, n-propyl, or isopropyl, $R^3$ is hydrogen, $R^4$ is diethoxymethyl, $R^5$ is hydrogen, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is isopropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is isobutyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is sec-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is tert-butyl, $R^5$ is hydrogen, and each of $R^6$, $R^7$ and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-pentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is isopentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is sec-pentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is neopentyl, $R^5$ is hydrogen, and each of $R^6$, $R^7$ and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-hexyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-heptyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is allyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 2-methylallyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is but-3-enyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is propargyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is but-2-ynyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is but-3-ynyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is pent-3-ynyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclopropylmethyl, $R^1$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclobutylmethyl, $R^1$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclopentylmethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^{51}$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cycloheptylmethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 2-methoxyethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 3-methoxypropyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 3-ethoxypropyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxyethyl, $R^5$ is hydrogen, and each of $R^6$, $R^7$, and $R^8$ is hydrogen. In other embodiments of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxybutyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxyisobutyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is hydrogen, and each of $R^6$, $R^7$ and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxybenzyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is hydrogen, and each of $R^6$, $R^7$ and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is isopropyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^1$ is methyl, $R^3$ is hydrogen, $R^4$ is n-butyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is isobutyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is sec-butyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is tert-butyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-pentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is isopentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is sec-pentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is neopentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-hexyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-heptyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is allyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 2-methylallyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is but-3-enyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl; isobutyl, sec-butyl, tert-butyl, phenyl, cyclohexyl, or 3-pyridyl, $R^2$ is methyl, $R^3$ is hydrogen, $R^4$ is propargyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is but-2-ynyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is but-3-ynyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is pent-3-ynyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclopropylmethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclobutylmethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclopentylmethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cycloheptylmethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 2-methoxyethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 3-methoxypropyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 3-ethoxypropyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxyethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxybutyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxyisobutyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxybenzyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is hydrogen, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is isopropyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is isobutyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is sec-butyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is tert-butyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-pentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is isopentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is sec-pentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is neopentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-hexyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-heptyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is allyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 2-methylallyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is but-3-enyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is propargyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is but-2-ynyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is but-3-ynyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is pent-3-ynyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclopropylmethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclobutylmethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclopentylmethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cycloheptylmethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 2-methoxyethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 3-methoxypropyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 3-ethoxypropyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxyethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxybutyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxyisobutyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxybenzyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is hydrogen, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is isopropyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is isobutyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is sec-butyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is tert-butyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-pentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is isopentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is sec-pentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is neopentyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-hexyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-heptyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is allyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 2-methylallyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is but-3-enyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is propargyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is but-2-ynyl, $R^5$ is hydrogen, and each of $R^6$, $R^7$, and $R^8$ is hydrogen. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is but-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is pent-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclopropylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclobutylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclopentylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cycloheptylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 2-methoxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 3-methoxypropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 3-ethoxypropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxybutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxyisobutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxybenzyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is hydrogen, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is isopropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is isobutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is sec-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is tert-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-pentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is isopentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is sec-pentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is neopentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-hexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-heptyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is allyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 2-methylallyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is but-3-enyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is propargyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is but-2-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is but-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is pent-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclopropylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclobutylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclopentylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cycloheptylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 2-methoxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 3-methoxypropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 3-ethoxypropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxybutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxyisobutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxybenzyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is hydrogen, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is isopropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is isobutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is sec-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is tert-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-pentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is isopentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is sec-pentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is neopentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-hexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-heptyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is allyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 2-methylallyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is but-3-enyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is propargyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is but-2-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is but-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is pent-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclopropylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclobutylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclopentylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cycloheptylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 2-methoxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 3-methoxypropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 3-ethoxypropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxybutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxyisobutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxybenzyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is hydrogen, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is isopropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is isobutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is sec-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is tert-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-pentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is isopentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is sec-pentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is neopentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-hexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-heptyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is allyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 2-methylallyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is but-3-enyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is propargyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is but-2-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is but-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is pent-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclopropylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclobutylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclopentylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cycloheptylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 2-methoxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 3-methoxypropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 3-ethoxypropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxybutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxyisobutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxybenzyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is hydrogen, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is hydrogen, and each of $R^6$, $R^7$, and $R^8$ is hydrogen. In certain embodiments of a compound of Formula (I), $R^1$ is methyl, ethyl, n-propyl, iso-propyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is isopropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is isobutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is sec-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is tert-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-pentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is isopentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is sec-pentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is neopentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-hexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-heptyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is allyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 2-methylallyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is but-3-enyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is propargyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is but-2-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is but-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is pent-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclopropylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclobutylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclopentylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cycloheptylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 2-methoxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 3-methoxypropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 3-ethoxypropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxybutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxyisobutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxybenzyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is hydrogen, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is isopropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is isobutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is sec-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is tert-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-pentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is isopentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is sec-pentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is neopentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-hexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-heptyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is allyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 2-methylallyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is but-3-enyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is propargyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is but-2-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is but-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is pent-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclopropylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclobutylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclopentylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cycloheptylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 2-methoxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 3-methoxypropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 3-ethoxypropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxybutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxyisobutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxybenzyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is hydrogen, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is isopropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is isobutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is sec-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is tert-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-pentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is isopentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is sec-pentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is neopentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-hexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-heptyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is allyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 2-methylallyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is but-3-enyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is propargyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is but-2-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is but-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is pent-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclopropylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclobutylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclopentylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cycloheptylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 2-methoxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 3-methoxypropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 3-ethoxypropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxybutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxyisobutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxybenzyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is hydrogen, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is isopropyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is isobutyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is sec-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is tert-butyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-pentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is isopentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is sec-pentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is neopentyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-hexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-heptyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is allyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 2-methylallyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is but-3-enyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is propargyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is but-2-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is but-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is pent-3-ynyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclopropylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclobutylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclopentylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cycloheptylmethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 2-methoxyethyl, $R^5$ is hydrogen, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, R³ is hydrogen, R⁴ is 3-methoxypropyl, R⁵ is hydrogen, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is cyclohexyl, R³ is hydrogen, R⁴ is 3-ethoxypropyl, R⁵ is hydrogen, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is cyclohexyl, R³ is hydrogen, R⁴ is 1-hydroxyethyl, R⁵ is hydrogen, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is cyclohexyl, R³ is hydrogen, R⁴ is 1-hydroxybutyl, R⁵ is hydrogen, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is cyclohexyl, R³ is hydrogen, R⁴ is 1-hydroxyisobutyl, R⁵ is hydrogen, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is cyclohexyl, R³ is hydrogen, R⁴ is benzyl, R⁵ is hydrogen, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is cyclohexyl, R³ is hydrogen, R⁴ is 1-hydroxybenzyl, R⁵ is hydrogen, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is cyclohexyl, R³ is hydrogen, R⁴ is diethoxymethyl, R⁵ is hydrogen, and each of R⁶, R⁷, and R⁸ is hydrogen.

In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is ethyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is n-propyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is isopropyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is n-butyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is isobutyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is sec-butyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is tert-butyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is n-pentyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is isopentyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is sec-pentyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is neopentyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is n-hexyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is n-heptyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is allyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is 2-methylallyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is but-3-enyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is propargyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is but-2-ynyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is but-3-ynyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is pent-3-ynyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is cyclohexyl, R⁵ is hydroxy, and each of R⁶, R⁷, and R⁸ is hydrogen. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is hydrogen, R³ is hydrogen, R⁴ is cyclopropylmethyl, R⁵ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclobutylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclopentylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cycloheptylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 2-methoxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 3-methoxypropyl, $R^5$ is hydroxy, and each of $R^6$, $R^7$, and $R^2$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 3-ethoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxybutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxyisobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxybenzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is hydroxy, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is isopropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is isobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is sec-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is tert-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is isopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is sec-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is neopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-hexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-heptyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is allyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 2-methylallyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is but-3-enyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is propargyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is but-2-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is but-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is pent-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclopropylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclobutylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclopentylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cycloheptylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 2-methoxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 3-methoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 3-ethoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxybutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxyisobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxybenzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is hydroxy, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is isopropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is isobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is sec-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is tert-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is isopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is sec-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is neopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-hexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-heptyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is allyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 2-methylallyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is but-3-enyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is propargyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is but-2-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is but-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is pent-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclopropylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclobutylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclopentylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cycloheptylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 2-methoxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 3-methoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 3-ethoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxybutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxyisobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxybenzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is hydroxy, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is isopropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is isobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is sec-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is tert-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is isopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is sec-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is neopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-hexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-heptyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is allyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 2-methylallyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is but-3-enyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is propargyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is but-2-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is but-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is pent-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclopropylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclobutylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclopentylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cycloheptylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 2-methoxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 3-methoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 3-ethoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxybutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxyisobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxybenzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is hydroxy, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is isopropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is isobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is sec-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is tert-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is isopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is sec-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is neopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-hexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-heptyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is allyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 2-methylallyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is but-3-enyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is propargyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is but-2-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is but-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is pent-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclopropylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclobutylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclopentylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cycloheptylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 2-methoxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 3-methoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 3-ethoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxybutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxyisobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxybenzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is hydroxy, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is isopropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is isobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is sec-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is tert-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is isopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is sec-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is neopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-hexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-heptyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is allyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 2-methylallyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is but-3-enyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is propargyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is but-2-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is but-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is pent-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclopropylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclobutylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclopentylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cycloheptylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 2-methoxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 3-methoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 3-ethoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxybutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxyisobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxybenzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is hydroxy, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is isopropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is isobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is sec-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is tert-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is isopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is sec-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is neopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-hexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-heptyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is allyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 2-methylallyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is but-3-enyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is propargyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is but-2-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is but-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is pent-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclopropylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclobutylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclopentylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cycloheptylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 2-methoxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 3-methoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 3-ethoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxybutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxyisobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxybenzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is hydroxy, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is isopropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is isobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is sec-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is tert-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is isopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is sec-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is neopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-hexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-heptyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is allyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 2-methylallyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is but-3-enyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is propargyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is but-2-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is but-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is pent-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclopropylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclobutylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclopentylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cycloheptylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 2-methoxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 3-methoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 3-ethoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxybutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxyisobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxybenzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is hydroxy, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I) $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is isopropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is isobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is sec-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is tert-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is isopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is sec-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is neopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-hexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-heptyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is allyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 2-methylallyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is but-3-enyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is propargyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is but-2-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is but-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is pent-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclopropylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclobutylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclopentylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cycloheptylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 2-methoxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 3-methoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 3-ethoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxybutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxyisobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxybenzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is hydroxy, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is isopropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is isobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is sec-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is tert-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is isopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is sec-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is neopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-hexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-heptyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is allyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 2-methylallyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is but-3-enyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is propargyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is but-2-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is but-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is pent-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclopropylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclobutylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclopentylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cycloheptylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 2-methoxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 3-methoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 3-ethoxypropyl, $R^5$ is hydroxy, and each of $R^6$; $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxybutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxyisobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxybenzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is hydroxy, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is isopropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is isobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is sec-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is tert-butyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is isopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is sec-pentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is neopentyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-hexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-heptyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is allyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 2-methylallyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is but-3-enyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is propargyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is but-2-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is but-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is pent-3-ynyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclopropylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclobutylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclopentylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cycloheptylmethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 2-methoxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 3-methoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 3-ethoxypropyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 1-hydroxyethyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 1-hydroxybutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 1-hydroxyisobutyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 1-hydroxybenzyl, $R^5$ is hydroxy, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is hydroxy, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is isopropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is isobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is sec-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is tert-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is isopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is sec-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is neopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-hexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-heptyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is allyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 2-methylallyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is but-3-enyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is propargyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is but-2-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is but-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is pent-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclopropylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclobutylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclopentylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cycloheptylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 2-methoxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 3-methoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 3-ethoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxybutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxyisobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxy benzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is fluoro, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is isopropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is isobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is sec-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is tert-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is isopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is sec-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is neopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-hexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-heptyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is allyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 2-methylallyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is but-3-enyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is propargyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is but-2-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is but-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is pent-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclopropylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclobutylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclopentylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cycloheptylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 2-methoxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 3-methoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 3-ethoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxybutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxyisobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxybenzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is fluoro, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is isopropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is isobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is sec-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is tert-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is isopentyl, $R^5$ is fluoro, and each of $R^6$, $R^7$, and $R^8$ is hydrogen. In certain embodiments of a compound of Formula (I), $R^1$ is methyl, ethyl, n-propyl, iso-propyl, n-butyl, isobutyl, sec-butyl, tert-butyl, phenyl, cyclohexyl, or 3-pyridyl, $R^2$ is ethyl, $R^3$ is hydrogen, $R^4$ is sec-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is neopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-hexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-heptyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is allyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 2-methylallyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is but-3-enyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is propargyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is but-2-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is but-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is pent-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclopropylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclobutylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclopentylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cycloheptylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 2-methoxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 3-methoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 3-ethoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxybutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxyisobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxybenzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is fluoro, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is isopropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is isobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is sec-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is tert-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is isopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is sec-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is neopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-hexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-heptyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is allyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 2-methylallyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is but-3-enyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is propargyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is but-2-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is but-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is pent-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclopropylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclobutylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclopentylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cycloheptylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 2-methoxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 3-methoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 3-ethoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxybutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxyisobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxybenzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is fluoro, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is isopropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is isobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is sec-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is tert-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is isopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is sec-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is neopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-hexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-heptyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is allyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 2-methylallyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is but-3-enyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is propargyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is but-2-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is but-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is pent-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclopropylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclobutylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclopentylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cycloheptylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 2-methoxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 3-methoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 3-ethoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxybutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxyisobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxybenzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is fluoro, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is isopropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is isobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is sec-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is tert-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is isopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is sec-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is neopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-hexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-heptyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is allyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 2-methylallyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is but-3-enyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is propargyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is but-2-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is but-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is pent-3-ynyl, $R^5$ is fluoro, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclopropylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclobutylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclopentylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cycloheptylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 2-methoxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 3-methoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 3-ethoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxybutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxyisobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxybenzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is fluoro, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is isopropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is isobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is sec-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is tert-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is isopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is sec-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is neopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-hexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-heptyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is allyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 2-methylallyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is but-3-enyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is propargyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is but-2-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is but-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is pent-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclopropylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclobutylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclopentylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cycloheptylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 2-methoxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 3-methoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 3-ethoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxybutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxyisobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is fluoro, and each of $R^6$, $R^7$, and $R^8$ is independently hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxybenzyl, $R^5$ is fluoro, and each of $R^6$, $R^7$, and $R^8$ is independently hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is fluoro, and each of $R^6$, $R^7$, and $R^8$ is independently hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I) $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is fluoro, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is isopropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is isobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is sec-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is tert-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is isopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is sec-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is neopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-hexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-heptyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is allyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 2-methylallyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is but-3-enyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is propargyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is but-2-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is but-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is pent-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclopropylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclobutylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclopentylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cycloheptylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 2-methoxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 3-methoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 3-ethoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxybutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxyisobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxybenzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is fluoro, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is isopropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is isobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is sec-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is tert-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is isopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is sec-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is neopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-hexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-heptyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is allyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 2-methylallyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is but-3-enyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is propargyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is but-2-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is but-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is pent-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclopropylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclobutylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclopentylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cycloheptylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 2-methoxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 3-methoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 3-ethoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxybutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxyisobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxybenzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is fluoro, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is isopropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is isobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is sec-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is tert-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is isopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is sec-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is neopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-hexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-heptyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is allyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 2-methylallyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is but-3-enyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is propargyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is but-2-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is but-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is pent-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclopropylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclobutylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclopentylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cycloheptylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 2-methoxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 3-methoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 3-ethoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxybutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxyisobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxybenzyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is fluoro, and each of $R^6$, $R^7$, and $R^8$ is hydrogen. In certain of the above embodiments of a compound of Formula (I), the carbon to which $R^5$ is bonded is of the R configuration. In certain of the above embodiments of a compound of Formula (I), the carbon to which $R^5$ is bonded is of the S configuration.

In certain embodiments of a compound of Formula (I), $R^1$ methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is isopropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is isobutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is sec-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is tert-butyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is isopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is sec-pentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is neopentyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-hexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-heptyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is allyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 2-methylallyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is but-3-enyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is propargyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is but-2-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is but-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is pent-3-ynyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclopropylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclobutylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclopentylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cycloheptylmethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 2-methoxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 3-methoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 3-ethoxypropyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 1-hydroxyethyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 1-hydroxybutyl, $R^5$ is fluoro, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 1-hydroxyisobutyl, $R^5$ is fluoro, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is cyclohexyl, R$^3$ is hydrogen, R$^4$ is benzyl, R$^5$ is fluoro, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is cyclohexyl, R$^3$ is hydrogen, R$^4$ is 1-hydroxybenzyl, R$^5$ is fluoro, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is cyclohexyl, R$^3$ is hydrogen, R$^4$ is diethoxymethyl, R$^5$ is fluoro, and each of R$^6$, R$^7$, and R$^8$ is hydrogen. In certain of the above embodiments of a compound of Formula (I), the carbon to which R$^5$ is bonded is of the R configuration. In certain of the above embodiments of a compound of Formula (I), the carbon to which R$^5$ is bonded is of the S configuration.

In certain embodiments of a compound of Formula (I) R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is ethyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is n-propyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is isopropyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is n-butyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is isobutyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is sec-butyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is tert-butyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is n-pentyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is isopentyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is sec-pentyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is neopentyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is n-hexyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is n-heptyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is allyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is 2-methylallyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is but-3-enyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is propargyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is but-2-ynyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is but-3-ynyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is pent-3-ynyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is cyclohexyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is cyclopropylmethyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is cyclobutylmethyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is cyclopentylmethyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is cyclohexylmethyl, R$^5$ is oxo, and each of R$^6$, R$^7$, and R$^8$ is hydrogen. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, $R^4$ is cycloheptylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 2-methoxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 3-methoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 3-ethoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1 hydroxybutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxyisobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is 1-hydroxybenzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is oxo, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is isopropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is isobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is sec-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is tert-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is isopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is sec-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is neopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-hexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-heptyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is allyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 2-methylallyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is but-3-enyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is propargyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is but-2-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is but-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is pent-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclopropylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclobutylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclopentylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cycloheptylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 2-methoxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 3-methoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 3-ethoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxybutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxyisobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is 1-hydroxybenzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is oxo, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is isopropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is isobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is sec-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is tert-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is isopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is sec-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is neopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-hexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-heptyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is allyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 2-methylallyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is but-3-enyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is propargyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is but-2-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is but-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is pent-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclopropylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclobutylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclopentylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cycloheptylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 2-methoxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 3-methoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 3-ethoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxybutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxyisobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is 1-hydroxybenzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is oxo, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is isopropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is isobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is sec-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is tert-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is isopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is sec-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is neopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-hexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-heptyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is allyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 2-methylallyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is but-3-enyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is propargyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is but-2-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is but-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is pent-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclopropylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclobutylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclopentylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cycloheptylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 2-methoxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 3-methoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 3-ethoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxybutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxyisobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is 1-hydroxybenzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is oxo, and each of $R^6$, $R^7$, and $R^8$ is hydrogen.

In certain embodiments of a compound of Formula (I) $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is isopropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is isobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is sec-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is tert-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is isopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is sec-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is neopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-hexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-heptyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is allyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 2-methylallyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is but-3-enyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is propargyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is but-2-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is but-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is pent-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclopropylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclobutylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclopentylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cycloheptylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 2-methoxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 3-methoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 3-ethoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxybutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxyisobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is 1-hydroxybenzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is oxo, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is isopropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is isobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is sec-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is tert-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is isopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is sec-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is neopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-hexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-heptyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is allyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 2-methylallyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is but-3-enyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is propargyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is but-2-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is but-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is pent-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclopropylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclobutylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclopentylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cycloheptylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 2-methoxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 3-methoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 3-ethoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxybutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxyisobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is 1-hydroxybenzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is oxo, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is isopropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is isobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is sec-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is tert-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is isopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is sec-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is neopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-hexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-heptyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is allyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 2-methylallyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is but-3-enyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is propargyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is but-2-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is but-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is pent-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclopropylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclobutylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclopentylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cycloheptylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 2-methoxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 3-methoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 3-ethoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxybutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxyisobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is 1-hydroxybenzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is oxo, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is isopropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is isobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is sec-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is tert-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is isopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is sec-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is neopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-hexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-heptyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is allyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 2-methylallyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is but-3-enyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is propargyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is but-2-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is but-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is pent-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclopropylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclobutylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclopentylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cycloheptylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 2-methoxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 3-methoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 3-ethoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxybutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxyisobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is 1-hydroxybenzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is oxo, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is isopropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is isobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is sec-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is tert-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is isopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is sec-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is neopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-hexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-heptyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is allyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 2-methylallyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is but-3-enyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is propargyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is but-2-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is but-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is pent-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclopropylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclobutylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclopentylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cycloheptylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 2-methoxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 3-methoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 3-ethoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxybutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxyisobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is 1-hydroxybenzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is oxo, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is isopropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is isobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is sec-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is tert-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, phenyl, cyclohexyl, or 3-pyridyl, $R^2$ is phenyl, $R^3$ is hydrogen, $R^4$ is n-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is isopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is sec-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is neopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-hexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-heptyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is allyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl; isobutyl, sec-butyl, tert-butyl, phenyl, cyclohexyl, or 3-pyridyl, $R^2$ is phenyl, $R^3$ is hydrogen, $R^4$ is 2-methylallyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is but-3-enyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is propargyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is but-2-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is but-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is pent-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclopropylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclobutylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclopentylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cycloheptylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 2-methoxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 3-methoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 3-ethoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxybutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxyisobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is 1-hydroxybenzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is oxo, and each of $R^6$, $R^7$, and $R^8$ is hydrogen.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is isopropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is isobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is sec-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is tert-butyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is isopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is sec-pentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is neopentyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-hexyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-heptyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is allyl, $R^5$ is oxo, and each of $R^6$, $R^7$; and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 2-methylallyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is but-3-enyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is propargyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is but-2-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is but-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is pent-3-ynyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexyl, $R^5$ is oxo, and each of $R^6$, $R^7$ and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclopropylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclobutylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclopentylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cycloheptylmethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 2-methoxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 3-methoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 3-ethoxypropyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 1-hydroxyethyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 1-hydroxybutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 1-hydroxyisobutyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is 1-hydroxybenzyl, $R^5$ is oxo, and each of $R^6$, $R^7$, and $R^8$ is hydrogen. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is oxo, and each of $R^6$, $R^7$, and $R^8$ is hydrogen.

In certain embodiments of a compound of Formula (I), $R^1$ is chosen from $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ is chosen from hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl and pyridyl, $R^3$ is hydrogen, $R^4$ is chosen from $C_{2-6}$ alkyl, substituted $C_{2-6}$ alkyl, benzyl, substituted benzyl, $C_{4-7}$ cycloalkyl, $C_{3-7}$ cycloalkylmethyl and dialkoxymethyl, $R^5$ is chosen from hydrogen, hydroxy, mercapto, fluoro, oxo, $C_{1-4}$ alkyl, aryl, substituted aryl, $C_{3-6}$ cycloalkyl, heteroaryl, substituted heteroaryl, $C_{7-9}$ phenylalkyl and substituted $C_{7-9}$ phenylalkyl, each of $R^6$ and $R^7$ is hydrogen, and $R^8$ is $C_{7-9}$ phenylalkyl, or substituted $C_{7-9}$ phenylalkyl. In certain of the above embodiments of a compound of Formula (I), $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, or 4-pyridyl, and in certain embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, or 3-pyridyl. In certain of the above embodiments of a compound of Formula (I), $R^2$ is hydrogen, methyl, ethyl, n-propyl, isopropyl, n-butyl, isobutyl, sec-butyl, tert-butyl, cyclopentyl, cyclohexyl, phenyl, benzyl, phenethyl, 2-pyridyl, 3-pyridyl, or 4-pyridyl, and in certain embodiments, $R^2$ is hydrogen, methyl, ethyl, n-propyl, isopropyl, n-butyl, isobutyl, sec-butyl, tert-butyl, cyclohexyl, or phenyl. In certain of the above embodiments of a compound of Formula (I), $R^4$ is ethyl, n-propyl, isopropyl, n-butyl, isobutyl, sec-butyl, tert-butyl, n-pentyl, isopentyl, sec-pentyl, neopentyl, n-hexyl, n-heptyl, allyl, 2-methylallyl, but-3-enyl, propargyl, but-2-ynyl, but-3-ynyl, pent-3-ynyl, cyclohexyl, cyclopropylmethyl, cyclobutylmethyl, cyclopentylmethyl, cyclohexylmethyl, cycloheptylmethyl, 2-methoxyethyl, 3-methoxypropyl, 3-ethoxypropyl, 1-hydroxyethyl, 1-hydroxybutyl, 1-hydroxyisobutyl, benzyl, 1-hydroxybenzyl, or diethoxymethyl, and in certain embodiments, $R^4$ is ethyl, n-propyl, n-butyl, diethoxymethyl, cyclohexylmethyl, or benzyl. In certain of the above embodiments of a compound of Formula (I), $R^5$ is hydrogen, hydroxy, fluoro, oxo, or 4-chlorophenyl. In certain of the above embodiments of a compound of Formula (I), $R^8$ is 3,5-dichlorobenzyl, 1-(3-chlorophenyl)ethyl, 1-(3,4-dichlorophenyl)ethyl, 1-(3-chloro-4-iodophenyl)ethyl, 1-(4-chloro-3-iodophenyl)ethyl, 3,4-dimethylbenzyl, 1-(2,4-dimethoxyphenyl)ethyl, 1-(2,5-dimethoxyphenyl)ethyl, 1-(2,6-dimethoxyphenyl)ethyl, 1-(3,4-dimethoxyphenyl)ethyl, 1-(3,5-dimethoxyphenyl)ethyl, 1-(3,4,5-trimethoxyphenyl)ethyl, 3-carboxybenzyl, 3-cyanobenzyl, 4-carboxybenzyl, 4-cyanobenzyl, 1-(3-carboxyphenyl)ethyl, 1-(3-cyanophenyl)ethyl, 1-(4-carboxyphenyl)ethyl, 1-(4-cyanophenyl)ethyl, 3-phenylprop-2-yl, 2-(3,4-dichlorophenyl)propyl, 3-(3,4-dichlorophenyl)prop-2-yl, or 3-phenyl-3-hydroxyprop-2-yl, and in certain embodiments $R^8$ is 1-(3,4-dichlorophenyl)ethyl, 1-(3-carboxyphenyl)ethyl, 1-(4-carboxyphenyl)ethyl, 3,5-dichlorobenzyl, 3-carboxybenzyl, or 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is hydrogen, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is hydrogen, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is hydrogen, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is hydrogen, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is hydrogen, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is hydrogen, each of $R^6$ and $R^7$ is hydrogen, and $R^8$ is 1-(3,4-dichlorophenyl) ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is hydrogen, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is hydrogen, each of $R^6$ and $R^7$ is hydrogen, and $R^8$ is 1-(3,4-dichlorophenyl) ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is hydrogen, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is hydrogen, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is hydrogen, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is hydrogen, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is hydrogen, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is hydrogen, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is hydroxy, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In still certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is hydroxy, each of R⁶ and R⁷ is hydrogen, and R⁸ is 1-(3,4-dichlorophenyl)ethyl. In certain of the above embodiments of a compound of Formula (I), the carbon to which R⁵ is bonded is of the S-configuration and the α-carbon of the 1-(3,4-dichlorophenyl)ethyl group is of the S-configuration. In certain of the above embodiments of a compound of Formula (I), the carbon to which R⁵ is bonded is of the R-configuration and the α-carbon of the 1-(3,4-dichlorophenyl)ethyl group is of the S-configuration. In certain of the above embodiments of a compound of Formula (I), the carbon to which R⁵ is bonded is of the S-configuration and the α-carbon of the 1-(3,4-dichlorophenyl)ethyl group is of the R-configuration. In certain of the above embodiments of a compound of Formula (I), the carbon to which R⁵ is bonded is of the R-configuration and the α-carbon of the 1-(3,4-dichlorophenyl)ethyl group is of the R-configuration.

In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is ethyl, R³ is hydrogen, R⁴ is ethyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is ethyl, R³ is hydrogen, R⁴ is n-propyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is ethyl, R³ is hydrogen, R⁴ is n-butyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is ethyl, R³ is hydrogen, R⁴ is diethoxymethyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is ethyl, R³ is hydrogen, R⁴ is cyclohexylmethyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is ethyl, R³ is hydrogen, R⁴ is benzyl, R⁵ is hydroxy, each of R⁶ and R⁷ is hydrogen, and R⁸ is 1-(3,4-dichlorophenyl)ethyl. In certain of the above embodiments of a compound of Formula (I), the carbon to which R⁵ is bonded is of the S-configuration and the α-carbon of the 1-(3,4-dichlorophenyl)ethyl group is of the S-configuration. In certain of the above embodiments of a compound of Formula (I), the carbon to which R⁵ is bonded is of the R-configuration and the α-carbon of the 1-(3,4-dichlorophenyl)ethyl group is of the S-configuration. In certain of the above embodiments of a compound of Formula (I), the carbon to which R⁵ is bonded is of the S-configuration and the α-carbon of the 1-(3,4-dichlorophenyl)ethyl group is of the R-configuration. In certain of the above embodiments of a compound of Formula (I), the carbon to which R⁵ is bonded is of the R-configuration and the α-carbon of the 1-(3,4-dichlorophenyl)ethyl group is of the R-configuration.

In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-propyl, R³ is hydrogen, R⁴ is ethyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-propyl, R³ is hydrogen, R⁴ is n-propyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-propyl, R³ is hydrogen, R⁴ is n-butyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-propyl, R³ is hydrogen, R⁴ is diethoxymethyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-propyl, R³ is hydrogen, R⁴ is cyclohexylmethyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-propyl, R³ is hydrogen, R⁴ is benzyl, R⁵ is hydroxy, each of R⁶ and R⁷ is hydrogen, and R⁸ is 1-(3,4-dichlorophenyl)ethyl. In certain of the above embodiments of a compound of Formula (I), the carbon to which R⁵ is bonded is of the S-configuration and the α-carbon of the 1-(3,4-dichlorophenyl)ethyl group is of the S-configuration. In certain of the above embodiments of a compound of Formula (I), the carbon to which R⁵ is bonded is of the R-configuration and the α-carbon of the 1-(3,4-dichlorophenyl)ethyl group is of the S-configuration. In certain of the above embodiments of a compound of Formula (I), the carbon to which R⁵ is bonded is of the S-configuration and the α-carbon of the 1-(3,4-dichlorophenyl)ethyl group is of the R-configuration. In certain of the above embodiments of a compound of Formula (I), the carbon to which R⁵ is bonded is of the R-configuration and the α-carbon of the 1-(3,4-dichlorophenyl)ethyl group is of the R-configuration.

In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is ethyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is n-propyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is n-butyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is diethoxymethyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is cyclohexylmethyl, R⁵ is hydroxy, each of R⁶ and R⁷ is hydrogen, and R⁸ is 1-(3,4-dichlorophenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is benzyl, R⁵ is hydroxy, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is hydroxy, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is hydroxy, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is hydroxy, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is hydroxy, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is hydroxy, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is hydroxy, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is hydroxy, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is fluoro, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is fluoro, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is fluoro, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is fluoro, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is fluoro, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is fluoro, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is fluoro, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is fluoro, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is fluoro, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is fluoro, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is fluoro, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is fluoro, each of $R^6$ and $R^7$ is hydrogen, and $R^8$ is 1-(3,4-dichlorophenyl)ethyl. In certain of the above embodiments of a compound of Formula (I), the carbon to which $R^5$ is bonded is of the S-configuration and the α-carbon of the 1-(3,4-dichlorophenyl)ethyl group is of the S-configuration. In certain of the above embodiments of a compound of Formula (I), the carbon to which $R^5$ is bonded is of the R-configuration and the α-carbon of the 1-(3,4-dichlorophenyl)ethyl group is of the S-configuration. In certain of the above embodiments of a compound of Formula (I), the carbon to which $R^5$ is bonded is of the S-configuration and the α-carbon of the 1-(3,4-dichlorophenyl)ethyl group is of the R-configuration. In certain of the above embodiments of a compound of Formula (I), the carbon to which $R^5$ is bonded is of the R-configuration and the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is oxo, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is oxo, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is oxo, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is oxo, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is oxo, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is oxo, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is oxo, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is oxo, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is oxo, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is oxo, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is oxo, each of $R^6$ and $R^7$ is hydrogen, and $R^8$ is 1-(3,4-dichlorophenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is oxo, each of $R^6$ and $R^7$ is hydrogen, and $R^8$ is 1-(3,4-dichlorophenyl)ethyl. In certain of the above embodiments of a compound of Formula (I), the α-carbon of the 1-(3,4-dichlorophenyl)ethyl group is of the S-configuration. In certain of the above embodiments of a compound of Formula (I), the α-carbon of the 1-(3,4-dichlorophenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is hydrogen, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is hydrogen, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is hydrogen, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is hydrogen, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is hydrogen, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is hydrogen, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is hydrogen, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is hydrogen, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is hydrogen, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is hydrogen, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is hydrogen, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is hydrogen, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is hydroxy, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is hydroxy, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is hydroxy, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is hydroxy, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is hydroxy, each of $R^6$ and $R^7$ is hydrogen, and $R^8$ is 1-(3-carboxyphenyl) ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is hydroxy, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is hydroxy, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is hydroxy, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is hydroxy, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is hydroxy, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is hydroxy, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is hydroxy, each of $R^6$ and $R^7$ is hydrogen, and $R^8$ is 1-(3-carboxyphenyl) ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is hydroxy, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is hydroxy, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is fluoro, each of $R^6$ and $R^7$ is hydrogen, and $R^8$ is 1-(3-carboxyphenyl) ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is fluoro, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is fluoro, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is fluoro, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is fluoro, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is fluoro, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^1$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is fluoro, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is fluoro, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is fluoro, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is fluoro, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is fluoro, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is fluoro, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is fluoro, each of $R^6$ and $R^7$ is hydrogen, and $R^8$ is 1-(3-carboxyphenyl)ethyl. In certain of the above embodiments of a compound of Formula (I), the carbon to which $R^5$ is bonded is of the S-configuration and the α-carbon of the 1-(3-carboxyphenyl)ethyl group is of the S-configuration. In certain of the above embodiments of a compound of Formula (I), the carbon to which $R^5$ is bonded is of the R-configuration and the α-carbon of the 1-(3-carboxyphenyl)ethyl group is of the S-configuration. In certain of the above embodiments of a compound of Formula (I), the carbon to which $R^5$ is bonded is of the S-configuration and the α-carbon of the 1-(3-carboxyphenyl)ethyl group is of the R-configuration. In certain of the above embodiments of a compound of Formula (I), the carbon to which $R^5$ is bonded is of the R-configuration and the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is oxo, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is oxo, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is oxo, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is oxo, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is oxo, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is oxo, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is oxo, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is oxo, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is oxo, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is oxo, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is oxo, each of $R^6$ and $R^7$ is hydrogen, and $R^8$ is 1-(3-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is oxo, each of $R^6$ and $R^7$ is hydrogen, and $R^8$ is 1-(3-carboxyphenyl)ethyl. In certain of the above embodiments of a compound of Formula (I), the α-carbon of the 1-(3-carboxyphenyl)ethyl group is of the S-configuration. In certain of the above embodiments of a compound of Formula (I), the α-carbon of the 1-(3-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is hydrogen, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is hydrogen, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is hydrogen, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is hydrogen, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is hydrogen, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is hydrogen, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is hydrogen, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is hydrogen, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is hydrogen, each of $R^6$ and $R^7$ is hydrogen, and $R^8$ is 1-(4-carboxyphenyl)

ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is hydrogen, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is hydrogen, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is hydrogen, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is hydrogen, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is hydroxy, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is hydroxy, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is hydroxy, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is hydroxy, each of $R^6$ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is n-propyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is n-butyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is diethoxymethyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is cyclohexylmethyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is benzyl, R⁵ is hydroxy, each of R⁶ and R⁷ is hydrogen, and R⁸ is 1-(4-carboxyphenyl)ethyl. In certain of the above embodiments of a compound of Formula (I), the carbon to which R⁵ is bonded is of the S-configuration and the α-carbon of the 1-(4-carboxyphenyl)ethyl group is of the S-configuration. In certain of the above embodiments of a compound of Formula (I), the carbon to which R⁵ is bonded is of the R-configuration and the α-carbon of the 1-(4-carboxyphenyl)ethyl group is of the S-configuration. In certain of the above embodiments of a compound of Formula (I), the carbon to which R⁵ is bonded is of the S-configuration and the α-carbon of the 1-(4-carboxyphenyl)ethyl group is of the R-configuration. In certain of the above embodiments of a compound of Formula (I), the carbon to which R⁵ is bonded is of the R-configuration and the α-carbon of the 1-(4-carboxyphenyl)ethyl group is of the R-configuration.

In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-butyl, R³ is hydrogen, R⁴ is ethyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-butyl, R³ is hydrogen, R⁴ is n-propyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-butyl, R³ is hydrogen, R⁴ is n-butyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-butyl, R³ is hydrogen, R⁴ is diethoxymethyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-butyl, R³ is hydrogen, R⁴ is cyclohexylmethyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-butyl, R³ is hydrogen, R⁴ is benzyl, R⁵ is hydroxy, each of R⁶ and R⁷ is hydrogen, and R⁸ is 1-(4-carboxyphenyl)ethyl. In certain of the above embodiments of a compound of Formula (I), the carbon to which R⁵ is bonded is of the S-configuration and the α-carbon of the 1-(4-carboxyphenyl)ethyl group is of the S-configuration. In certain of the above embodiments of a compound of Formula (I), the carbon to which R⁵ is bonded is of the R-configuration and the α-carbon of the 1-(4-carboxyphenyl)ethyl group is of the S-configuration. In certain of the above embodiments of a compound of Formula (I), the carbon to which R⁵ is bonded is of the S-configuration and the α-carbon of the 1-(4-carboxyphenyl)ethyl group is of the R-configuration. In certain of the above embodiments of a compound of Formula (I), the carbon to which R⁵ is bonded is of the R-configuration and the α-carbon of the 1-(4-carboxyphenyl)ethyl group is of the R-configuration.

In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isobutyl, R³ is hydrogen, R⁴ is ethyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isobutyl, R³ is hydrogen, R⁴ is n-propyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isobutyl, R³ is hydrogen, R⁴ is n-butyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isobutyl, R³ is hydrogen, R⁴ is diethoxymethyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isobutyl, R³ is hydrogen, R⁴ is cyclohexylmethyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isobutyl, R³ is hydrogen, R⁴ is benzyl, R⁵ is hydroxy, each of R⁶ and R⁷ is hydrogen, and R⁸ is 1-(4-carboxyphenyl)ethyl. In certain of the above embodiments of a compound of Formula (I), the carbon to which R⁵ is bonded is of the S-configuration and the α-carbon of the 1-(4-carboxyphenyl)ethyl group is of the S-configuration. In certain of the above embodiments of a compound of Formula (I), the carbon to which R⁵ is bonded is of the R-configuration and the α-carbon of the 1-(4-carboxyphenyl)ethyl group is of the S-configuration. In certain of the above embodiments of a compound of Formula (I), the carbon to which R⁵ is bonded is of the S-configuration and the α-carbon of the 1-(4-carboxyphenyl)ethyl group is of the R-configuration. In certain of the above embodiments of a compound of Formula (I), the carbon to which R⁵ is bonded is of the R-configuration and the α-carbon of the 1-(4-carboxyphenyl)ethyl group is of the R-configuration.

In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is sec-butyl, R³ is hydrogen, R⁴ is ethyl, R⁵ is hydroxy, each of R⁶ and R⁷ is hydrogen, and R⁸ is 1-(4-carboxyphenyl)ethyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is hydroxy, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is hydroxy, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is hydroxy, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is hydroxy, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is hydroxy, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is fluoro, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is fluoro, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is fluoro, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is fluoro, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is fluoro, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is fluoro, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is fluoro, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is fluoro, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is fluoro, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is fluoro, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is fluoro, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is fluoro, each of $R^6$ and $R^7$ is hydrogen, and $R^8$ is 1-(4-carboxyphenyl)ethyl. In certain of the above embodiments of a compound of Formula (I), the carbon to which $R^5$ is bonded is of the S-configuration and the α-carbon of the 1-(4-carboxyphenyl)ethyl group is of the S-configuration. In certain of the above embodiments of a compound of Formula (I), the carbon to which $R^5$ is bonded is of the R-configuration and the α-carbon of the 1-(4-carboxyphenyl)ethyl group is of the S-configuration. In certain of the above embodiments of a compound of Formula (I), the carbon to which $R^5$ is bonded is of the S-configuration and the α-carbon of the 1-(4-carboxyphenyl)ethyl group is of the R-configuration. In certain of the above embodiments of a compound of Formula (I), the carbon to which $R^5$ is bonded is of the R-configuration and the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is oxo, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is oxo, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is oxo, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is oxo, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is oxo, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is oxo, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is oxo, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is oxo, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is oxo, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is oxo, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is oxo, each of $R^6$ and $R^7$ is hydrogen, and $R^8$ is 1-(4-carboxyphenyl)ethyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is oxo, each of $R^6$ and $R^7$ is hydrogen, and $R^8$ is 1-(4-carboxyphenyl)ethyl. In certain of the above embodiments of a compound of Formula (I), the α-carbon of the 1-(4-carboxyphenyl)ethyl group is of the S-configuration. In certain of the above embodiments of a compound of Formula (I), the α-carbon of the 1-(4-carboxyphenyl)ethyl group is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is hydrogen, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is hydrogen, each of $R^6$ and $R^7$ is hydrogen, and $R^8$ is 3,5-dichlorobenzyl.

In certain embodiments of a compound of Formula (I), $R^1$ methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is hydrogen, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is hydrogen, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is hydrogen, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is hydrogen, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is hydrogen, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is hydrogen, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is hydrogen, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is hydrogen, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is hydrogen, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is hydrogen, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is hydroxy, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is hydroxy, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is hydroxy, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is hydroxy, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is hydroxy, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is hydroxy, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is hydroxy, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is hydroxy, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is hydroxy, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is hydroxy, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is hydroxy, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is hydroxy, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is fluoro, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is fluoro, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is fluoro, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is fluoro, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is fluoro, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is fluoro, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is fluoro, each of $R^6$ and $R^7$ is hydrogen, and $R^8$ is 3,5-dichlorobenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is fluoro, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is fluoro, each of $R^6$ and $R^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is sec-butyl, R$^3$ is hydrogen, R$^4$ is benzyl, R$^5$ is fluoro, each of R$^6$ and R$^7$ is hydrogen, and R$^8$ is 3,5-dichlorobenzyl. In certain of the above embodiments of a compound of Formula (I), the carbon to which R$^5$ is bonded is of the S-configuration. In certain of the above embodiments of a compound of Formula (I), the carbon to which R$^5$ is bonded is of the R-configuration.

In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is tert-butyl, R$^3$ is hydrogen, R$^4$ is ethyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is tert-butyl, R$^3$ is hydrogen, R$^4$ is n-propyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is tert-butyl, R$^3$ is hydrogen, R$^4$ is n-butyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is tert-butyl, R$^3$ is hydrogen, R$^4$ is diethoxymethyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is tert-butyl, R$^3$ is hydrogen, R$^4$ is cyclohexylmethyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is tert-butyl, R$^3$ is hydrogen, R$^4$ is benzyl, R$^5$ is fluoro, each of R$^6$ and R$^7$ is hydrogen, and R$^8$ is 3,5-dichlorobenzyl. In certain of the above embodiments of a compound of Formula (I), the carbon to which R$^5$ is bonded is of the S-configuration. In certain of the above embodiments of a compound of Formula (I), the carbon to which R$^5$ is bonded is of the R-configuration.

In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is phenyl, R$^3$ is hydrogen, R$^4$ is ethyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is phenyl, R$^3$ is hydrogen, R$^4$ is n-propyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is phenyl, R$^3$ is hydrogen, R$^4$ is n-butyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is phenyl, R$^3$ is hydrogen, R$^4$ is diethoxymethyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is phenyl, R$^3$ is hydrogen, R$^4$ is cyclohexylmethyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is phenyl, R$^3$ is hydrogen, R$^4$ is benzyl, R$^5$ is fluoro, each of R$^6$ and R$^7$ is hydrogen, and R$^8$ is 3,5-dichlorobenzyl. In certain of the above embodiments of a compound of Formula (I), the carbon to which R$^5$ is bonded is of the S-configuration. In certain of the above embodiments of a compound of Formula (I), the carbon to which R$^5$ is bonded is of the R-configuration.

In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is cyclohexyl, R$^3$ is hydrogen, R$^4$ is ethyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is cyclohexyl, R$^3$ is hydrogen, R$^4$ is n-propyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is cyclohexyl, R$^3$ is hydrogen, R$^4$ is n-butyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is cyclohexyl, R$^3$ is hydrogen, R$^4$ is diethoxymethyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is cyclohexyl, R$^3$ is hydrogen, R$^4$ is cyclohexylmethyl, R$^5$ is fluoro, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is cyclohexyl, R$^3$ is hydrogen, R$^4$ is benzyl, R$^5$ is fluoro, each of R$^6$ and R$^7$ is hydrogen, and R$^8$ is 3,5-dichlorobenzyl. In certain of the above embodiments of a compound of Formula (I), the carbon to which R$^5$ is bonded is of the S-configuration. In certain of the above embodiments of a compound of Formula (I), the carbon to which R$^5$ is bonded is of the R-configuration.

In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is ethyl, R$^5$ is oxo, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is n-propyl, R$^5$ is oxo, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is n-butyl, R$^5$ is oxo, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, R$^2$ is hydrogen, R$^3$ is hydrogen, R$^4$ is diethoxymethyl, R$^5$ is oxo, each of R$^6$ and R$^7$ is hydrogen, and R$^8$ is 3,5-dichlorobenzyl. In certain embodiments of a compound of Formula (I), R$^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is oxo, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is oxo, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is oxo, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is oxo, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is oxo, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is oxo, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is oxo, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is oxo, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is oxo, each of $R^6$ and $R^7$ is hydrogen, and $R^8$ is 3,5-dichlorobenzyl.

In certain embodiments of a compound of Formula (I), $R^1$ methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is oxo, each of $R^6$ and $R^7$ is hydrogen, and $R^8$ is 3,5-dichlorobenzyl.

In certain embodiments of a compound of Formula (I): $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is oxo, each of $R^6$ and $R^7$ is hydrogen, and $R^8$ is 3,5-dichlorobenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is oxo, each of $R^6$ and $R^7$ is hydrogen, and $R^8$ is 3,5-dichlorobenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is hydrogen, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is hydrogen, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is hydrogen, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is hydrogen, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is hydrogen, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is hydrogen, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is hydrogen, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is hydrogen, each of $R^6$ and $R^7$ is hydrogen, and $R^8$ is 3-carboxybenzyl.

In certain embodiments of a compound of Formula (I), $R^1$ methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is hydrogen, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is hydrogen, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is hydrogen, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is hydrogen, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is hydroxy, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is hydroxy, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is hydroxy, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is hydroxy, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is hydroxy, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is hydroxy, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is hydroxy, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is hydroxy, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is hydroxy, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is hydroxy, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is hydroxy, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is hydroxy, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is fluoro, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is fluoro, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is fluoro, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is fluoro, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is fluoro, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is fluoro, each of $R^6$ and $R^7$ is hydrogen, and $R^5$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is fluoro, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is fluoro, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is fluoro, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is fluoro, each of $R^6$ and $R^7$ is hydrogen, and $R^2$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is fluoro, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is fluoro, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is fluoro, each of $R^6$ and $R^7$ is hydrogen, and $R^8$ is 3-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is oxo, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is oxo, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is oxo, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is oxo, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is oxo, each of $R^6$ and $R^7$ is hydrogen, and $R^8$ is 3-carboxybenzyl.

In certain embodiments of a compound of Formula (I), $R^1$ methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is oxo, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is oxo, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is oxo, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is oxo, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is oxo, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is oxo, each of $R^6$ and $R^7$ is hydrogen, and $R^8$ is 3-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is oxo, each of $R^6$ and $R^7$ is hydrogen, and $R^8$ is 3-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is hydrogen, each of $R^6$ and $R^7$ is hydrogen, and $R^8$ is 4-carboxybenzyl. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is hydrogen, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is hydrogen, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is hydrogen, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is hydrogen, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is hydrogen, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is hydrogen, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is hydrogen, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is hydrogen, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is hydrogen, each of $R^6$ and $R^7$ is hydrogen, and $R^8$ is 4-carboxybenzyl. In other embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^6$ is diethoxymethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is hydrogen, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is hydrogen, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is hydrogen, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is hydrogen, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is hydroxy, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is hydroxy, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is hydroxy, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I) $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is hydroxy, each of $R^6$ and $R^7$ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-propyl, R³ is hydrogen, R⁴ is diethoxymethyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-propyl, R³ is hydrogen, R⁴ is cyclohexylmethyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-propyl, R³ is hydrogen, R⁴ is benzyl, R⁵ is hydroxy, each of R⁶ and R⁷ is hydrogen, and R⁸ is 4-carboxybenzyl. In certain of the above embodiments of a compound of Formula (I), the carbon to which R⁵ is bonded is of the S-configuration. In certain of the above embodiments of a compound of Formula (I), the carbon to which R⁵ is bonded is of the R-configuration.

In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is ethyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is n-propyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is n-butyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is diethoxymethyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is cyclohexylmethyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isopropyl, R³ is hydrogen, R⁴ is benzyl, R⁵ is hydroxy, each of R⁶ and R⁷ is hydrogen, and R⁸ is 4-carboxybenzyl. In certain of the above embodiments of a compound of Formula (I), the carbon to which R⁵ is bonded is of the S-configuration. In certain of the above embodiments of a compound of Formula (I), the carbon to which R⁵ is bonded is of the R-configuration.

In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-butyl, R³ is hydrogen, R⁴ is ethyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-butyl, R³ is hydrogen, R⁴ is n-propyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-butyl, R³ is hydrogen, R⁴ is n-butyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-butyl, R³ is hydrogen, R⁴ is diethoxymethyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-butyl, R³ is hydrogen, R⁴ is cyclohexylmethyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is n-butyl, R³ is hydrogen, R⁴ is benzyl, R⁵ is hydroxy, each of R⁶ and R⁷ is hydrogen, and R⁸ is 4-carboxybenzyl. In certain of the above embodiments of a compound of Formula (I), the carbon to which R⁵ is bonded is of the S-configuration. In certain of the above embodiments of a compound of Formula (I), the carbon to which R⁵ is bonded is of the R-configuration.

In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isobutyl, R³ is hydrogen, R⁴ is ethyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isobutyl, R³ is hydrogen, R⁴ is n-propyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isobutyl, R³ is hydrogen, R⁴ is n-butyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isobutyl, R³ is hydrogen, R⁴ is diethoxymethyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isobutyl, R³ is hydrogen, R⁴ is cyclohexylmethyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is isobutyl, R³ is hydrogen, R⁴ is benzyl, R⁵ is hydroxy, each of R⁶ and R⁷ is hydrogen, and R⁸ is 4-carboxybenzyl. In certain of the above embodiments of a compound of Formula (I), the carbon to which R⁵ is bonded is of the S-configuration. In certain of the above embodiments of a compound of Formula (I), the carbon to which R⁵ is bonded is of the R-configuration.

In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is sec-butyl, R³ is hydrogen, R⁴ is ethyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, R² is sec-butyl, R³ is hydrogen, R⁴ is n-propyl, R⁵ is hydroxy, each of R⁶ and R⁷ is hydrogen, and R⁸ is 4-carboxybenzyl. In certain embodiments of a compound of Formula (I), R¹ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is hydroxy, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is hydroxy, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is hydroxy, each of $R^6$ and $R^7$ is hydrogen, and $R^5$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is hydroxy, each of $R^6$ and $R^7$ is hydrogen, and $R^5$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is hydroxy, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is hydroxy, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is hydroxy, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is fluoro, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is fluoro, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is fluoro, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is fluoro, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is fluoro, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is fluoro, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is fluoro, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is fluoro, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is fluoro, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is fluoro, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is fluoro, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is fluoro, each of $R^6$ and $R^7$ is hydrogen, and $R^8$ is 4-carboxybenzyl. In certain of the above embodiments of a compound of Formula (I), the carbon to which $R^5$ is bonded is of the S-configuration. In certain of the above embodiments of a compound of Formula (I), the carbon to which $R^5$ is bonded is of the R-configuration.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is ethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-propyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is n-butyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is diethoxymethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is cyclohexylmethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is hydrogen, $R^3$ is hydrogen, $R^4$ is benzyl, $R^5$ is oxo, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is ethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-propyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is n-butyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is diethoxymethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is cyclohexylmethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is methyl, $R^3$ is hydrogen, $R^4$ is benzyl, $R^5$ is oxo, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is ethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-propyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is n-butyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is diethoxymethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is cyclohexylmethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is ethyl, $R^3$ is hydrogen, $R^4$ is benzyl, $R^5$ is oxo, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is ethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-propyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is n-butyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is diethoxymethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is cyclohexylmethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-propyl, $R^3$ is hydrogen, $R^4$ is benzyl, $R^5$ is oxo, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is ethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-propyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is n-butyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is diethoxymethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is cyclohexylmethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isopropyl, $R^3$ is hydrogen, $R^4$ is benzyl, $R^5$ is oxo, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is ethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-propyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is n-butyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is diethoxymethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is cyclohexylmethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is n-butyl, $R^3$ is hydrogen, $R^4$ is benzyl, $R^5$ is oxo, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is ethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-propyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is n-butyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is diethoxymethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is cyclohexylmethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is isobutyl, $R^3$ is hydrogen, $R^4$ is benzyl, $R^5$ is oxo, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is ethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-propyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is n-butyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is diethoxymethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is cyclohexylmethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is sec-butyl, $R^3$ is hydrogen, $R^4$ is benzyl, $R^5$ is oxo, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is ethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-propyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is n-butyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is diethoxymethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is cyclohexylmethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is tert-butyl, $R^3$ is hydrogen, $R^4$ is benzyl, $R^5$ is oxo, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is ethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-propyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is n-butyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is diethoxymethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is cyclohexylmethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is phenyl, $R^3$ is hydrogen, $R^4$ is benzyl, $R^5$ is oxo, each of $R^6$ and $R^7$ is hydrogen, and $R^8$ is 4-carboxybenzyl.

In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is ethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-propyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is n-butyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is diethoxymethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is cyclohexylmethyl, $R^5$ is oxo, each of $R^6$ and $R^7$ is hydrogen, and $R^8$ is 4-carboxybenzyl. In certain embodiments of a compound of Formula (I), $R^1$ is methyl, ethyl, n-propyl, isopropyl, n-butyl, isobutyl, sec-butyl, tert-butyl, phenyl, cyclohexyl, or 3-pyridyl, $R^2$ is cyclohexyl, $R^3$ is hydrogen, $R^4$ is benzyl, $R^5$ is oxo, each of $R^6$ and $R^7$ is hydrogen, and $R^8$ is 4-carboxybenzyl.

In certain embodiments of a compound of Formula (I), the compound is chosen from:

3-{[1-isobutanoyloxyethoxy]carbonylamino}propyl(n-butyl)phosphinic acid;
3-{[benzoyloxyethoxy]carbonylamino}propyl(n-butyl)phosphinic acid;
3-{[1-isobutanoyloxymethoxy]carbonylamino}propyl(n-butyl)phosphinic acid;
3-{[benzoyloxymethoxycarbonylamino}propyl(n-butyl)phosphinic acid;
3-{[1-isobutanoyloxyisobutoxy]carbonylamino}propyl(n-butyl)phosphinic acid;
(3-{[1-cyclohexanoyloxyethoxy]carbonylamino}propyl(n-butyl)phosphinic acid;
3-{[1-isobutanoyloxyisobutoxy]carbonylamino}propyl(n-butyl)phosphinic acid sodium salt;
3-{[butanoyloxyethoxy]carbonylamino}propyl(n-butyl) phosphinic acid sodium salt;
a pharmaceutically acceptable salt of any of the foregoing, and a pharmaceutically acceptable solvate of any of the foregoing.

Synthesis

The compounds disclosed herein may be obtained via the synthetic method illustrated in Scheme 1. Those of ordinary skill in the art will appreciate that a synthetic route to the disclosed compounds consists of attaching promoieties to 3-aminopropylphosphinic acid analogs. Numerous methods have been described in the art for the synthesis of 3-aminopropylphosphinic acid analog $GABA_B$ antagonists (e.g. Froestl et al., J. Med. Chem. 1995, 38, 3313-3331; Dingwall et al., Tetrahedron 1989, 45, 3787-3808; Deprele and Montchamp, J. Org. Chem. 2001, 66, 6745-6755; Dingwall et al., U.S. Pat. No. 4,656,298; Baylis et al., U.S. Pat. No. 5,013,863; Baylis et al., U.S. Pat. No. 5,051,524; Baylis et al., U.S. Pat. No. 5,300,679; Marescaux et al., U.S. Pat. No. 5,229,379; Marescaux et al., U.S. Pat. No. 5,407,922; Mickel et al., U.S. Pat. No. 5,332,729; Mickel, U.S. Pat. No. 5,376,684; and Mickel et al., U.S. Pat. No. 5,424,441). General synthetic methods useful in the synthesis of the compounds described herein are available in the art (see, e.g., Wuts and Greene, "Protective Groups in Organic Synthesis," John Wiley & Sons, 4th ed. 2007; Harrison et al., "Compendium of Organic Synthetic Methods," Vols. 1-11, John Wiley & Sons 1971-2003; Larock "Comprehensive Organic Transformations," John Wiley & Sons, 2nd ed. 2000; and Paquette, "Encyclopedia of Reagents for Organic Synthesis," John Wiley & Sons, 11th ed. 2003). Accordingly, starting materials useful for preparing compounds and intermediates thereof, and/or practicing methods described herein are commercially available or may be prepared by well-known synthetic methods. Other methods for synthesis of the prodrugs described herein are either described in the art or will be readily apparent to the skilled artisan in view of the references provided above and may be used to synthesize the compounds described herein. Accordingly, the methods presented in the Schemes herein are illustrative rather than comprehensive.

A method for synthesis of compounds of Formula (I), illustrated in Scheme 1, relies upon reaction of a 3-aminopropylphosphinic acid analog of Formula (II) with a 1-(acyloxy)-alkyl N-hydroxysuccinimidyl carbonate compound of Formula (III), optionally in the presence of a base, as described in the co-pending application Gallop et al., International Publication No. WO 2005/066122 entitled "Synthesis of Acyloxyalkyl Carbamate Prodrugs and Intermediates Thereof," filed Dec. 30, 2004.

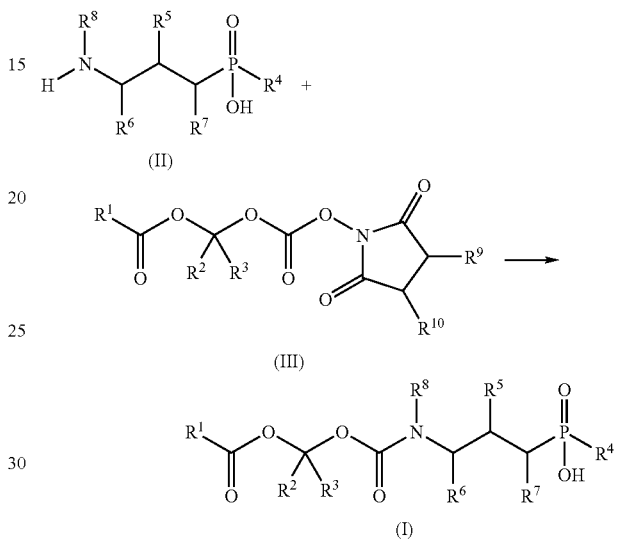

Scheme 1 wherein:

$R^9$ and $R^{10}$ is chosen from hydrogen, acylamino, acyloxy, alkoxycarbonylamino, alkoxycarbonyloxy, alkyl, substituted alkyl, alkoxy, substituted alkoxy, aryl, substituted aryl, arylalkyl, carbamoyloxy, dialkylamino, heteroaryl, hydroxy, and sulfonamido, or $R^9$ and $R^{10}$ together with the atoms to which they are bonded form a substituted cycloalkyl, substituted cycloheteroalkyl, or substituted aryl ring; and $R^1, R^2, R^3, R^4, R^5, R^6, R^7$ and $R^8$ are as previously defined.

In certain embodiments of the method described in Scheme 1 for synthesizing a compound of Formula (I), $R^2$ and $R^3$ in the compound of Formula (III) are different, such that the carbon atom to which these substituents are bonded is a stereogenic center. In certain embodiments of the method for synthesizing a compound of Formula (I), $R^2$ and $R^3$ in the compound of Formula (I) are different and the compound of Formula (I) is substantially one diastereomer.

In certain embodiments of the method described in Scheme 1 for synthesizing a compound of Formula (I), $R^9$ and $R^{10}$ in the compound of Formula (III) are each benzoyloxy, the stereochemistry at the carbon to which $R^9$ is bonded is of the R-configuration, and the stereochemistry at the carbon to which $R^{10}$ is bonded is of the R-configuration. In certain embodiments of the method described in Scheme 1 for synthesizing a compound of Formula (I), $R^9$ and $R^{10}$ in the compound of Formula (III) are each benzoyloxy, the stereochemistry at the carbon to which $R^9$ is bonded is of the S-configuration and the stereochemistry at the carbon to which $R^{10}$ is bonded is of the S-configuration.

In certain embodiments, the method of Scheme 1 is carried out in a solvent. Useful solvents include, but are not limited to, acetone, acetonitrile, dichloromethane, dichloroethane, chloroform, toluene, tetrahydrofuran, dioxane, dimethylformamide, dimethylacetamide, N-methylpyrrolidinone, dimethyl sulfoxide, pyridine, ethyl acetate, methyl tert-butyl ether, methanol, ethanol, isopropanol, tert-butanol, water, or combinations thereof. In certain embodiments, the solvent is acetone, acetonitrile, dichloromethane, toluene, tetrahydrofuran, pyridine, methyl tert-butyl ether, methanol, ethanol, isopropanol, water, or combinations thereof. In certain embodiments, the solvent is a mixture of acetonitrile and water. In certain embodiments, the solvent is a mixture of acetonitrile and water, with a volume ratio of acetonitrile to water from about 1:5 to about 5:1. In certain embodiments, the solvent is a mixture of tetrahydrofuran and water, with a volume ratio of tetrahydrofuran to water from about 20:1 to about 2:1. In certain embodiments, the solvent is a mixture of methyl tert-butyl ether and water. In certain embodiments, the solvent is a mixture of methyl tert-butyl ether and water, with a volume ratio of methyl tert-butyl ether to water from about 20:1 to about 2:1. In certain embodiments, the solvent is a mixture of methyl tert-butyl ether and water, wherein the methyl tert-butyl ether contains from about 10% to about 50% acetone by volume. In certain embodiments, the solvent is dichloromethane, water, or a combination thereof. In certain embodiments, the solvent is a biphasic mixture of dichloromethane and water. In certain embodiments, the solvent is a biphasic mixture of dichloromethane and water containing from about 0.001 equivalents to about 0.1 equivalents of a phase transfer catalyst. In certain embodiments, the phase transfer catalyst is a tetraalkylammonium salt, and in certain embodiments, the phase transfer catalyst is a tetrabutylammonium salt.

The method of Scheme 1 may be carried out at a temperature from about −20° C. to about 40° C. In certain embodiments, the temperature is from about −20° C. to about 25° C. In certain embodiments, the temperature is from about 0° C. to about 25° C. In certain embodiments, the temperature is from about 25° C. to about 40° C.

In certain embodiments of the method of Scheme 1, the reaction is performed in the absence of a base.

In other embodiments of the method of Scheme 1, the reaction is performed in the presence of an inorganic base. In certain embodiments, the reaction is performed in the presence of an alkali metal bicarbonate or alkali metal carbonate salt. In other embodiments, the reaction is performed in the presence of sodium bicarbonate.

In certain embodiments of the method of Scheme 1, the reaction is performed in the presence of an organic base. In certain embodiments, the reaction is performed in the presence of triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1, 8-diazabicyclo[5.4.0]undec-7-ene, or 1,5-diazabicyclo[4.3.0]undec-7-ene, and in certain embodiments, the reaction is performed in the presence of triethylamine, diisopropylethylamine, N-methylmorpholine, or pyridine.

Pharmaceutical Compositions

Pharmaceutical compositions comprising a therapeutically effective amount of one or more 3-aminopropylphosphinic acid analog prodrug compounds of Formula (I), in certain embodiments, in purified form, together with a suitable amount of a pharmaceutically acceptable vehicle, so as to provide a form for proper administration to a patient are provided herein. Suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, may also contain minor amounts of wetting or emulsifying agents, or pH buffering agents. In addition, auxiliary, stabilizing, thickening, lubricating, and coloring agents may be used.

Pharmaceutical compositions may be manufactured by means of conventional mixing, dissolving, granulating, dragee-making, levigating, emulsifying, encapsulating, entrapping, or lyophilizing processes. Pharmaceutical compositions may be formulated in conventional manner using one or more physiologically acceptable carriers, diluents, excipients, or auxiliaries, which facilitate processing of compounds disclosed herein into preparations, which may be used pharmaceutically. Proper formulation is dependent upon the route of administration chosen.

Pharmaceutical compositions may take the form of solutions, suspensions, emulsion, tablets, pills, pellets, capsules, capsules containing liquids, powders, sustained-release formulations, suppositories, emulsions, aerosols, sprays, suspensions, or any other form suitable for use. In certain embodiments, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995). In certain embodiments, compositions are formulated for oral delivery, particularly for oral sustained release administration.

Pharmaceutical compositions for oral delivery may be in the form of tablets, lozenges, aqueous or oily suspensions, granules, powders, emulsions, capsules, syrups, or elixirs, for example. Orally administered compositions may comprise one or more optional agents, for example, sweetening agents such as fructose, aspartame, and saccharin; flavoring agents such as peppermint, oil of wintergreen, and cherry; coloring agents; and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Oral compositions may include standard vehicles such as mannitol, lactose, starch, magnesium stearate, sodium saccharine, cellulose, magnesium carbonate, etc. Such vehicles may be of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol), oils, alcohols, slightly acidic buffers having a pH ranging from about pH 4 to about pH 6 (e.g., acetate, citrate, ascorbate at between about 5 mM to about 50 mM), etc. Additionally, flavoring agents, preservatives, coloring agents, bile salts, acylcarnitines, and the like may be added.

When the compounds of Formula (I) are acidic, they may be included in any of the above-described formulations as free acids, pharmaceutically acceptable salts, solvates, or hydrates. Pharmaceutically acceptable salts substantially retaining the activity of the free acid forms may be prepared by reaction with bases, and tend to be more soluble in aqueous and other protic solvents than the corresponding free acid forms. In certain embodiments, sodium salts of a compound of Formula (I) are used in the above described formulations.

Sustained Release Oral Dosage Forms

The disclosed compounds may be used with a number of different dosage forms, which may be adapted to provide sustained release of a compound of Formula (I) upon oral administration.

In certain embodiments, dosage forms comprise beads, which on dissolution or diffusion release a compound of Formula (I) over an extended period of hours, in certain embodiments over a period of at least about 6 hours, and in certain embodiments, over a period of at least about 8 hours and in certain embodiments, over a period of at least about 12 hours. The beads may have a central composition or core comprising a compound disclosed herein and pharmaceutically acceptable vehicles, including an optional lubricant, antioxidant, and buffer. The beads may be medical preparations with a diameter of about 0.05 mm to about 2 mm. Individual beads may comprise doses of a compound of Formula (I), for example, doses of up to about 40 mg of compound. The beads, in certain embodiments, are formed of non-cross-linked materials to enhance their discharge from the gastrointestinal tract. The beads may be coated with a release rate-controlling polymer that gives a timed-release profile.

The time-release beads may be manufactured into a tablet for therapeutically effective administration. The beads may be made into matrix tablets by the direct compression of a plurality of beads coated with, for example, an acrylic resin and blended with excipients such as hydroxypropylmethyl cellulose. The manufacture of beads is disclosed in the art (Lu, *Int. J. Pharm.* 1994, 112, 117-124; Pharmaceutical Sciences by Remington, 14$^{th}$ ed, pp. 1626-1628 (1970); Fincher, *J. Pharm. Sci.* 1968, 57, 1825-1835; and U.S. Pat. No. 4,083, 949), as has the manufacture of tablets (Pharmaceutical Sciences, by Remington, 17$^{th}$ Ed, Ch. 90, pp. 1603-1625 (1985)).

One type of sustained release oral dosage formulation that may be used with the compounds of Formula (I) comprises an inert core, such as a sugar sphere, coated with an inner drug-containing layer and an outer membrane layer controlling drug release from the inner layer. A sealcoat may be provided between the inert core and the layer containing the active ingredient. When the core is of a water-soluble or water-swellable inert material, the sealcoat may be in the form of a relatively thick layer of a water-insoluble polymer. Such a controlled release beads may thus comprise: (i) a core unit of a substantially water-soluble or water-swellable inert material; (ii) a first layer on the core unit of a substantially water-insoluble polymer; (iii) a second layer covering the first layer and containing an active ingredient; and (iv) a third layer on the second layer of polymer effective for controlled release of the active ingredient, wherein the first layer is adapted to control water penetration into the core.

In certain embodiments, the first layer (ii) above constitutes more than about 2% (w/w) of the final bead composition, such as more than about 3% (w/w), e.g., from about 3% to about 80% (w/w). The amount of the second layer (ii) above usually constitutes from about 0.05% to about 60% (w/w), such as from about 0.1% to about 30% (w/w) of the final bead composition. The amount of the third layer (iv) above usually constitutes from about 1% to about 50% (w/w), for example, from about 2% to about 25% (w/w) of the final bead composition. The core unit may have a size from about 0.05 to about 2 mm. The controlled release beads may be provided in a multiple unit formulation, such as a capsule or a tablet.

The cores may be of a water-soluble or swellable material and may be any such material that is conventionally used as cores or any other pharmaceutically acceptable water-soluble or water-swellable material made into beads or pellets. The cores may be spheres of materials such as sucrose/starch (Sugar Spheres NF), sucrose crystals, or extruded and dried spheres typically comprising excipients such as microcrystalline cellulose and lactose. The substantially water-insoluble material in the first, or sealcoat layer is generally a "GI insoluble" or "GI partially insoluble" film forming polymer (dispersed or dissolved in a solvent). Examples include, but are not limited to, ethyl cellulose, cellulose acetate, and cellulose acetate butyrate, polymethacrylates such as ethyl acrylate/methyl methacrylate copolymer (Eudragit NE-30-D), ammonio methacrylate copolymer types A and B (Eudragit RL30D and RS30D), and silicone elastomers. A plasticizer is used together with the polymer. Exemplary plasticizers include, but are not limited to, dibutylsebacate, propylene glycol, triethylcitrate, tributylcitrate, castor oil, acetylated monoglycerides, acetyl triethylcitrate, acetyl butylcitrate, diethyl phthalate, dibutyl phthalate, triacetin, and fractionated coconut oil (medium-chain triglycerides). The second layer containing the active ingredient may comprise the active ingredient with or without a polymer as a binder. The binder, when used, may be hydrophilic but may be water-soluble or water-insoluble. Examples of polymers that may be used in the second layer containing the active drug are hydrophilic polymers such as, for example, polyvinylpyrrolidone (PVP), polyalkylene glycol such as polyethylene glycol, gelatine, polyvinyl alcohol, starch, and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, and carboxymethylhydroxyethyl cellulose, acrylic acid polymers, polymethacrylates, and any other appropriate pharmaceutically acceptable polymer. The ratio of drug to hydrophilic polymer in the second layer is usually in the range of from about 1:100 to about 100:1 (w/w). Suitable polymers for use in the third layer, or membrane, for controlling the drug release may be chosen from water-insoluble polymers or polymers with pH-dependent solubility, such as, for example, ethyl cellulose, hydroxypropylmethyl cellulose phthalate, cellulose acetate phthalate, cellulose acetate trimellitate, polymethacrylates, or combinations thereof, optionally combined with plasticizers, such as those mentioned above. Optionally, a controlled release layer comprises, in addition to the polymers above, other substance(s) with different solubility characteristics, to adjust the permeability and thereby the release rate, of the controlled release layer. Examples of polymers that may be used as a modifier together with, for example, ethyl cellulose include, but are not limited to, HPMC, hydroxyethyl cellulose, hydroxypropyl cellulose, methylcellulose, carboxymethylcellulose, polyethylene glycol, polyvinylpyrrolidone (PVP), polyvinyl alcohol, polymers with pH-dependent solubility, such as cellulose acetate phthalate or ammonio methacrylate copolymer and methacrylic acid copolymer, and combinations thereof. Additives such as sucrose, lactose and pharmaceutical grade surfactants may also be included in the controlled release layer, if desired.

The preparation of the multiple unit formulation may comprise the additional step of transforming the prepared beads into a pharmaceutical formulation, such as by filling a predetermined amount of the beads into a capsule, or compressing the beads into tablets. Examples of multi-particulate sustained release oral dosage forms are described in, for example, U.S. Pat. Nos. 6,627,223 and 5,229,135.

In certain embodiments, an oral sustained release pump may be used (see Langer, supra; Sefton, *CRC Crit Ref Biomed. Eng.* 1987, 14, 201; Saudek et al., *N. Engl. J Med.* 1989, 321, 574).

In certain embodiments, polymeric materials may be used (see "Medical Applications of Controlled Release," Langer and Wise (eds.), CRC Press., Boca Raton, Fla. (1974); "Controlled Drug Bioavailability," Drug Product Design and Performance, Smolen and Ball (eds.), Wiley, New York (1984); Langer et al., *J Macromol. Sci. Rev. Macromol Chem.* 1983, 23, 61; see also Levy et al., *Science* 1985, 228, 190; During et al., *Ann. Neurol.* 1989, 25, 351; Howard et al., *J. Neurosurg.* 1989, 71, 105). In certain embodiments, polymeric materials may be used for oral sustained release delivery. Polymers include, but are not limited to, sodium carboxymethylcellulose, hydroxypropylcellulose, hydroxypropylmethylcellulose, and hydroxyethylcellulose (especially, hydroxypropylmethylcellulose). Other cellulose ethers are described (Alderman, *Int. J. Pharm. Tech. & Prod. Mfr.* 1984, 5(3), 1-9). Factors affecting drug release are well known to the skilled artisan and are described in the art (Bamba et al., *Int. J. Pharm.* 1979, 2, 307).

In certain embodiments, enteric-coated preparations may be used for oral sustained release administration. Examples of coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release), and polymers that form firm layers that are destroyed by an increase in pressure (i.e., pressure-controlled release).

In certain embodiments, drug-releasing lipid matrices may be used for oral sustained release administration. An example is solid microparticles of a compound of Formula (I) coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379,700. The lipid-coated particles may optionally be compressed to form a tablet. Another controlled release lipid-based matrix material that is suitable for sustained release oral administration comprises polyglycolized glycerides as disclosed in Roussin et al., U.S. Pat. No. 6,171,615.

In certain embodiments, waxes may be used for oral sustained release administration. Examples of suitable sustained compound-releasing waxes are disclosed in Cain et al., U.S. Pat. No. 3,402,240 (carnauba wax, candelilla wax, esparto wax, and ouricury wax); Shtohryn et al., U.S. Pat. No. 4,820,523 (hydrogenated vegetable oil, bees wax, carnauba wax, paraffin, candelilla, ozokerite, and combinations thereof); and Walters, U.S. Pat. No. 4,421,736 (combination of paraffin and castor wax).

In certain embodiments, osmotic delivery systems may be used for oral sustained release administration (Verma et al., *Drug Dev. Ind. Pharm.* 2000, 26, 695-708). In certain embodiments, OROS® systems made by Alza Corporation, Mountain View, Calif. may be used for oral sustained release delivery devices (Theeuwes et al., U.S. Pat. No. 3,845,770; Theeuwes et al., U.S. Pat. No. 3,916,899).

In certain embodiments, a controlled-release system may be placed in proximity of the target of a compound disclosed herein (e.g., within the spinal cord), thus requiring only a fraction of the systemic dose (see e.g., Goodson, in "Medical Applications of Controlled Release," supra, vol. 2, pp. 115-138 (1984)). Other controlled-release systems discussed in Langer, *Science* 1990, 249, 1527-1533, may also be used.

In certain embodiments, dosage forms comprise a compound of Formula (I) coated on a polymer substrate. The polymer may be an erodible, or a nonerodible polymer. The coated substrate may be folded onto itself to provide a bilayer polymer drug dosage form. For example, a compound disclosed of Formula (I) gelatin, polyvinyl alcohol, polyorthoester, polyacetyl, or a polyorthocarbonate and the coated polymer folded onto itself to provide a bilaminated dosage form. In operation, the bioerodible dosage form erodes at a controlled rate to dispense a compound of Formula (I) over a sustained release period. Examples of useful biodegradable polymers include biodegradable poly(amides), poly(amino acids), poly(esters), poly(lactic acid), poly(glycolic acid), poly(carbohydrate), poly(orthoester), poly (orthocarbonate), poly(acetyl), poly(anhydrides), biodegradable poly(dihydropyrans), and poly(dioxinones), which are known in the art (Rosoff, *Controlled Release of Drugs Chap.* 2, pp. 53-95 (1989); and in U.S. Pat. Nos. 3,811,444, 3,962,414, 4,066, 747, 4,070,347, 4,079,038, and 4,093,709).

In certain embodiments, dosage forms comprise a compound of Formula (I) loaded into a polymer that releases the compound by diffusion through a polymer, or by flux through pores or by rupture of a polymer matrix. Drug delivery polymeric dosage forms comprise between about 2 mg to about 500 mg of compound homogenously contained in or on a polymer. The dosage forms comprise at least one exposed surface at the beginning of dose delivery. The non-exposed surface, when present, is coated with a pharmaceutically acceptable material impermeable to the passage of a compound. The dosage forms may be manufactured by procedures known in the art. An example of providing the dosage forms comprise blending a pharmaceutically acceptable carrier like polyethylene glycol, with a known dose of a compound at an elevated temperature, (e.g., about 37° C.), and adding it to a silastic medical grade elastomer with a cross-linking agent, for example, octanoate, followed by casting in a mold. The step is repeated for each optional successive layer. The system is allowed to set for about 1 hour, to provide the dosage form. Representative polymers for manufacturing the dosage form are chosen from olefinic polymers, vinyl polymers, addition polymers, condensation polymers, carbohydrate polymer and silicone polymers such as polyethylene, polypropylene, polyvinyl acetate, polymethylacrylate, polyisobutylmethacrylate, poly alginate, polyamide, and polysilicone. The polymers and procedures for manufacturing the polymers are described in the art (Coleman et al., *Polymers* 1990, 31, 1187-1231; Roerdink et al., *Drug Carrier Systems* 1989, 9, 57-10; Leong et al., *Adv. Drug Delivery Rev.* 1987, 1, 199-233; Roff et al., *Handbook of Common Polymers* 1971, CRC Press; and U.S. Pat. No. 3,992,518).

In certain embodiments, dosage forms comprise a plurality of pills. The time-release pills provide a number of individual doses for providing various time doses for achieving a sustained-release prodrug delivery profile over an extended period of time up to about 24 hours. The matrix comprises a hydrophilic polymer chosen from, for example, a polysaccharide, agar, agarose, natural gum, alkali alginate including sodium alginate, carrageenan, fucoidan, furcellaran, laminaran, hypnea, gum arabic, gum ghatti, gum karaya, gum tragacanth, locust bean gum, pectin, amylopectin, gelatin, and a hydrophilic colloid. The hydrophilic matrix comprises a plurality of about 4 to about 50 pills, each pill comprises a dose population of from about 10 ng, about 0.5 mg, about 1 mg, about 1.2 mg, about 1.4 mg, about 1.6 mg, about 5.0 mg, etc. The pills comprise a release rate-controlling wall of about 0.001 mm up to about 10 mm thickness to provide for the timed release of a compound. Examples of wall forming materials include a triglyceryl ester chosen from glyceryl tristearate, glyceryl monostearate, glyceryl dipalmitate, glyceryl laureate, glyceryl didecenoate, and glyceryl tridenoate. Other wall forming materials include polyvinyl acetate, phthalate, methylcellulose phthalate, and microporous olefins. Procedures for manufacturing pills are disclosed in U.S. Pat. Nos. 4,434,153, 4,721,613, 4,853,229, 2,996,431, 3,139,383, and 4,752,470.

In certain embodiments, dosage forms comprise an osmotic dosage form, which comprises a semipermeable wall that surrounds a therapeutic composition comprising the compound. In use within a patient, the osmotic dosage form comprising a homogenous composition, imbibes fluid through the semipermeable wall into the dosage form in response to the concentration gradient across the semipermeable wall. The therapeutic composition in the dosage form develops osmotic pressure differential that causes the therapeutic composition to be administered through an exit from the dosage form over a prolonged period of time up to about 24 hours (or even in some cases up to about 30 hours) to provide controlled and sustained compound release. These delivery platforms may provide an essentially zero order delivery profile as opposed to the spiked profiles of immediate release formulations.

In certain embodiments, a dosage form comprises another osmotic dosage form comprising a wall surrounding a compartment, the wall comprising a semipermeable polymeric composition permeable to the passage of fluid and substantially impermeable to the passage of compound present in the compartment, a compound-containing layer composition in the compartment, a hydrogel push layer composition in the compartment comprising an osmotic formulation for imbibing and absorbing fluid for expanding in size for pushing the compound composition layer from the dosage form, and at least one passageway in the wall for releasing the prodrug composition. The method delivers the compound by imbibing fluid through the semipermeable wall at a fluid imbibing rate determined by the permeability of the semipermeable wall and the osmotic pressure across the semipermeable wall causing the push layer to expand, thereby delivering the compound from the dosage form through the exit passageway to a patient over a prolonged period of time (up to about 24 or even about 30 hours). The hydrogel layer composition may comprise about 10 mg to about 1000 mg of a hydrogel such as a member chosen from a polyalkylene oxide of about 1,000,000 to about 8,000,000 weight-average molecular weight, which are chosen from a polyethylene oxide of about 1,000,000 weight-average molecular weight, a polyethylene oxide of about 2,000,000 molecular weight, a polyethylene oxide of about 4,000,000 molecular weight, a polyethylene oxide of about 5,000,000 molecular weight, a polyethylene oxide of about 7,000,000 molecular weight, and a polypropylene oxide of the about 1,000,000 to about 8,000,000 weight-average molecular weight; or about 10 mg to about 1000 mg of an alkali carboxymethylcellulose of about 10,000 to about 6,000,000 weight average molecular weight, such as sodium carboxymethylcellulose or potassium carboxymethylcellulose. The hydrogel expansion layer comprises about 0.0 mg to about 350 mg, in present manufacture; about 0.1 mg to about 250 mg of a hydroxyalkylcellulose of about 7,500 to about 4,500,00 weight-average molecular weight (e.g., hydroxymethylcellulose, hydroxyethylcellulose, hydroxypropylcellulose, hydroxybutylcellulose, or hydroxypentylcellulose) in present manufacture; about 1 mg to about 50 mg of an agent chosen from sodium chloride, potassium chloride, potassium acid phosphate, tartaric acid, citric acid, raffinose, magnesium sulfate, magnesium chloride, urea, inositol, sucrose, glucose, and sorbitol; about 0 to about 5 mg of a colorant, such as ferric oxide; about 0 mg to about 30 mg, in a present manufacture, about 0.1 mg to about 30 mg of a hydroxypropylalkylcellulose of about 9,000 to about 225,000 average-number molecular weight, chosen from hydroxypropylethylcellulose, hydroxypropypentylcellulose, hydroxypropylmethylcellulose, and hydropropylbutylcellulose; about 0.00 to about 1.5 mg of an antioxidant chosen from ascorbic acid, butylated hydroxyanisole, butylated hydroxyquinone, butylhydroxyanisol, hydroxycoumarin, butylated hydroxytoluene, cephalm, ethyl gallate, propyl gallate, octyl gallate, lauryl gallate, propyl-hydroxybenzoate, trihydroxybutylrophenone, dimethylphenol, dibutylphenol, vitamin E, lecithin, and ethanolamine; and about 0.0 mg to about 7 mg of a lubricant chosen from calcium stearate, magnesium stearate, zinc stearate, magnesium oleate, calcium palmitate, sodium suberate, potassium laurate, salts of fatty acids, salts of alicyclic acids, salts of aromatic acids, stearic acid, oleic acid, palmitic acid, a mixture of a salt of a fatty, alicyclic, or aromatic acid, and a fatty, alicyclic, or aromatic acid.

In osmotic dosage forms, the semipermeable wall comprises a composition that is permeable to the passage of fluid and impermeable to the passage of prodrug. The wall is nontoxic and comprises a polymer chosen from a cellulose acylate, cellulose diacylate, cellulose triacylate, cellulose acetate, cellulose diacetate, and cellulose triacetate. The wall comprises about 75 wt % (weight percent) to about 100 wt % of the cellulosic wall-forming polymer or, the wall may comprise additionally about 0.01 wt % to about 80 wt % of polyethylene glycol, or about 1 wt % to about 25 wt % of a cellulose ether chosen from hydroxypropylcellulose or a hydroxypropylalkycellulose such as hydroxypropylmethylcellulose. The total weight percent of all components comprising the wall is equal to about 100 wt %. The internal compartment comprises the compound-containing composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of prodrug to a patient over time. The dosage form comprises a passageway in the wall that connects the exterior of the dosage form with the internal compartment. The osmotic powered dosage form may be made to deliver prodrug from the dosage form to the patient at a zero order rate of release over a period of up to about 24 hours.

The expression "passageway" as used herein comprises means and methods suitable for the metered release of the compound from the compartment of the dosage form. The exit means comprises at least one passageway, including orifice, bore, aperture, pore, porous element, hollow fiber, capillary tube, channel, porous overlay, or porous element that provides for the osmotic controlled release of compound. The passageway includes a material that erodes or is leached from the wall in a fluid environment of use to produce at least one controlled-release dimensioned passageway. Examples of materials suitable for forming a passageway, or a multiplicity of passageways comprise a leachable poly(glycolic) acid or poly(lactic) acid polymer in the wall, a gelatinous filament, poly(vinyl alcohol), leach-able polysaccharides, salts, and oxides. A pore passageway, or more than one pore passageway, may be formed by leaching a leachable compound, such as sorbitol, from the wall. The passageway possesses controlled-release dimensions, such as round, triangular, square and elliptical, for the metered release of prodrug from the dosage form. The dosage form may be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in U.S. Pat. Nos. 3,845,770, 3,916,899, 4,063,064, 4,088,864, and 4,816,263. Passageways formed by leaching are disclosed in U.S. Pat. Nos. 4,200,098 and 4,285,987.

Regardless of the specific form of sustained release oral dosage form used, compounds may be released from the dosage form over a period of at least about 6 hours, in certain embodiments, over a period of at least about 8 hours, and in certain embodiments, over a period of at least about 12 hours. Further, the dosage form may release from about 0 to about 30% of the prodrug in about 0 to about 2 hours, from about 20 to about 50% of the prodrug in about 2 to about 12 hours, from about 50 to about 85% of the prodrug in about 3 to about 20 hours, and greater than about 75% of the prodrug in about 5 to about 18 hours. The sustained release oral dosage form further provides a concentration of the 3-aminopropylphosphinic acid analog in the blood plasma of the patient over time, which curve has an area under the curve (AUC) that is proportional to the dose of the prodrug of the 3-aminopropylphosphinic acid analog administered, and a maximum concentration $C_{max}$. The $C_{max}$ may be less than about 75%, and in certain embodiments, less than about 60%, of the $C_{max}$ obtained from administering an equivalent dose of the compound from an immediate release oral dosage form and the AUC is substantially the same as the AUC obtained from administering an equivalent dose of the prodrug from an immediate release oral dosage form.

In certain embodiments, a pharmaceutical composition or dosage form comprising a compound of Formula (I) is capable of maintaining a therapeutically effective concentration of a compound of Formula (I) in the plasma of a patient for at least about 4 hours, in certain embodiments for at least about 8 hours, and in certain embodiments for at least about 12 hours, after the pharmaceutical composition or dosage form is orally administered to the patient. In certain embodiments, a pharmaceutical composition or dosage form comprising a compound of Formula (I) is capable of maintaining a therapeutically effective concentration of the corresponding 3-aminopropylphosphinc acid or analog thereof of a compound of Formula (I) in the plasma of a patient for at least about 4 hours, in certain embodiments for at least about 8 hours, and in certain embodiments for at least about 12 hours, after the pharmaceutical composition or dosage form is orally administered to the patient. In certain embodiments, dosage forms may be administered once, twice, three times, or four times per day.

Therapeutic Uses of Compounds and Compositions

In certain embodiments, a therapeutically effective amount of one or more compounds of Formula (I) may be administered to a patient, such as a human, suffering from cognitive or memory disorders including Mild Cognitive Impairment (MCI) and cognitive impairment associated with Alzheimer's disease. In certain embodiments, a therapeutically effective amount of one or more compounds of Formula (I) may be administered to a patient, such as a human, suffering from a mood disorder such as depression or anxiety. In certain embodiments, a therapeutically effective amount of one or more compounds of Formula (I) may be administered to a patient, such as a human, suffering from a motion disorder such as epilepsy, particularly "petit-mal" type epilepsy including spontaneous absence epilepsy and atypical absence epilepsy. In certain of the above embodiments, sustained release oral dosage forms are administered to the patients.

When used to treat the diseases or disorders disclosed herein the therapeutically effective amount of one or more compounds of Formula (I) may be administered or applied singly or in combination with other agents. The therapeutically effective amount of one or more compounds of Formula (I) may be capable of delivering a compound disclosed herein in combination with another pharmaceutically active agent, including another compound disclosed herein.

3-Aminopropylphosphinic acid analog prodrugs of Formula (I) or pharmaceutically acceptable salts or solvates thereof as disclosed herein, may be used to treat mood disorders such as depression, or more particularly, depressive disorders, for example, single episodic or recurrent major depressive disorders, dysthymic disorders, depressive neurosis and neurotic depression, melancholic depression, including anorexia, weight loss, insomnia, early morning waking and psychomotor retardation, atypical depression or reactive depression, including increased appetite, hypersomnia, psychomotor agitation or irritability, seasonal affective disorder and pediatric depression; bipolar disorders or manic depression, such as bipolar I disorder, bipolar II disorder, and cyclothymic disorder; conduct disorder and disruptive behavior disorder; anxiety disorders, such as panic disorder with or without agoraphobia, agoraphobia without history of panic disorder, specific phobias, for example, specific animal phobias, social anxiety, social phobia, obsessive-compulsive disorder, stress disorders, including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder, mood disorders associated with schizophrenia; and behavioral disturbances associated with mental retardation, autistic disorder, and conduct disorder.

3-Aminopropylphosphinic acid analog prodrugs of Formula (I) or pharmaceutically acceptable salts or solvates thereof as disclosed herein, may be used to treat delirium, dementia, and amnestic and other cognitive or neurodegenerative disorders, such as Parkinson's disease, Huntington's disease, Alzheimer's disease, senile dementia, dementia of the Alzheimer's type, memory disorders including Mild Cognitive Impairment such as occurring after a stroke, in Alzheimer's disease, in delirium, in dementia, or in schizophrenia, loss of executive function, vascular dementia, and other dementias, for example, due to HIV disease, head trauma, Parkinson's disease, Huntington's disease, Pick's disease, Friedrich's disease, Creutzfeldt-Jakob disease, or due to multiple etiologies.

3-Aminopropylphosphinic acid analog prodrugs of Formula (I) or pharmaceutically acceptable salts or solvates thereof as disclosed herein, may be used to treat movement disorders such as akinesias, dyskinesias, including familial paroxysmal dyskinesias, spasticities, Scott syndrome, hiccups, chorea and athetosis, coordination disorders such as Friedrich's ataxia and ataxia-telangiectasia, dystonia including idiopathic torsion dystonia, blepharospasm, spasmodic torticollis, spasmodic dysphonia, yips, and spasmodic torticollis, Huntington's disease, myoclonus, Parkinson's disease, supranuclear palsy, Shy-Drager syndrome, tics including Tourette's syndrome, tremor, and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremor.

3-Aminopropylphosphinic acid analog prodrugs of Formula (I) or pharmaceutically acceptable salts or solvates thereof as disclosed herein, may be used to treat chemical dependencies and addictions (e.g., dependencies on, or addictions to, alcohol, heroin, cocaine, benzodiazepines, nicotine, or phenobarbitol) and behavioral addictions such as an addiction to gambling; and ocular disorders such as glaucoma and ischemic retinopathy.

3-Aminopropylphosphinic acid analog prodrugs of Formula (I) or pharmaceutically acceptable salts or solvates thereof as disclosed herein, may be used as an anti-convulsive to treat seizures such as epileptic seizure. Methods for treating convulsions comprise administering a therapeutically effective amount of a 3-aminopropylphosphinic acid analog prodrug of Formula (I) to a patient in need of such treatment. In certain embodiments, 3-aminopropylphosphinic acid analog prodrugs of Formula (I) may be administered orally to treat convulsions and/or seizures. In certain embodiments, 3-aminopropylphosphinic acid analog prodrugs of Formula (I) may be parenterally administered to treat convulsions and/or seizures. In certain embodiments, 3-aminopropylphosphinic acid analog prodrugs of Formula (I) may be administered in amounts from about 100 mg to about 4 g daily to treat convulsions and/or seizures.

3-Aminopropylphosphinic acid analog prodrugs of Formula (I) or pharmaceutically acceptable salts or solvates thereof as disclosed herein, may be used as anti-depressants to treat mood disorders such as depression. Methods for treating depression comprise administering a therapeutically effective amount of a 3-aminopropylphosphinic acid analog prodrug of Formula (I) to a patient in need of such treatment. In certain embodiments, 3-aminopropylphosphinic acid analog prodrugs of Formula (I) may be administered orally to treat depression. In certain embodiments, 3-aminopropylphosphinic acid analog prodrugs of Formula (I) may be parenterally administered to treat depression. In certain embodiments, 3-aminopropylphosphinic acid analog prodrugs of Formula (I) may be administered in amounts from about 100 mg to about 4 g daily to treat depression.

3-Aminopropylphosphinic acid analog prodrugs of Formula (I) or pharmaceutically acceptable salts or solvates thereof as disclosed herein, may be used to treat mood disorders such as anxiety. Methods for treating anxiety comprise administering a therapeutically effective amount of 3-aminopropylphosphinic acid analog prodrugs of Formula (I) to a patient in need of such treatment. In certain embodiments, a 3-aminopropylphosphinic acid analog prodrug of Formula (I) may be administered orally to treat anxiety. In certain embodiments, 3-aminopropylphosphinic acid analog prodrugs of Formula (I) may be parenterally administered to treat anxiety. In certain embodiments, 3-aminopropylphosphinic acid analog prodrugs of Formula (I) may be administered in amounts from about 100 mg to about 4 g daily to treat anxiety.

3-Aminopropylphosphinic acid analog prodrugs of Formula (I) or pharmaceutically acceptable salts or solvates thereof as disclosed herein, may be used to treat cognitive or memory disorders such as cognitive memory impairment and/or cognitive impairment associated with Alzheimer's disease. Methods for treating cognitive memory impairment comprise administering a therapeutically effective amount of a 3-aminopropylphosphinic acid analog prodrug of Formula (I) to a patient in need of such treatment. In certain embodiments, 3-aminopropylphosphinic acid analog prodrugs of Formula (I) may be administered orally to treat cognitive memory disorders. In certain embodiments, 3-aminopropylphosphinic acid analog prodrugs of Formula (I) may be parenterally administered to treat cognitive memory disorders. In certain embodiments, 3-aminopropylphosphinic acid analog prodrugs of Formula (I) may be administered in amounts from about 100 mg to about 4 g daily to treat cognitive memory disorders.

When used to treat and diseases or disorders disclosed herein, 3-aminopropylphosphinic acid analog prodrugs of Formula (I) or pharmaceutically acceptable salts or solvates thereof as disclosed herein, may be administered or applied singly, or in combination with other agents. The compounds and/or pharmaceutical compositions comprising a compound of Formula (I) may also be administered or applied singly, or in combination with other pharmaceutically active agents.

3-Aminopropylphosphinic acid analog prodrugs of Formula (I) or pharmaceutically acceptable salts or solvates thereof as disclosed herein, and/or pharmaceutical compositions thereof may be administered orally. 3-Aminopropylphosphinic acid analog prodrugs of Formula (I) and/or pharmaceutical compositions thereof may also be administered by any other convenient route, for example, by infusion or bolus injection, by absorption through epithelial or mucocutaneous linings (e.g., oral mucosa, rectal, and intestinal mucosa, etc.). Administration may be systemic or local. Various delivery systems are known, (e.g., encapsulation in liposomes, microparticles, microcapsules, capsules, etc.) that may be used to administer a compound and/or pharmaceutical composition. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, inhalation, or topically, particularly to the ears, nose, eyes, or skin.

In certain embodiments, it may be desirable to introduce 3-aminopropylphosphinic acid analog prodrugs of Formula (I) and/or pharmaceutical compositions thereof into the central nervous system by any suitable route, including intraventricular, intrathecal, and epidural injection. Intraventricular injection may be facilitated by an intraventricular catheter, for example, attached to a reservoir, such as an Ommaya reservoir.

In certain embodiments, 3-aminopropylphosphinic acid analog prodrugs of Formula (I) and/or pharmaceutical compositions thereof may be delivered via sustained release systems, may be oral sustained release systems. In other embodiments, a pump may be used (Langer, supra; Sefton, 1987 *CRC Crit Ref Biomed Eng.* 14, 201; and Saudek et al., 1989 *N. Engl. J Med.* 321, 574).

3-Aminopropylphosphinic acid analog prodrugs of Formula (I) or pharmaceutically acceptable salts or solvates thereof as disclosed herein, and/or pharmaceutical compositions thereof may provide therapeutic or prophylactic levels of the corresponding 3-aminopropylphosphinic acid analog upon in vivo administration to a patient. The prodrug promoiety of the compounds of Formula (I) may be cleaved either chemically and/or enzymatically. One or more enzymes present in the stomach, intestinal lumen, intestinal tissue, blood, liver, brain, or any other suitable tissue of a mammal may enzymatically cleave the promoiety of the administered compounds.

The promoiety of a 3-aminopropylphosphinic acid analog prodrug of Formula (I) may be cleaved prior to absorption by the gastrointestinal tract (e.g., within the stomach or intestinal lumen) and/or after absorption by the gastrointestinal tract (e.g., in intestinal tissue, blood, liver, or other suitable tissue of a mammal). In certain embodiments, the 3-aminopropylphosphinic acid analog remains conjugated to the prodrug promoiety during transit across the intestinal mucosal barrier to provide protection from presystemic metabolism. In certain embodiments, a 3-aminopropylphosphinic acid analog prodrugs of Formula (I) is essentially not metabolized to a 3-aminopropylphosphinic acid analog within enterocytes but is metabolized to the parent drug within the systemic circulation. Cleavage of the promoiety of the 3-aminopropylphosphinic acid analog prodrugs of Formula (I) after absorption by the gastrointestinal tract may allow these prodrugs to be absorbed into the systemic circulation either by active transport, passive diffusion, or by a mixture of both active and passive processes. Accordingly, in certain embodiments, a pharmaceutical composition or dosage form of the present disclosure is capable of maintaining a therapeutically effective concentration of a 3-aminopropylphosphinic acid analog compound in the blood plasma of a patient for a period of at least about 4 hours, in certain embodiments for a period of at least about 8 hours, and in certain embodiments for a period of at least about 12 hours, after the pharmaceutical composition or dosage form comprising a corresponding 3-aminopropylphosphinic acid analog prodrug of Formula (I) is orally administered to the patient.

In certain embodiments, prodrugs of 3-aminopropylphosphinic acid analogs provided by the present disclosure can be useful in treating Alzheimer's disease and cognitive or memory disorders associated with Alzheimer's disease. Alzheimer's disease is a progressive loss of mental function characterized by degeneration of brain tissue, including loss of nerve cells and the development of senile plaques and neurofibrillary tangles. In Alzheimer's disease, parts of the brain degenerate, destroying nerve cells and reducing the responsiveness of the maintaining neurons to neurotransmitters. Abnormalities in brain tissue consist of senile or neuritic plaques, e.g., clumps of dead nerve cells containing an abnormal, insoluble protein called amyloid, and neurofibrillary tangles, twisted strands of insoluble proteins in the nerve cell.

$GABA_B$ antagonists are useful in the treatment of cognitive or memory disorders including Mild Cognitive Impairment (MCI) and cognitive impairment associated with Alzheimer's disease (see e.g., Baylis et al., U.S. Pat. No. 5,190,933; Pearlman et al., U.S. Application Publication No. 2002/0187977; Froestl et al., *Biochem. Pharmacol.* 2004, 68, 1479-1487; Helm et al., *Neuropharmacol.* 2005, 48, 956-964; Mondadori et al., *Behav. Brain Res.* 1996, 77, 227-229; Mondadori et al., *Behav. Neural Biol.* 1993, 60, 62-68; and Nakagawa et al., *Brain Res.* 1997, 766, 101-106).

The efficacy of administering a prodrug of a 3-aminopropylphosphinic acid analog provided by the present disclosure for treating Alzheimer's disease may be assessed using animal and human models of Alzheimer's disease and clinical studies. Useful animal models for assessing the efficacy of compounds for treating Alzheimer's disease are disclosed, for example, in Van Dam and De Dyn, *Nature Revs Drug Disc* 2006, 5, 956-970; Simpkins et al., *Ann N Y Acad Sci,* 2005, 1052, 233-242; Higgins and Jacobsen, *Behav Pharmacol* 2003, 14(5-6), 419-38; Janus and Westaway, *Physiol Behav* 2001, 73(5), 873-86; Bardgett et al., *Brain Res Bull* 2003, 60, 131-142; and Conn, ed., "Handbook of Models in Human Aging," 2006, Elsevier Science & Technology.

In certain embodiments, compounds prodrugs of 3-aminopropylphosphinic acid analogs provided by the present disclosure and pharmaceutical compositions thereof can be used to treat a mood disorder such as, for example, a bipolar disorder and a depressive disorder.

Bipolar disorder is a psychiatric condition characterized by periods of extreme mood. The moods can occur on a spectrum ranging from depression (e.g., persistent feelings of sadness, anxiety, built, anger, isolation, and/or hopelessness, disturbances in sleep and appetite, fatigue and loss of interest in usually enjoyed activities, problems concentrating, loneliness, self-loathing, apathy or indifference, depersonalization, loss of interest in sexual activity, shyness or social anxiety, irritability, chronic pain, lack of motivation, and morbid/suicidal ideation) to mania (e.g., elation, euphoria, irritation, and/or suspicious). Bipolar disorder is defined and classified in DSM-IV-TR. Bipolar disorder includes bipolar I disorder, bipolar II disorder, cyclothymia, and bipolar disorder not otherwise specified. Bipolar disorder is a common, severe, chronic and one of the most debilitating of all medical illnesses. Patients afflicted with this disorder typically alternate between episodes of depression (depressed mood, hopelessness, anhedonia, varying sleep disturbances, difficulty in concentration, psychomotor retardation and often, suicidal ideation) and episodes of mania (grandiosity, euphoria, racing thoughts, decreased need for sleep, increased energy, risk taking behavior).

Treatment of bipolar disorder can be assessed in clinical trials using rating scales such as the Montgomery-Asberg Depression Rating Scale, the Hamilton Depression Scale, the Raskin Depression Scale, Feighner criteria, and/or Clinical Global Impression Scale Score (Gijsman et al., *Am J Psychiatry* 2004, 161, 1537-1547; and Post et al., *J Clin Psychiatry* 2005, 66(3), 370-374).

Depressive disorders include major depressive disorder, dysthymic disorder, premenstrual dysphoric disorder, minor depressive disorder, recurrent brief depressive disorder, and postpsychotic depressive disorder of schizophrenia (see DSM IV).

$GABA_B$ antagonists are also useful in the treatment of depressive moods or anxiety states (see e.g., Slattery et al., *J. Pharmacol. Exp. Ther.* 2005, 312, 290-296; and Nakagawa et al., *Eur. J. Pharmacol.* 1999, 381, 1-7).

The efficacy of compounds provided by the present disclosure for treating depression can be evaluated in animal models of depression such as the forced swim test (Porsolt et al., *Nature* 1977, 266, 525-532; and Porsolt et al., *Arch Int Pharmacodyn* 1997, 229, 327-336), the tail suspension test (Cryan et al., *Trends Pharmacol Sci* 2002, 23, 238-245; and Cryan and Mombereau, *Mol Psychiatr* 2004, 9, 1050-1062), and well as other (Porsolt, *Rev. Neurosci* 2000, 11, 53-58).

In certain embodiments, prodrugs of 3-aminopropylphosphinic acid analogs provided by the present disclosure can be useful in treating anxiety. Anxiety is defined and classified in DSM-IV-TR. Anxiety disorders include panic attack, agoraphobia, panic disorder without agoraphobia, agoraphobia without history of panic disorder, specific phobia, social phobia, obsessive-compulsive disorder, posttraumatic stress disorder, acute stress disorder, generalized anxiety disorder, anxiety disorder due to a general medical condition, substance-induced anxiety disorder, and anxiety disorder not otherwise specified.

Useful animal models for assessing treatment of anxiety include fear-potentiated startle (Brown et al., *J Experimental*

*Psychol* 1951, 41, 317-327); elevated plus-maze (Pellow et al., *J Neurosci. Methods* 1985, 14, 149-167; and Hogg, *Pharmacol Biochem Behavior* 1996, 54(1), 21-20); fear-potentiated behavior in the elevated plus-maze test (Korte and De Boer, *Eur J Pharmacol* 2003, 463, 163-175); X-maze test of anxiety (Handley and Mithani, *Arch Pharmacol* 1984, 327, 1-5); and rat social interaction test (File, *J Neurosci Methods* 1980, 2, 219-238). Genetic animal models of anxiety are known (Toh, *Eur J Pharmacol* 2003, 463, 177-184) as are other animal models sensitive to anti-anxiety agents (Martin, *Acta Psychiatr Scand* 1998, Suppl 393, 74-80).

In clinical trials, efficacy can be evaluated using psychological procedures for inducing experimental anxiety applied to healthy volunteers and patients with anxiety disorders (see e.g., Graeff, et al., *Brazilian J Medical Biological Res* 2003, 36, 421-32) or by selecting patients based on the Structured Clinical interview for DSM-IV Axis I Disorders as described by First et al., Structured Clinical Interview for DSM-IV Axis I Disorders, Patient Edition (SCIDIP), Version 2. Biometrics Research, New York State Psychiatric Institute, New York, 1995. One or more scales can be used to evaluate anxiety and the efficacy of treatment including, for example, the Penn State Worry Questionnaire (Behar et al., *J Behav Ther Exp Psychiatry* 2003, 34, 25-43), the Hamilton Anxiety and Depression Scales, the Spielberger State-Trait Anxiety Inventory, and the Liebowitz Social Anxiety Scale (Hamilton, *J Clin Psychiatry* 1980, 41, 21-24; Spielberger and Vagg, *J Personality Assess* 1984, 48, 95-97; and Liebowitz, *J Clin Psychiatry* 1993, 51, 31-35 (Suppl)).

In certain embodiments, prodrugs of 3-aminopropylphosphinic acid analogs provided by the present disclosure can be useful in treating seizure disorders such as epilepsy. Seizure disorders such as epilepsy involve periodic disturbances of the brain's electrical activity, resulting in some degree of temporary brain dysfunction. Seizures can be localized (partial or focal onset seizures) or distributed (generalized seizures). Partial seizures can be simple, in which a person is completely conscious and aware of the surroundings, or complex, in which consciousness is impaired but not completely lost. Partial seizures include simple partial seizures, Jacksonian seizures, complex partial seizures, and epilepsia partialis continua. Generalized seizures cause a loss of consciousness and abnormal movements. Generalized seizures include tonic-clonic seizures, primary generalized epilepsy, bsence seizures, atonic seizures, myoclonic seizures, and status epilepticus.

$GABA_B$ antagonists are also useful in the treatment of epilepsy, particularly "petit-mal" type epilepsy, including spontaneous absence epilepsy and atypical absence epilepsy (see e.g., Marescaux et al., U.S. Pat. No. 5,407,922; Marescaux et al., U.S. Pat. No. 5,545,631; Czuczwar and Patsalos, *CNS Drugs,* 2001, 15, 339-350; Getova et al., *Eur. J. Pharmacol.* 1997, 320, 9-13; Vergnes et al., *Eur. J. Pharmacol.* 1997, 332, 245-255; and Marescaux et al., *J. Neural Transm.* 1992, 35, 179-188).

Animal models that are useful for evaluating the efficacy of compounds for treating seizure disorders are known (see, e.g., Murashima et al, *Epilepsia* 2002, 43(Suppl. 5), 130-135; and Kudin et al., *Eur J Neurosci* 2002, 15, 1105-14)).

Doses

3-Aminopropylphosphinic acid analog prodrugs of Formula (I) may be administered to treat diseases or disorders such as mild cognitive impairment, cognitive impairment associated with Alzheimer's disease, depression, anxiety, epilepsy, and others disclosed herein.

The amount of 3-aminopropylphosphinic acid analog prodrugs of Formula (I) that will be effective in the treatment of a particular disorder or condition disclosed herein will depend on the nature of the disorder or condition, and may be determined by standard clinical techniques known in the art. In addition, in vitro or in vivo assays may optionally be employed to help identify optimal dosage ranges. The amount of a compound administered will, of course, be dependent on, among other factors, the subject being treated, the weight of the subject, the severity of the affliction, the manner of administration, and the judgment of the prescribing physician.

In certain embodiments, the dosage forms are adapted to be administered to a patient no more than twice per day, and in certain embodiments, only once per day. Dosing may be provided alone or in combination with other drugs and may continue as long as required for effective treatment of the disease state or disorder.

Suitable dosage ranges for oral administration are dependent on the potency of the parent 3-aminopropylphosphinic acid analog. For certain 3-aminopropylphosphinic acid analogs, doses are generally between about 0.1 mg to about 20 mg per kilogram body weight. Other 3-aminopropylphosphinic acid analogs may be more potent and lower doses may be appropriate for both the parent drug and any prodrug (measured on an equivalent molar basis). Dosage ranges may be readily determined by methods known to the skilled artisan.

Combination Therapy

In certain embodiments, 3-aminopropylphosphinic acid analog prodrugs of Formula (I) or pharmaceutically acceptable salts or solvates thereof as disclosed herein, may be used in combination therapy with at least one other therapeutic agent. 3-Aminopropylphosphinic acid analog prodrugs of Formula (I) and the other therapeutic agent(s) may act additively or, and in certain embodiments, synergistically. In certain embodiments, a 3-aminopropylphosphinic acid analog prodrug of Formula (I) may be administered concurrently with the administration of another therapeutic agent, such as for example, an anti-depressant, anxiolytic, sedative, non-steroidal anti-inflammatory drug, selective serotonin reuptake inhibitor, monoamine oxidase inhibitor, psychostimulant, antipsychotic, anticonvulsant, or sedative. In certain embodiments, a 3-aminopropylphosphinic acid analog prodrug of Formula (I) or pharmaceutically acceptable salts or solvates thereof may be administered prior or subsequent to administration of another therapeutic agent, such as for example, an antidepressant, anxiolytic, sedative, non-steroidal anti-inflammatory drug, selective serotonin reuptake inhibitor, monoamine oxidase inhibitor, psychostimulant, antipsychotic, or anticonvulsant.

Pharmaceutical compositions of the present disclosure may include, in addition to one or more compounds of the present disclosure, one or more therapeutic agents effective for treating the same or different disease, disorder, or condition.

Methods of the present disclosure include administration of one or more compounds or pharmaceutical compositions of the present disclosure and one or more other therapeutic agents provided that the combined administration does not inhibit the therapeutic efficacy of the one or more compounds of the present disclosure and/or does not produce adverse combination effects.

In certain embodiments, compositions of the present disclosure may be administered concurrently with the administration of another therapeutic agent, which may be part of the same pharmaceutical composition as, or in a different composition from, that containing the compounds of the present disclosure. In certain embodiments, compounds of the present disclosure may be administered prior or subsequent to administration of another therapeutic agent. In certain embodiments of combination therapy, the combination therapy comprises alternating between administering a composition of the present disclosure and a composition comprising another therapeutic agent, e.g., to minimize adverse side effects associated with a particular drug. When a compound of the present disclosure is administered concurrently with another therapeutic agent that potentially may produce adverse side effects including, but not limited to, toxicity, the therapeutic agent may advantageously be administered at a dose that falls below the threshold at which the adverse side effect is elicited.

In certain embodiments, a drug may further comprise substances to enhance, modulate and/or control release, bioavailability, therapeutic efficacy, therapeutic potency, stability, and the like. For example, to enhance therapeutic efficacy a drug may be co-administered with one or more active agents to increase the absorption or diffusion of the drug from the gastrointestinal tract, or to inhibit degradation of the drug in the systemic circulation. In certain embodiments, a drug may be co-administered with active agents having pharmacological effects that enhance the therapeutic efficacy of the drug.

In certain embodiments, compounds or pharmaceutical compositions of the present disclosure include, or may be administered to a patient together with, another compound for treating anxiety, drugs for treating seizure disorders such as epilepsy, drugs for treating cognitive or memory disorders, or drugs for treating depression.

Examples of drugs for treating mood disorders such as anxiety include benzodiazepines such as alprazolam, chlordiazepoxide, clonazepam, clorazepate, diazepam, lorazepam, and oxazepam; antidepressants including tricyclic antidepressants such as amitriptyline, amoxapine, clomipramine, desipramine, doxepin, imipramine, maprotiline, nortriptyline, protriptyline, and trimipramine, selective serotonin reuptake inhibitors such as citalopram, fluoxetine, fluvoxamine, paroxetine, and sertraline; monoamine oxidase inhibitors such as phenelzine and tranylcypromine, and other antidepressants such as bupropion, mirtazapine, nefazodone, trazodone, and venlafaxine; and other anxiolytics such as hydroxyzine, mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, captodiamine, capuride, carbcloral, carbromal, chloralbetaine, enciprazine, flesinoxan, ipsapiraone, lesopitron, loxapine, methaqualone, methprylon, propanolol, tandospirone, trazadone, zopiclone, and zolpidem.

Examples of drugs for treating mood disorders such as depression include tricyclic antidepressants such as amitriptyline, amoxapine, clomipramine, desipramine, doxepin, imipramine, maprotiline, nortriptyline, protriptyline, and trimipramine; selective serotonin reuptake inhibitors such as citalopram, escitalopram, fluoxetine, fluvoxamine, paroxetine, and sertraline; serotonin-noradrenaline reuptake inhibitors such as venlafaxine, duloxetine, sibutramine, and milnacipran; monoamine oxidase inhibitors such as phenelzine and tranylcypromine; and psychostimulants such as dextroamphetamine and methylphenidate. Other antidepressants include benmoxine, butriptyline, dosulepin, imipramine, kitanserin, lofepramine, medifoxamine, mianserin, mirtazapine, viloxazine, cotinine, nisoxetine, reboxetine, tianeptine, acetaphenazine, binedaline, brofaromine, cericlamine, clovoxamine, iproniazid, isocarboxazid, moclobemide, phenyhydrazine, selegiline, sibutramine, ademetionine, adrafinil, amesergide, amisulpride, amperozide, benactyzine, bupropion, caroxazone, gepirone, idazoxan, metralindole, minaprine, nefazodone, nomifensine, ritanserin, roxindole, S-adenosylmethionine, escitalopram, tofenacin, trazodone, tryptophan, zalospirone, and Saint John's wort. Compounds and compositions of the present disclosure may also be used in conjunction with psychotherapy or electroconvulsive therapy to treat mood disorders such as depression.

Examples of drugs for treating seizures such as epilepsy include anticonvulsants such as carbamazepine, clonazepam, divalproex, ethosuximide, felbamate, fosphenyloin, gabapentin, lamotrigine, levetiracetam, lorazepam, midazolam, oxcarbazepine, phenobarbital, phenyloin, primidone, tiagabine, topiramate, valproic acid, vigabatrin, and zonisamide; and sedatives such as diazepam and lorazepam.

Examples of drugs for treating cognitive or memory disorders include antipsychotic drugs such as chlorpromazine, fluphenazine, haloperidol, loxapine, mesoridazine, molindone, perphenazine, pimozide, thioridazine, thiothixene, trifluoperazine, aripiprazole, clozapine, olanzapine, quetiapine, risperidone, and ziprasidone; sedatives such as diazepam and lorazepam; benzodiazepines such as alprazolam, chlordiazepoxide, clonazepam, clorazepate, diazepam, lorazepam, and oxazepam; nonsteroidal anti-inflammatory drugs such as aceclofenac, acetaminophen, alminoprofen, amfenac, aminopropylon, amixetrine, aspirin, benoxaprofen, bromfenac, bufexamac, carprofen, celecoxib, choline, salicylate, cinchophen, cinmetacin, clopriac, clometacin, diclofenac, diflunisal, etodolac, fenoprofen, flurbiprofen, ibuprofen, indomethacin, indoprofen, ketoprofen, ketorolac, mazipredone, meclofenamate, nabumetone, naproxen, parecoxib, piroxicam, pirprofen, rofecoxib, sulindac, tolfenamate, tolmetin, and valdecoxib; acetylcholinesterase inhibitors such as donepezil, galantamine, rivastigmine, physostigmine, and tacrine; or N-methyl-D-aspartate (NMDA) receptor blockers such as memantine.

EXAMPLES

The following examples describe in detail preparation of compounds disclosed herein. It will be apparent to those of ordinary skill in the art that many modifications, both to materials and methods, may be practiced.

In the examples below, the following abbreviations have the following meanings. If an abbreviation is not defined, it has its generally accepted meaning.

Atm=atmosphere
Boc=tert-butyloxycarbonyl
Cbz=carbobenzyloxy
DCC=dicyclohexylcarbodiimide
DMAP=4-N,N-dimethylaminopyridine
DMF=N,N-dimethylformamide
DMSO=dimethylsulfoxide
g=gram
h=hour
HPLC=high pressure liquid chromatography
L=liter
LC/MS=liquid chromatography/mass spectroscopy
M=molar
min=minute
mL=milliliter
mmol=millimoles
NHS=N-hydroxysuccinimide
THF=tetrahydrofuran
TFA=trifluoroacetic acid TLC=thin layer chromatography
TMS=trimethylsilyl
μL=microliter
μM=micromolar
v/v=volume to volume Synthesis of Chemical Intermediates Useful in Synthesizing Acyloxyalkyl Carbamate Prodrugs of 3-Aminopropylphosphinic Acid O-(1-Isobutanoyloxyethyl) S-methyl thiocarbonate (2) was synthesized using a two-step process. In a first step (Step A), a 21% (w/w) aqueous solution of sodium methylthiolate (580.7 g, 1.74 mol) was added to a solution of 1-chloroethyl chloroformate (250 g, 1.74 mol) and tetrabutylammonium hydrogensulfate (5.9 g, 17 mmol) in $CH_2Cl_2$ (450 mL) over 2 h. The reaction mixture was stirred for an additional hour, then worked-up by separating the aqueous phase and extracting the organic phase with brine (2×250 mL). The organic phase was dried over anhydrous sodium sulfate and concentrated in vacuo. The residue was purified by vacuum distillation to afford O-(1-chloroethyl) S-methyl thiocarbonate (3) as a colorless liquid (277.3 g, 97% yield). $^1$H NMR ($CDCl_3$, 400 MHz): δ 1.82 (d, J=5.6 Hz, 3H), 2.38 (s, 3H), 6.57 (q, J=5.2 Hz, 1H).

In a second step (Step B), compound (3) (308 g, 2 mol) was dissolved in isobutyric acid (264 g, 3 mol). This mixture was slowly added to a pre-mixed solution of isobutyric acid (264 g, 3 mol) and diisopropylethylamine (387 g, 3 mol), and the reaction mixture heated to 55° C. for 16 h, diluted with ether (10 L), washed with water (4×5 L), saturated bicarbonate solution (2×5 L) and brine (5 L), then dried over anhydrous sodium sulfate, filtered, and concentrated in vacuo to give compound (2) as a colorless liquid (400 g, 97% yield). The product was optionally further purified by vacuum distillation (135° C./20 Torr). $^1$H NMR ($CDCl_3$, 400 MHz): δ 1.17 (d, J=6.8 Hz, 6H), 1.49 (d, J=5.6 Hz, 3H), 2.33 (s, 3H), 2.54 (m, 1H), 6.91 (q, J=5.2 Hz, 1H).

Following the procedures for synthesizing O-(1-isobutanoyloxyethyl) S-methyl thiocarbonate (2) and replacing isobutyric acid with n-butyric acid in Step B affords O-(1-butanoyloxyethyl) S-methyl thiocarbonate (4) as an oil.

Following the procedures for synthesizing O-(1-isobutanoyloxyethyl) S-methyl thiocarbonate (2) and replacing isobutyric acid with pivalic acid in Step B affords O-(1-pivaloyloxyethyl) S-methyl thiocarbonate (5) as an oil.

Following the procedures for synthesizing O-(1-isobutanoyloxyethyl) S-methyl thiocarbonate (2) and replacing isobutyric acid with cyclohexanecarboxylic acid in Step B affords O-(cyclohexylethyl) S-methyl thiocarbonate (6) as an oil.

Following the procedures for synthesizing O-(1-isobutanoyloxyethyl) S-methyl thiocarbonate (2) and replacing isobutyric acid with benzoic acid in Step B affords O-(benzoyloxyethyl) S-methyl thiocarbonate (215) as an oil.

Following the procedures for synthesizing O-(1-isobutanoyloxyethyl) S-methyl thiocarbonate (2) and replacing 1-chloroethyl chloroformate with chloromethyl chloroformate in Step A affords O-(isobutanoyloxymethyl) S-methyl thiocarbonate (7) as an oil.

Following the procedures for synthesizing O-(1-isobutanoyloxyethyl) S-methyl thiocarbonate (2) and replacing 1-chloroethyl chloroformate with chloromethyl chloroformate in Step A and replacing isobutyric acid with n-butyric acid in Step B affords O-(butanoyloxymethyl) S-methyl thiocarbonate (8) as an oil.

Following the procedures for synthesizing O-(1-isobutanoyloxyethyl) S-methyl thiocarbonate (2) and replacing 1-chloroethyl chloroformate with chloromethyl chloroformate in Step A and replacing isobutyric acid with pivalic acid in Step B affords O-(pivaloyloxymethyl) S-methyl thiocarbonate (9) as an oil.

Following the procedures for synthesizing O-(1-isobutanoyloxyethyl) S-methyl thiocarbonate (2) and replacing 1-chloroethyl chloroformate with chloromethyl chloroformate in Step A and replacing isobutyric acid with cyclohexanecarboxylic acid in Step B affords O-(cyclohexanoyloxymethyl) S-methyl thiocarbonate (10) as an oil.

Following the procedures for synthesizing O-(1-isobutanoyloxyethyl) S-methyl thiocarbonate (2) and replacing 1-chloroethyl chloroformate with chloromethyl chloroformate in Step A and replacing isobutyric acid with benzoic acid in Step B affords O-(benzoyloxymethyl) S-methyl thiocarbonate (213) as an oil.

O-(1-Isobutanoyloxyisobutoxy) S-methyl thiocarbonate (11) was synthesized in a three-step process. In a first step (Step A), a solution of 1-chloro-2-methylpropyl chloroformate (1026 g, 6.0 mol) and tetrabutylammonium hydrogensulfate (20 g, 60 mmol) in dichloromethane (1500 mL) in a jacketed 10 L reactor equipped with a mechanical stirrer, temperature probe, and addition funnel was cooled to 10° C. To the reaction mixture was gradually added a 15% aqueous solution of sodium methylthiolate (3 L, 6.4 mol) over 4 h. The reaction was moderately exothermic and the internal temperature was maintained between 10 and 20° C. during the addition. The aqueous phase was separated and the organic phase was washed with brine (2×2 L) and water (2 L). The organic layer was dried over anhydrous $Na_2SO_4$, filtered, and concentrated under reduced pressure to afford O-(1-chloroisobutoxy) S-methyl thiocarbonate (12) (1050 g, 5.76 mol, 96% yield) as a colorless liquid. $^1$H NMR ($CDCl_3$, 400 MHz): δ 1.1 (dd, 6H), 2.2 (m, 1H), 2.4 (s, 3H), 6.35 (d, 1H).

In a second step (Step B), to a 20 L round bottom flask was added isobutyric acid (1300 mL, 14 mol), and an aqueous solution of 25% tetramethylammonium hydroxide (5 L, 14 mol). The water was removed under reduced pressure, and azeotroped with toluene (2×2 L) to leave tetramethylammonium isobutyrate (13) as an amber liquid, which was used without further purification.

In a third step (Step C), to a 3 L three neck round bottom flask equipped with a mechanical stirrer and Teflon-coated thermocouple was added compound (13) (1672 g, 9 mol), isobutyric acid (264 g, 1.5 mol), and compound (12) (1050 g, 5.76 mol). The reaction mixture was heated to 80° C. for 12 h, monitoring the reaction progress by $^1$H NMR. The reaction mixture was cooled to 20° C., diluted with EtOAc (1 L) and washed with water (2×1 L), saturated $NaHCO_3$ (1×2 L) and water (1 L). The organic phase was separated and concentrated under reduced pressure to afford O-(1-isobutanoyloxyisobutoxy) S-methyl thiocarbonate (11) (905 g, 3.9 mol, 65%) as a colorless liquid. $^1$H NMR ($CDCl_3$, 400 MHz): δ 1.0 (d, 6H), 1.2 (dd, 6H), 2.05 (m, 1H), 2.35 (s, 3H), 2.6 (m, 1H), 6.7 (d, 1H).

Following the procedures for synthesizing O-(1-isobutanoyloxyisobutoxy) S-methyl thiocarbonate (11) and replacing isobutyric acid with n-butyric acid affords O-(1-butanoyloxyisobutoxy) S-methyl thiocarbonate (14) as an oil.

Following the procedures for synthesizing O-(1-isobutanoyloxyisobutoxy) S-methyl thiocarbonate (11) and replacing isobutyric acid with pivalic acid affords O-(1-pivaloyloxyisobutoxy) S-methyl thiocarbonate (15) as an oil.

Following the procedures for synthesizing O-(1-isobutanoyloxyisobutoxy) S-methyl thiocarbonate (11) and replacing isobutyric acid with cyclohexanecarboxylic acid affords O-(1-cyclohexanoyloxyisobutoxy) S-methyl thiocarbonate (16) as an oil.

[(1-Isobutanoyloxyethoxy)carbonyloxy]succinimide (17) was synthesized using the following procedure. To a solution of compound (2) (1 g, 4.8 mmol) in $CH_2Cl_2$ (10 mL) was added N-hydroxysuccinimide (1.1 g, 9.5 mmol) and the reaction mixture cooled to 0° C. A solution of 32% (v/v) peracetic acid in acetic acid (3.4 mL, 1.1 g, 14.4 mmol) was added dropwise over a period of 10 min, then the solution allowed to stir at room temperature for 3 h. The reaction mixture was diluted with ether (50 mL) and washed with water (2×10 mL), saturated sodium bicarbonate solution (10 mL) and brine (10 mL), then dried over anhydrous sodium sulfate, filtered, and concentrated in vacuo to give compound (17) as a as colorless oil (1 g, 77% yield). After trituration with hexane (20 mL) the product solidified to a white solid. m.p: 50-54° C. $^1$H NMR ($CDCl_3$, 400 MHz): δ 1.17 (d, J=6.8 Hz, 6H), 1.56 (d, J=5.6 Hz, 3H), 2.55 (m, 1H), 2.82 (s, 4H), 6.80 (q, J=5.2 Hz, 1H). MS (ESI) m/z 296.4 (M+Na)$^+$.

Following the procedures for synthesizing

[(1-isobutanoyloxyethoxy)carbonyloxy]succinimide (17) and replacing compound (2) with compound (4) affords [(1-butanoyloxyethoxy)carbonyloxy]succinimide (18).

Following the procedures for synthesizing

[(1-isobutanoyloxyethoxy)carbonyloxy]succinimide (17) and replacing compound (2) with compound (5) affords [(1-pivaloyloxyethoxy)carbonyloxy]succinimide (19).

Following the procedures for synthesizing

[(1-isobutanoyloxyethoxy)carbonyloxy]succinimide (17) and replacing compound (2) with compound (6) affords [(1-cyclohexanoyloxyethoxy)carbonyloxy]succinimide (20).

Following the procedures for synthesizing

[(1-isobutanoyloxyethoxy)carbonyloxy]succinimide (17) and replacing compound (2) with compound (215) affords [(1-benzoyloxyethoxy)carbonyloxy]succinimide (216).

Following the procedures for synthesizing

[(1-isobutanoyloxyethoxy)carbonyloxy]succinimide (17) and replacing compound (2) with compound (7) affords [(isobutanoyloxymethoxy)carbonyloxy]succinimide (21).

Following the procedures for synthesizing

[(1-isobutanoyloxyethoxy)carbonyloxy]succinimide (17) and replacing compound (2) with compound (8) affords [(butanoyloxymethoxy)carbonyloxy]succinimide (22).

Following the procedures for synthesizing

[(1-isobutanoyloxyethoxy)carbonyloxy]succinimide (17) and replacing compound (2) with compound (9) affords [(pivaloyloxymethoxy)carbonyloxy]succinimide (23).

Following the procedures for synthesizing

[(1-isobutanoyloxyethoxy)carbonyloxy]succinimide (17) and replacing compound (2) with compound (10) affords [(cyclohexanoyloxymethoxy)carbonyloxy]succinimide (24).

Following the procedures for synthesizing

[(1-isobutanoyloxyethoxy)carbonyloxy]succinimide (17) and replacing compound (2) with compound (213) affords [(benzoyloxymethoxy)carbonyloxy]succinimide (214).

(1R)-1-[((3S,4S)-2,5-Dioxo-3,4-dibenzoyloxypyrrolidinyl)-oxycarbonyloxy]-2-methylpropyl 2-methylpropanoate (25) was synthesized in a three-step process. In a first step (Step A), a suspension of 2,3-dibenzoyl-D-tartaric acid (100 g, 279 mmol) in acetic anhydride (300 mL) was stirred at 85° C. for 2 h then the reaction mixture allowed to cool to room temperature. The crystalline product was collected by filtration, washed with a mixture of ether and hexane (1:1) and dried under vacuum to afford (3S,4S)-2,5-dioxo-3,4-dibenzoyloxy-3,4-dihydrofuran (26) (80 g, 84% yield). $^1$H NMR ($CDCl_3$, 400 MHz): δ 5.99 (s, 2H), 7.50 (m, 4H), 7.66 (m, 2H), 8.07 (m, 4H).

In a second step (Step B), to a suspension of (26) (60 g, 176 mmol) in a mixture of acetonitrile and water (8:1, 400 mL) at 0° C. was added a 50% aqueous solution of hydroxylamine (13.0 mL, 211 mmol). The resulting suspension was stirred overnight at room temperature to obtain a clear solution. The bulk of the acetonitrile was removed by rotary evaporation and the residue was portioned between ethyl acetate and water. The organic phase was washed successively with water and brine, dried over anhydrous $Na_2SO_4$ and concentrated in vacuo to afford the intermediate, 2,3-dibenzoyloxy D-tartaric acid mono-hydroxamate. This compound was suspended in toluene heated under reflux for 2 h, then cooled to room temperature to form a crystalline solid. The product was collected by filtration, washed with a mixture of ether and hexane (1:1), and dried under vacuum to afford 1-hydroxy-(3S,4S)-2,5-dioxo-3,4-dibenzoyloxypyrrolidine (27) (58 g, 93%). $^1$H NMR ($CDCl_3$, 400 MHz): δ 6.06 (s, 2H), 7.50 (t, 4H), 7.65 (dt, 2H), 8.06 (m, 4H). MS (ESI) m/z 354.00 (M−H)$^-$.

In a third step (Step C), to a stirred solution of compound (27) (35 g, 98.6 mmol) and thiocarbonate (11) (34.6 g, 148 mmol) in dichloromethane at 0° C. was dropwise added a 32% solution of peracetic acid (300 mmol) in acetic acid over 2 h. The reaction temperature was kept below 35° C. during the addition of peracetic acid. After the addition was complete, the reaction mixture was stirred overnight at room temperature. The resulting white precipitate was filtered and washed successively with water, and a mixture of ether and hexane (1:2), then dried under vacuum to afford the crude title compound. This product was crystallized once from a mixture of ethyl acetate and hexane (1:1) to afford (1R)-1-[((3S,4S)-2,5-dioxo-3,4-dibenzoyloxypyrrolidinyl)-oxycarbonyloxy]-2-methylpropyl 2-methylpropanoate (25) (13.7 g, 25% yield). The diastereomeric purity of the product was determined to be 98.4% d.e. by HPLC using a chiral column. $^1$H NMR ($CDCl_3$, 400 MHz): δ 1.06 (d, 6H), 1.22 (d, 3H), 1.22 (d, 3H), 2.20 (m, 1H), 2.64 (hept. 1H), 6.01 (br. s, 2H), 6.64 (d, 1H), 7.47 (m, 4H), 7.63 (m, 2H), 8.07 (m, 4H).

(1S)-1-[((3R,4R)-2,5-Dioxo-3,4-dibenzoyloxypyrrolidinyl)-oxycarbonyloxy]-2-methylpropyl 2-methylpropanoate (28) was synthesized using a three-step process. In a first step (Step A), to a 3-necked 5 L round bottom flask fitted with a mechanical stirrer and a Teflon coated thermocouple was added (−)-2,3-dibenzoyl-L-tartaric acid (1000 g, 2.79 mol) followed by acetic anhydride (2 L). The suspension was stirred and heated to 85° C. for 2 h during which time the starting material gradually dissolved. A short time thereafter, the product began to crystallize in the reaction mixture and the suspension was then cooled to 25° C. The product was collected by filtration, washed with 10% acetone in hexane (2×1 L), and dried in a vacuum oven at 50° C. overnight to afford (3R,4R)-2,5-dioxo-3,4-dibenzoyloxy-3,4-dihydrofuran (29) as a white solid. $^1$H NMR ($CDCl_3$, 400 MHz): δ 6.0 (s, 2H), 7.45 (app. t, 4H), 7.65 (app. t, 2H), 8.05 (d, 4H).

In a second step (Step B), to a 3-neck 5 L round bottom flask fitted with a mechanical stirrer and a Teflon-coated temperature probe was added compound (29) (2.79 mol) followed by acetonitrile (2 L). The suspension was cooled in an ice bath to 4° C., followed by the addition of 50% aqueous hydroxylamine (180 mL, 2.93 mol) over 1 h. The starting material gradually dissolved during the addition and the reaction mixture was warmed to 20° C. and stirred for 1 h. The reaction mixture was concentrated in vacuo, diluted with EtOAc (1 L) and washed with 1 N HCl (2×1 L). The organic phase was separated and concentrated in vacuo to afford a viscous, red syrup. The syrup was then heated for two hours in toluene (2.5 L) at 100° C. with azeotropic removal of water. The syrup gradually dissolved and then the product crystallized. After cooling to room temperature the solid was collected by filtration, washed with 10% acetone in hexane (2×1 L) and dried in a vacuum oven to afford 1-hydroxy-(3R,4R)-2,5-dioxo-3,4-dibenzoyloxypyrrolidine (30) (862 g, 2.43 mol, 87% yield) as a white solid. $^1$H NMR (CDCl$_3$, 400 MHz): δ 5.85 (s, 2H), 7.45 (app. t, 4H), 7.65 (app t, 2H), 8.05 (m, 4H).

In a third step (Step C), a 3 L three necked round bottom flask fitted with a mechanical stirrer, Teflon coated temperature probe and an addition funnel was charged with compound (11) (234 g, 1 mol), compound (30) (330 g, 0.95 mol), and 1,2-dichloroethane (2200 mL). The reaction mixture was cooled under a nitrogen atmosphere in an ice water bath to 15° C. To the stirred reaction mixture was added a 39% solution of peracetic acid in dilute acetic acid (500 mL, 2.94 mol) over 2 h, maintaining the temperature between 15 and 22° C. This temperature was maintained for an additional 12 h during which time a white precipitate was formed. The reaction mixture was further cooled to 3-4° C., the product collected by filtration, and washed with hexane (2×1 L). The product was dried in vacuo, yielding (1S)-1-[((3R,4R)-2,5-dioxo-3, 4-dibenzoyloxypyrrolidinyl)-oxycarbonyloxy]-2-methylpropyl 2-methylpropanoate (28) (128 g, 0.24 mol, 25% yield). The diastereomeric purity of the product was determined to be >99% d.e. by HPLC using a chiral column. $^1$H NMR (CDCl$_3$, 400 MHz): δ 1.0 (d, 6H), 1.2 (dd, 6H), 2.1 (m, 1H), 2.65 (m, 1H), 6.0 (br. s, 2H), 6.6 (d, 1H), 7.45 (app. t, 4H), 7.65 (app. t, 2H), 8.05 (d, 4H).

Example 1

Synthesis of 3-{[1-Isobutanoyloxyethoxy]carbonylamino}propyl(n-butyl)phosphinic Acid (31)

To a solution of 3-aminopropyl(n-butyl)phosphinic acid (10 mmol) and sodium bicarbonate (20 mmol) in water (40 mL) was added a solution of compound (17) (10 mmol) in acetonitrile (20 mL) over 1 min. The reaction was stirred at ambient temperature for 16 h. The reaction mixture was diluted with ethylacetate (100 mL) and washed with 0.1 M aqueous potassium bisulfate (3×100 μL). The organic phase was separated, dried over anhydrous magnesium sulfate, filtered, and concentrated in vacuo to afford the title compound (31) as a white solid. $^1$H-NMR (400 MHz, CDCl$_3$): δ 6.78 (q, J=8 Hz, 1H), 3.49 (s, 1H), 3.28 (t, J=6.4 Hz, 2H), 2.51-2.55 (m, 1H), 1.80-1.84 (m, 2H), 1.65-1.75 (m, 3H), 1.55-1.58 (m, 2H), 1.39-1.48 (m, 4H), 1.17 (d, J=8.4 Hz, 9H), 0.93 (t, J=7.2 Hz, 3H). Phosphorus (162 MHz, CDCl$_3$) 60.31. MS (ESI) m/z 338 (M+H)$^+$.

Example 2

Synthesis of 3-{[1-Butanoyloxyethoxy]carbonylamino}propyl(n-butyl)phosphinic Acid (32)

Following the procedure of Example 1 and replacing compound (17) with compound (18) affords the title compound (32) as a white solid.

Example 3

Synthesis of 3-{[1-Pivaloyloxyethoxy]carbonylamino}propyl(n-butyl)phosphinic Acid (33)

Following the procedure of Example 1 and replacing compound (17) with compound (19) affords the title compound (33) as a white solid.

Example 4

Synthesis of 3-{[1-Cyclohexanoyloxyethoxy]carbonylamino}propyl(n-butyl)phosphinic Acid (34)

Following the procedure of Example 1 and replacing compound (17) with compound (20) afforded the title compound (34) as a white solid. $^1$H-NMR (400 MHz, CDCl$_3$): δ 7.42 (br, 1H), 6.76 (q, J=5.6 Hz, 1H), 3.25 (br, 2H), 2.24-2.30 (m, 1H), 1.19-1.90 (m, 20H). MS (ESI) m/z 336 (M+H)$^+$ Example 5

Synthesis of 3-{[Isobutanoyloxymethoxy]carbonylamino}propyl(n-butyl)phosphinic Acid (35)

Following the procedure of Example 1 and replacing compound (17) with compound (21) afforded the title compound (35) as a white solid. $^1$H-NMR (400 MHz, CDCl$_3$): δ 5.71 (s, 2H), 3.29-3.32 (t, J=6.8 Hz, 2H), 2.57-2.61 (m, 1H), 1.73-1.84 (m, 2H), 1.68-1.72 (m, 4H), 1.55-1.57 (m, 2H), 1.38-1.44 (m, 2H), 1.18 (d, J=7.2 Hz), 0.9 (t, J=7.2 Hz, 3H).

Phosphorus (162 MHz, CD$_3$OD) 60.61

MS (ESI) m/z 324 (M+H)$^+$.

Example 6

Synthesis of 3-{[Butanoyloxymethoxy]carbonylamino}propyl(n-butyl)phosphinic Acid (36)

Following the procedure of Example 1 and replacing compound (17) with compound (22) affords the title compound (36) as a white solid.

Example 7

Synthesis of 3-{[Pivaloyloxymethoxy]carbonylamino}propyl(n-butyl)phosphinic Acid (37)

Following the procedure of Example 1 and replacing compound (17) with compound (23) affords the title compound (37) as a white solid.

Example 8

Synthesis of 3-{[Cyclohexanoyloxymethoxy]carbonylamino}propyl(n-butyl)phosphinic Acid (38)

Following the procedure of Example 1 and replacing compound (17) with compound (24) affords the title compound (38) as a white solid.

Example 9

Synthesis of 3-{[(1R)-Isobutanoyloxyisobutoxy]carbonylamino}propyl(n-butyl)phosphinic Acid (39)

To a 3 L three necked round bottom flask fitted with a mechanical stirrer, temperature probe, and nitrogen inlet was added compound (25) (100 mmol), 3-aminopropyl(n-butyl) phosphinic acid (100 mmol), THF (1 L), and water (100 mL). The suspension was stirred under a nitrogen atmosphere at 18-20° C. for 4 h during which time the reaction mixture became homogeneous. The THF was removed in vacuo and the reaction mixture was diluted with methyl tert-butyl ether (250 mL) and washed with 1N HCl (1×500 mL) and water (2×200 mL). The organic phase was separated and concentrated in vacuo to leave a white solid. The solid was purified by flash chromatography to afford the product (39) as a white solid. $^1$H-NMR (400 MHz, CD$_3$OD): δ 6.74-6.70 (q, J=5.2, 1H), 4.06-3.96 (m, 1H), 3.22-3.21 (m, 2H), 2.547-2.477 (m, 1H), 1.92-1.84 (m, 2H), 1.52-1.48 (s, 3H), 1.142-1.138 (d, J=1.6, 3.0H), 1.124-1.121 (dd, J=1.6, 3.0H). Phosphorus (162 MHz, CD$_3$OD): 51.04; MS (ESI) m/z 346 (M+H)$^+$)

Example 10

Synthesis of 3-{[(1S)-Isobutanoyloxyisobutoxy]carbonylamino}propyl(n-butyl)phosphinic Acid (40)

Following the procedure of Example 9 and replacing compound (25) with compound (28) affords the title compound (40) as a white solid.

Example 11

Synthesis of 3-{[1-Isobutanoyloxyethoxy]carbonylamino}-(2R)-hydroxypropyl(n-butyl)phosphinic Acid (41)

Following the procedure of Example 1 and replacing 3-aminopropyl(n-butyl)phosphinic acid with 3-amino-(2R)-hydroxypropyl(n-butyl)phosphinic acid affords the title compound (41) as a white solid.

Example 12

Synthesis of 3-{[1-Butanoyloxyethoxy]carbonylamino}-(2R)-hydroxypropyl(n-butyl)phosphinic Acid (42)

Following the procedure of Example 2 and replacing 3-aminopropyl(n-butyl)phosphinic acid with 3-amino-(2R)-hydroxypropyl(n-butyl)phosphinic acid affords the title compound (42) as a white solid.

Example 13

Synthesis of 3-{[1-Pivaloyloxyethoxy]carbonylamino}-(2R)-hydroxypropyl(n-butyl)phosphinic Acid (43)

Following the procedure of Example 3 and replacing 3-aminopropyl(n-butyl)phosphinic acid with 3-amino-(2R)-hydroxypropyl(n-butyl)phosphinic acid affords the title compound (43) as a white solid.

Example 14

Synthesis of 3-{[1-Cyclohexanoyloxyethoxy]carbonylamino}-(2R)-hydroxypropyl(n-butyl)phosphinic Acid (44)

Following the procedure of Example 4 and replacing 3-aminopropyl(n-butyl)phosphinic acid with 3-amino-(2R)-hydroxypropyl(n-butyl)phosphinic acid affords the title compound (44) as a white solid.

Example 15

Synthesis of 3-{[Isobutanoyloxymethoxy]carbonylamino}-(2R)-hydroxypropyl(n-butyl)phosphinic Acid (45)

Following the procedure of Example 5 and replacing 3-aminopropyl(n-butyl)phosphinic acid with 3-amino-(2R)-hydroxypropyl(n-butyl)phosphinic acid affords the title compound (45) as a white solid.

Example 16

Synthesis of 3-{[Butanoyloxymethoxy]carbonylamino}-(2R)-hydroxypropyl(n-butyl)phosphinic Acid (46)

Following the procedure of Example 6 and replacing 3-aminopropyl(n-butyl)phosphinic acid with 3-amino-(2R)-hydroxypropyl(n-butyl)phosphinic acid affords the title compound (46) as a white solid.

Example 17

Synthesis of 3-{[Pivaloyloxymethoxy]carbonylamino}-(2R)-hydroxypropyl(n-butyl)phosphinic Acid (47)

Following the procedure of Example 7 and replacing 3-aminopropyl(n-butyl)phosphinic acid with 3-amino-(2R)-hydroxypropyl(n-butyl)phosphinic acid affords the title compound (47) as a white solid.

Example 18

Synthesis of 3-{[Cyclohexanoyloxymethoxy]carbonylamino}-(2R)-hydroxypropyl(n-butyl)phosphinic Acid (48)

Following the procedure of Example 8 and replacing 3-aminopropyl(n-butyl)phosphinic acid with 3-amino-(2R)-hydroxypropyl(n-butyl)phosphinic acid affords the title compound (48) as a white solid.

Example 19

Synthesis of 3-{[(1R)-Isobutanoyloxyisobutoxy]carbonylamino}-(2R)-hydroxypropyl(n-butyl)phosphinic Acid (49)

Following the procedure of Example 9 and replacing 3-aminopropyl(n-butyl)phosphinic acid with 3-amino-(2R)-hydroxypropyl(n-butyl)phosphinic acid affords the title compound (49) as a white solid.

Example 20

Synthesis of 3-{[(1S)-Isobutanoyloxyisobutoxy]carbonylamino}-(2R)-hydroxypropyl(n-butyl)phosphinic Acid (50)

Following the procedure of Example 10 and replacing 3-aminopropyl(n-butyl)phosphinic acid with 3-amino-(2R)-hydroxypropyl(n-butyl)phosphinic acid affords the title compound (50) as a white solid.

Example 21

Synthesis of 3-{[1-Isobutanoyloxyethoxy]carbonylamino}-(2S)-hydroxypropyl(n-butyl)phosphinic Acid (51)

Following the procedure of Example 1 and replacing 3-aminopropyl(n-butyl)phosphinic acid with 3-amino-(2S)-hydroxypropyl(n-butyl)phosphinic acid affords the title compound (51) as a white solid.

Example 22

Synthesis of 3-{[1-Butanoyloxyethoxy]carbonylamino}-(2S)-hydroxypropyl(n-butyl)phosphinic Acid (52)

Following the procedure of Example 2 and replacing 3-aminopropyl(n-butyl)phosphinic acid with 3-amino-(2S)-hydroxypropyl(n-butyl)phosphinic acid affords the title compound (52) as a white solid.

Example 23

Synthesis of 3-{[1-Pivaloyloxyethoxy]carbonylamino}-(2S)-hydroxypropyl(n-butyl)phosphinic Acid (53)

Following the procedure of Example 3 and replacing 3-aminopropyl(n-butyl)phosphinic acid with 3-amino-(2S)-hydroxypropyl(n-butyl)phosphinic acid affords the title compound (53) as a white solid.

Example 24

Synthesis of 3-{[1-Cyclohexanoyloxyethoxy]carbonylamino}-(2S)-hydroxypropyl(n-butyl)phosphinic Acid (54)

Following the procedure of Example 4 and replacing 3-aminopropyl(n-butyl)phosphinic acid with 3-amino-(2S)-hydroxypropyl(n-butyl)phosphinic acid affords the title compound (54) as a white solid.

Example 25

Synthesis of 3-{[Isobutanoyloxymethoxy]carbonylamino}-(2S)-hydroxypropyl(n-butyl)phosphinic Acid (55)

Following the procedure of Example 5 and replacing 3-aminopropyl(n-butyl)phosphinic acid with 3-amino-(2S)-hydroxypropyl(n-butyl)phosphinic acid affords the title compound (55) as a white solid.

Example 26

Synthesis of 3-{[Butanoyloxymethoxy]carbonylamino}-(2S)-hydroxypropyl(n-butyl)phosphinic Acid (56)

Following the procedure of Example 6 and replacing 3-aminopropyl(n-butyl)phosphinic acid with 3-amino-(2S)-hydroxypropyl(n-butyl)phosphinic acid affords the title compound (56) as a white solid.

Example 27

Synthesis of 3-{[Pivaloyloxymethoxy]carbonylamino}-(2S)-hydroxypropyl(n-butyl)phosphinic Acid (57)

Following the procedure of Example 7 and replacing 3-aminopropyl(n-butyl)phosphinic acid with 3-amino-(2S)-hydroxypropyl(n-butyl)phosphinic acid affords the title compound (57) as a white solid.

Example 28

Synthesis of 3-{[Cyclohexanoyloxymethoxy]carbonylamino}-(2S)-hydroxypropyl(n-butyl)phosphinic Acid (58)

Following the procedure of Example 8 and replacing 3-aminopropyl(n-butyl)phosphinic acid with 3-amino-(2S)-hydroxypropyl(n-butyl)phosphinic acid affords the title compound (58) as a white solid.

Example 29

Synthesis of 3-{[(1R)-Isobutanoyloxyisobutoxy]carbonylamino}-(2S)-hydroxypropyl(n-butyl)phosphinic Acid (59)

Following the procedure of Example 9 and replacing 3-aminopropyl(n-butyl)phosphinic acid with 3-amino-(2S)-hydroxypropyl(n-butyl)phosphinic acid affords the title compound (59) as a white solid.

Example 30

Synthesis of 3-{[(1S)-Isobutanoyloxyisobutoxy]carbonylamino}-(2S)-hydroxypropyl(n-butyl)phosphinic Acid (60)

Following the procedure of Example 10 and replacing 3-aminopropyl(n-butyl)phosphinic acid with 3-amino-(2S)-hydroxypropyl(n-butyl)phosphinic acid affords the title compound (60) as a white solid.

Example 31

Synthesis of 3-{[1-Isobutanoyloxyethoxy]carbonylamino}-(2R)-fluoropropyl(n-butyl)phosphinic Acid (61)

Following the procedure of Example 1 and replacing 3-aminopropyl(n-butyl)phosphinic acid with 3-amino-(2R)-fluoropropyl(n-butyl)phosphinic acid affords the title compound (61) as a white solid.

Example 32

Synthesis of 3-{[1-Butanoyloxyethoxy]carbonylamino}-(2R)-fluoropropyl(n-butyl)phosphinic Acid (62)

Following the procedure of Example 2 and replacing 3-aminopropyl(n-butyl)phosphinic acid with 3-amino-(2R)-fluoropropyl(n-butyl)phosphinic acid affords the title compound (62) as a white solid.

Example 33

Synthesis of 3-{[1-Pivaloyloxyethoxy]carbonylamino}-(2R)-fluoropropyl(n-butyl)phosphinic Acid (63)

Following the procedure of Example 3 and replacing 3-aminopropyl(n-butyl)phosphinic acid with 3-amino-(2R)-fluoropropyl(n-butyl)phosphinic acid affords the title compound (63) as a white solid.

Example 34

Synthesis of 3-{[1-Cyclohexanoyloxyethoxy]carbonylamino}-(2R)-fluoropropyl(n-butyl)phosphinic Acid (64)

Following the procedure of Example 4 and replacing 3-aminopropyl(n-butyl)phosphinic acid with 3-amino-(2R)-fluoropropyl(n-butyl)phosphinic acid affords the title compound (64) as a white solid.

Example 35

Synthesis of 3-{[Isobutanoyloxymethoxy]carbonylamino}-(2R)-fluoropropyl(n-butyl)phosphinic Acid (65)

Following the procedure of Example 5 and replacing 3-aminopropyl(n-butyl)phosphinic acid with 3-amino-(2R)-fluoropropyl(n-butyl)phosphinic acid affords the title compound (65) as a white solid.

Example 36

Synthesis of 3-{[Butanoyloxymethoxy]carbonylamino}-(2R)-fluoropropyl(n-butyl)phosphinic Acid (66)

Following the procedure of Example 6 and replacing 3-aminopropyl(n-butyl)phosphinic acid with 3-amino-(2R)-fluoropropyl(n-butyl)phosphinic acid affords the title compound (66) as a white solid.

Example 37

Synthesis of 3-{[Pivaloyloxymethoxy]carbonylamino}-(2R)-fluoropropyl(n-butyl)phosphinic Acid (67)

Following the procedure of Example 7 and replacing 3-aminopropyl(n-butyl)phosphinic acid with 3-amino-(2R)-fluoropropyl(n-butyl)phosphinic acid affords the title compound (67) as a white solid.

Example 38

Synthesis of 3-{[Cyclohexanoyloxy methoxy]carbonylamino}-(2R)-fluoropropyl(n-butyl)phosphinic Acid (68)

Following the procedure of Example 8 and replacing 3-aminopropyl(n-butyl)phosphinic acid with 3-amino-(2R)-fluoropropyl(n-butyl)phosphinic acid affords the title compound (68) as a white solid.

Example 39

Synthesis of 3-{[(1R)-Isobutanoyloxyisobutoxy]carbonylamino}-(2R)-fluoropropyl(n-butyl)phosphinic Acid (69)

Following the procedure of Example 9 and replacing 3-aminopropyl(n-butyl)phosphinic acid with 3-amino-(2R)-fluoropropyl(n-butyl)phosphinic acid affords the title compound (69) as a white solid.

Example 40

Synthesis of 3-{[(1S)-Isobutanoyloxyisobutoxy]carbonylamino}-(2R)-fluoropropyl(n-butyl)phosphinic Acid (70)

Following the procedure of Example 10 and replacing 3-aminopropyl(n-butyl)phosphinic acid with 3-amino-(2R)-fluoropropyl(n-butyl)phosphinic acid affords the title compound (70) as a white solid.

Example 41

Synthesis of 3-{[1-Isobutanoyloxyethoxy]carbonylamino}-(2S)-fluoropropyl(n-butyl)phosphinic Acid (71)

Following the procedure of Example 1 and replacing 3-aminopropyl(n-butyl)phosphinic acid with 3-amino-(2S)-fluoropropyl(n-butyl)phosphinic acid affords the title compound (71) as a white solid.

Example 42

Synthesis of 3-{[1-Butanoyloxyethoxy]carbonylamino}-(2S)-fluoropropyl(n-butyl)phosphinic Acid (72)

Following the procedure of Example 2 and replacing 3-aminopropyl(n-butyl)phosphinic acid with 3-amino-(2S)-fluoropropyl(n-butyl)phosphinic acid affords the title compound (72) as a white solid.

Example 43

Synthesis of 3-{[1-Pivaloyloxyethoxy]carbonylamino}-(2S)-fluoropropyl(n-butyl)phosphinic Acid (73)

Following the procedure of Example 3 and replacing 3-aminopropyl(n-butyl)phosphinic acid with 3-amino-(2S)-fluoropropyl(n-butyl)phosphinic acid affords the title compound (73) as a white solid.

Example 44

Synthesis of 3-{[1-Cyclohexanoyloxyethoxy]carbonylamino}-(2S)-fluoropropyl(n-butyl)phosphinic Acid (74)

Following the procedure of Example 4 and replacing 3-aminopropyl(n-butyl)phosphinic acid with 3-amino-(2S)-fluoropropyl(n-butyl)phosphinic acid affords the title compound (74) as a white solid.

Example 45

Synthesis of 3-{[Isobutanoyloxymethoxy]carbonylamino}-(2S)-fluoropropyl(n-butyl)phosphinic Acid (75)

Following the procedure of Example 5 and replacing 3-aminopropyl(n-butyl)phosphinic acid with 3-amino-(2S)-fluoropropyl(n-butyl)phosphinic acid affords the title compound (75) as a white solid.

Example 46

Synthesis of 3-{[Butanoyloxymethoxy]carbonylamino}-(2S)-fluoropropyl(n-butyl)phosphinic Acid (76)

Following the procedure of Example 6 and replacing 3-aminopropyl(n-butyl)phosphinic acid with 3-amino-(2S)-fluoropropyl(n-butyl)phosphinic acid affords the title compound (76) as a white solid.

Example 47

Synthesis of 3-{[Pivaloyloxymethoxy]carbonylamino}-(2S)-fluoropropyl(n-butyl)phosphinic Acid (77)

Following the procedure of Example 7 and replacing 3-aminopropyl(n-butyl)phosphinic acid with 3-amino-(2S)-fluoropropyl(n-butyl)phosphinic acid affords the title compound (77) as a white solid.

Example 48

Synthesis of 3-{[Cyclohexanoyloxymethoxy]carbonylamino}-(2S)-fluoropropyl(n-butyl)phosphinic Acid (78)

Following the procedure of Example 8 and replacing 3-aminopropyl(n-butyl)phosphinic acid with 3-amino-(2S)-fluoropropyl(n-butyl)phosphinic acid affords the title compound (78) as a white solid.

Example 49

Synthesis of 3-{[(1R)-Isobutanoyloxyisobutoxy]carbonylamino}-(2S)-fluoropropyl(n-butyl)phosphinic Acid (79)

Following the procedure of Example 9 and replacing 3-aminopropyl(n-butyl)phosphinic acid with 3-amino-(2S)-fluoropropyl(n-butyl)phosphinic acid affords the title compound (79) as a white solid.

Example 50

Synthesis of 3-{[(1S)-Isobutanoyloxyisobutoxy]carbonylamino}-(2S)-fluoropropyl(n-butyl)phosphinic Acid (80)

Following the procedure of Example 10 and replacing 3-aminopropyl(n-butyl)phosphinic acid with 3-amino-(2S)-fluoropropyl(n-butyl)phosphinic acid affords the title compound (80) as a white solid.

Example 51

Synthesis of 3-{[1-Isobutanoyloxyethoxy]carbonylamino}-2-oxopropyl(n-butyl)phosphinic Acid (81)

Following the procedure of Example 1 and replacing 3-aminopropyl(n-butyl)phosphinic acid with 3-amino-2-oxopropyl(n-butyl)phosphinic acid affords the title compound (81) as a white solid.

Example 52

Synthesis of 3-{[1-Butanoyloxyethoxy]carbonylamino}-2-oxopropyl(n-butyl)phosphinic Acid (82)

Following the procedure of Example 2 and replacing 3-aminopropyl(n-butyl)phosphinic acid with 3-amino-2-oxopropyl(n-butyl)phosphinic acid affords the title compound (82) as a white solid.

Example 53

Synthesis of 3-{[1-Pivaloyloxyethoxy]carbonylamino}-2-oxopropyl(n-butyl)phosphinic Acid (83)

Following the procedure of Example 3 and replacing 3-aminopropyl(n-butyl)phosphinic acid with 3-amino-2-oxopropyl(n-butyl)phosphinic acid affords the title compound (83) as a white solid.

Example 54

Synthesis of 3-{[1-Cyclohexanoyloxyethoxy]carbonylamino}-2-oxopropyl(n-butyl)phosphinic Acid (84)

Following the procedure of Example 4 and replacing 3-aminopropyl(n-butyl)phosphinic acid with 3-amino-2-oxopropyl(n-butyl)phosphinic acid affords the title compound (84) as a white solid.

Example 55

Synthesis of 3-{[Isobutanoyloxymethoxy]carbonylamino}-2-oxopropyl(n-butyl)phosphinic Acid (85)

Following the procedure of Example 5 and replacing 3-aminopropyl(n-butyl)phosphinic acid with 3-amino-2-oxopropyl(n-butyl)phosphinic acid affords the title compound (85) as a white solid.

Example 56

Synthesis of 3-{[Butanoyloxymethoxy]carbonylamino}-2-oxopropyl(n-butyl)phosphinic Acid (86)

Following the procedure of Example 6 and replacing 3-aminopropyl(n-butyl)phosphinic acid with 3-amino-2-oxopropyl(n-butyl)phosphinic acid affords the title compound (86) as a white solid.

Example 57

Synthesis of 3-{[Pivaloyloxymethoxy]carbonylamino}-2-oxopropyl(n-butyl)phosphinic Acid (87)

Following the procedure of Example 7 and replacing 3-aminopropyl(n-butyl)phosphinic acid with 3-amino-2-oxopropyl(n-butyl)phosphinic acid affords the title compound (87) as a white solid.

Example 58

Synthesis of 3-{[Cyclohexanoyloxymethoxy]carbonylamino}-2-oxopropyl(n-butyl)phosphinic Acid (88)

Following the procedure of Example 8 and replacing 3-aminopropyl(n-butyl)phosphinic acid with 3-amino-2-oxopropyl(n-butyl)phosphinic acid affords the title compound (88) as a white solid.

Example 59

Synthesis of 3-{[(1R)-Isobutanoyloxyisobutoxy]carbonylamino}-2-oxopropyl(n-butyl)phosphinic Acid (89)

Following the procedure of Example 9 and replacing 3-aminopropyl(n-butyl)phosphinic acid with 3-amino-2-oxopropyl(n-butyl)phosphinic acid affords the title compound (89) as a white solid.

Example 60

Synthesis of 3-{[(1S)-Isobutanoyloxyisobutoxy]carbonylamino}-2-oxopropyl(n-butyl)phosphinic Acid (90)

Following the procedure of Example 10 and replacing 3-aminopropyl(n-butyl)phosphinic acid with 3-amino-2-oxopropyl(n-butyl)phosphinic acid affords the title compound (90) as a white solid.

Example 61

Synthesis of 3-{[1-Isobutanoyloxyethoxy]carbonylamino}propyl(cyclohexylmethyl)phosphinic Acid (91)

To a solution of 3-aminopropyl(cyclohexylmethyl)phosphinic acid (10 mmol) and sodium bicarbonate (20 mmol) in water (40 mL) is added a solution of compound (17) (10 mmol) in acetonitrile (20 mL) over 1 min. The reaction is stirred at ambient temperature for 16 h. The reaction mixture is diluted with diethyl ether (100 mL) and washed with 0.1 M aqueous potassium bisulfate (3×100 mL). The organic phase is separated, dried over anhydrous magnesium sulfate, filtered, and concentrated in vacuo to afford the title compound (91) as a white solid.

Example 62

Synthesis of 3-{[1-Butanoyloxyethoxy]carbonylamino}propyl(cyclohexylmethyl)phosphinic Acid (92)

Following the procedure of Example 61 and replacing compound (17) with compound (18) affords the title compound (92) as a white solid.

Example 63

Synthesis of 3-{[1-Pivaloyloxyethoxy]carbonylamino}propyl(cyclohexylmethyl)phosphinic Acid (93)

Following the procedure of Example 61 and replacing compound (17) with compound (19) affords the title compound (93) as a white solid.

Example 64

Synthesis of 3-{[1-Cyclohexanoyloxyethoxy]carbonylamino}propyl(cyclohexylmethyl)phosphinic Acid (94)

Following the procedure of Example 61 and replacing compound (17) with compound (20) affords the title compound (94) as a white solid.

Example 65

Synthesis of 3-{[Isobutanoyloxymethoxy]carbonylamino}propyl(cyclohexylmethyl)phosphinic Acid (95)

Following the procedure of Example 61 and replacing compound (17) with compound (21) affords the title compound (95) as a white solid.

Example 66

Synthesis of 3-{[Butanoyloxymethoxy]carbonylamino}propyl(cyclohexylmethyl)phosphinic Acid (96)

Following the procedure of Example 61 and replacing compound (17) with compound (22) affords the title compound (96) as a white solid.

Example 67

Synthesis of 3-{[Pivaloyloxymethoxy]carbonylamino}propyl(cyclohexylmethyl)phosphinic Acid (97)

Following the procedure of Example 61 and replacing compound (17) with compound (23) affords the title compound (97) as a white solid.

Example 68

Synthesis of 3-{[Cyclohexanoyloxymethoxy] carbonylamino}propyl(cyclohexylmethyl)phosphinic Acid (98)

Following the procedure of Example 61 and replacing compound (17) with compound (24) affords the title compound (98) as a white solid.

Example 69

Synthesis of 3-{[(1R)-Isobutanoyloxyisobutoxy] carbonylamino}propyl(cyclohexylmethyl)phosphinic Acid (99)

To a 3 L three necked round bottom flask fitted with a mechanical stirrer, temperature probe, and nitrogen inlet is added compound (25) (100 mmol), 3-aminopropyl(cyclohexylmethyl)phosphinic acid (100 mmol), THF (1 L), and water (100 mL). The suspension is stirred under a nitrogen atmosphere at 18-20° C. for 4 h during which time the reaction mixture becomes homogeneous. The THF is removed in vacuo and the reaction mixture is diluted with methyl tert-butyl ether (250 mL) and washed with 1N HCl (1×500 mL) and water (2×200 mL). The organic phase is separated and concentrated in vacuo to leave a white solid. The solid is purified by flash chromatography to afford the product (99) as a white solid.

Example 70

Synthesis of 3-{[(1S)-Isobutanoyloxyisobutoxy] carbonylamino}propyl(cyclohexylmethyl)phosphinic Acid (100)

Following the procedure of Example 69 and replacing compound (25) with compound (28) affords the title compound (100) as a white solid.

Example 71

Synthesis of 3-{[1-Isobutanoyloxyethoxy]carbonylamino}-(2R)-hydroxypropyl(cyclohexylmethyl) phosphinic Acid (101)

Following the procedure of Example 61 and replacing 3-aminopropyl(cyclohexylmethyl)phosphinic acid with 3-amino-(2R)-hydroxypropyl(cyclohexylmethyl)phosphinic acid affords the title compound (101) as a white solid.

Example 72

Synthesis of 3-{[1-Butanoyloxyethoxy]carbonylamino}-(2R)-hydroxypropyl(cyclohexylmethyl) phosphinic Acid (102)

Following the procedure of Example 62 and replacing 3-aminopropyl(cyclohexylmethyl)phosphinic acid with 3-amino-(2R)-hydroxypropyl(cyclohexylmethyl)phosphinic acid affords the title compound (102) as a white solid.

Example 73

Synthesis of 3-{[1-Pivaloyloxyethoxy]carbonylamino}-(2R)-hydroxypropyl(cyclohexylmethyl) phosphinic Acid (103)

Following the procedure of Example 63 and replacing 3-aminopropyl(cyclohexylmethyl)phosphinic acid with 3-amino-(2R)-hydroxypropyl(cyclohexylmethyl)phosphinic acid affords the title compound (103) as a white solid.

Example 74

Synthesis of 3-{[1-Cyclohexanoyloxyethoxy]carbonylamino}-(2R)-hydroxypropyl(cyclohexylmethyl) phosphinic Acid (104)

Following the procedure of Example 64 and replacing 3-aminopropyl(cyclohexylmethyl)phosphinic acid with 3-amino-(2R)-hydroxypropyl(cyclohexylmethyl)phosphinic acid affords the title compound (104) as a white solid.

Example 75

Synthesis of 3-{[Isobutanoyloxymethoxy]carbonylamino}-(2R)-hydroxypropyl(cyclohexylmethyl) phosphinic Acid (105)

Following the procedure of Example 65 and replacing 3-aminopropyl(cyclohexylmethyl)phosphinic acid with 3-amino-(2R)-hydroxypropyl(cyclohexylmethyl)phosphinic acid affords the title compound (105) as a white solid.

Example 76

Synthesis of 3-{[Butanoyloxymethoxy]carbonylamino}-(2R)-hydroxypropyl(cyclohexylmethyl) phosphinic Acid (106)

Following the procedure of Example 66 and replacing 3-aminopropyl(cyclohexylmethyl)phosphinic acid with 3-amino-(2R)-hydroxypropyl(cyclohexylmethyl)phosphinic acid affords the title compound (106) as a white solid.

Example 77

Synthesis of 3-{[Pivaloyloxymethoxy]carbonylamino}-(2R)-hydroxypropyl(cyclohexylmethyl) phosphinic Acid (107)

Following the procedure of Example 67 and replacing 3-aminopropyl(cyclohexylmethyl)phosphinic acid with 3-amino-(2R)-hydroxypropyl(cyclohexylmethyl)phosphinic acid affords the title compound (107) as a white solid.

Example 78

Synthesis of 3-{[Cyclohexanoyloxymethoxy]carbonylamino}-(2R)-hydroxypropyl(cyclohexylmethyl) phosphinic Acid (108)

Following the procedure of Example 68 and replacing 3-aminopropyl(cyclohexylmethyl)phosphinic acid with 3-amino-(2R)-hydroxypropyl(cyclohexylmethyl)phosphinic acid affords the title compound (108) as a white solid.

Example 79

Synthesis of 3-{[(1R)-Isobutanoyloxyisobutoxy]carbonylamino}-(2R)-hydroxypropyl(cyclohexylmethyl)phosphinic Acid (109)

Following the procedure of Example 69 and replacing 3-aminopropyl(cyclohexylmethyl)phosphinic acid with 3-amino-(2R)-hydroxypropyl(cyclohexylmethyl)phosphinic acid affords the title compound (109) as a white solid.

Example 80

Synthesis of 3-{[(1S)-Isobutanoyloxyisobutoxy]carbonylamino}-(2R)-hydroxypropyl(cyclohexylmethyl)phosphinic Acid (110)

Following the procedure of Example 70 and replacing 3-aminopropyl(cyclohexylmethyl)phosphinic acid with 3-amino-(2R)-hydroxypropyl(cyclohexylmethyl)phosphinic acid affords the title compound (110) as a white solid.

Example 81

Synthesis of 3-{[1-Isobutanoyloxyethoxy]carbonylamino}-(2S)-hydroxypropyl(cyclohexylmethyl)phosphinic Acid (111)

Following the procedure of Example 61 and replacing 3-aminopropyl(cyclohexylmethyl)phosphinic acid with 3-amino-(2S)-hydroxypropyl(cyclohexylmethyl)phosphinic acid affords the title compound (111) as a white solid.

Example 82

Synthesis of 3-{[1-Butanoyloxyethoxy]carbonylamino}-(2S)-hydroxypropyl(cyclohexylmethyl)phosphinic Acid (112)

Following the procedure of Example 62 and replacing 3-aminopropyl(cyclohexylmethyl)phosphinic acid with 3-amino-(2S)-hydroxypropyl(cyclohexylmethyl)phosphinic acid affords the title compound (112) as a white solid.

Example 83

Synthesis of 3-{[1-Pivaloyloxyethoxy]carbonylamino}-(2S)-hydroxypropyl(cyclohexylmethyl)phosphinic Acid (113)

Following the procedure of Example 63 and replacing 3-aminopropyl(cyclohexylmethyl)phosphinic acid with 3-amino-(2S)-hydroxypropyl(cyclohexylmethyl)phosphinic acid affords the title compound (113) as a white solid.

Example 84

Synthesis of 3-{[1-Cyclohexanoyloxyethoxy]carbonylamino}-(2S)-hydroxypropyl(cyclohexylmethyl)phosphinic Acid (114)

Following the procedure of Example 64 and replacing 3-aminopropyl(cyclohexylmethyl)phosphinic acid with 3-amino-(2S)-hydroxypropyl(cyclohexylmethyl)phosphinic acid affords the title compound (114) as a white solid.

Example 85

Synthesis of 3-{[Isobutanoyloxymethoxy]carbonylamino}-(2S)-hydroxypropyl(cyclohexylmethyl)phosphinic Acid (115)

Following the procedure of Example 65 and replacing 3-aminopropyl(cyclohexylmethyl)phosphinic acid with 3-amino-(2S)-hydroxypropyl(cyclohexylmethyl)phosphinic acid affords the title compound (115) as a white solid.

Example 86

Synthesis of 3-{[Butanoyloxymethoxy]carbonylamino}-(2S)-hydroxypropyl(cyclohexylmethyl)phosphinic Acid (116)

Following the procedure of Example 66 and replacing 3-aminopropyl(cyclohexylmethyl)phosphinic acid with 3-amino-(2S)-hydroxypropyl(cyclohexylmethyl)phosphinic acid affords the title compound (116) as a white solid.

Example 87

Synthesis of 3-{[Pivaloyloxymethoxy]carbonylamino}-(2S)-hydroxypropyl(cyclohexylmethyl)phosphinic Acid (117)

Following the procedure of Example 67 and replacing 3-aminopropyl(cyclohexylmethyl)phosphinic acid with 3-amino-(2S)-hydroxypropyl(cyclohexylmethyl)phosphinic acid affords the title compound (117) as a white solid.

Example 88

Synthesis of 3-{[Cyclohexanoyloxymethoxy]carbonylamino}-(2S)-hydroxypropyl(cyclohexylmethyl)phosphinic Acid (118)

Following the procedure of Example 68 and replacing 3-aminopropyl(cyclohexylmethyl)phosphinic acid with 3-amino-(2S)-hydroxypropyl(cyclohexylmethyl)phosphinic acid affords the title compound (118) as a white solid.

Example 89

Synthesis of 3-{[(1R)-Isobutanoyloxyisobutoxy]carbonylamino}-(2S)-hydroxypropyl(cyclohexylmethyl)phosphinic Acid (119)

Following the procedure of Example 69 and replacing 3-aminopropyl(cyclohexylmethyl)phosphinic acid with 3-amino-(2S)-hydroxypropyl(cyclohexylmethyl)phosphinic acid affords the title compound (119) as a white solid.

Example 90

Synthesis of 3-{[(1S)-Isobutanoyloxyisobutoxy]carbonylamino}-(2S)-hydroxypropyl(cyclohexylmethyl)phosphinic Acid (120)

Following the procedure of Example 70 and replacing 3-aminopropyl(cyclohexylmethyl)phosphinic acid with 3-amino-(2S)-hydroxypropyl(cyclohexylmethyl)phosphinic acid affords the title compound (120) as a white solid.

Example 91

Synthesis of 3-{[1-Isobutanoyloxyethoxy]carbonylamino}-(2R)-fluoropropyl(cyclohexylmethyl)phosphinic Acid (121)

Following the procedure of Example 61 and replacing 3-aminopropyl(cyclohexylmethyl)phosphinic acid with 3-amino-(2R)-fluoropropyl(cyclohexylmethyl)phosphinic acid affords the title compound (121) as a white solid.

Example 92

Synthesis of 3-{[1-Butanoyloxyethoxy]carbonylamino}-(2R)-fluoropropyl(cyclohexylmethyl)phosphinic Acid (122)

Following the procedure of Example 62 and replacing 3-aminopropyl(cyclohexylmethyl)phosphinic acid with 3-amino-(2R)-fluoropropyl(cyclohexylmethyl)phosphinic acid affords the title compound (122) as a white solid.

Example 93

Synthesis of 3-{[1-Pivaloyloxyethoxy]carbonylamino}-(2R)-fluoropropyl(cyclohexylmethyl)phosphinic Acid (123)

Following the procedure of Example 63 and replacing 3-aminopropyl(cyclohexylmethyl)phosphinic acid with 3-amino-(2R)-fluoropropyl(cyclohexylmethyl)phosphinic acid affords the title compound (123) as a white solid.

Example 94

Synthesis of 3-{[1-Cyclohexanoyloxyethoxy]carbonylamino}-(2R)-fluoropropyl(cyclohexylmethyl) phosphinic Acid (124)

Following the procedure of Example 64 and replacing 3-aminopropyl(cyclohexylmethyl)phosphinic acid with 3-amino-(2R)-fluoropropyl(cyclohexylmethyl)phosphinic acid affords the title compound (124) as a white solid.

Example 95

Synthesis of 3-{[Isobutanoyloxymethoxy]carbonylamino}-(2R)-fluoropropyl(cyclohexylmethyl)phosphinic Acid (125)

Following the procedure of Example 65 and replacing 3-aminopropyl(cyclohexylmethyl)phosphinic acid with 3-amino-(2R)-fluoropropyl(cyclohexylmethyl)phosphinic acid affords the title compound (125) as a white solid.

Example 96

Synthesis of 3-{[Butanoyloxymethoxy]carbonylamino}-(2R)-fluoropropyl(cyclohexylmethyl)phosphinic Acid (126)

Following the procedure of Example 66 and replacing 3-aminopropyl(cyclohexylmethyl)phosphinic acid with 3-amino-(2R)-fluoropropyl(cyclohexylmethyl)phosphinic acid affords the title compound (126) as a white solid.

Example 97

Synthesis of 3-{[Pivaloyloxymethoxy]carbonylamino}-(2R)-fluoropropyl(cyclohexylmethyl)phosphinic Acid (127)

Following the procedure of Example 67 and replacing 3-aminopropyl(cyclohexylmethyl)phosphinic acid with 3-amino-(2R)-fluoropropyl(cyclohexylmethyl)phosphinic acid affords the title compound (127) as a white solid.

Example 98

Synthesis of 3-{[Cyclohexanoyloxymethoxy]carbonylamino}-(2R)-fluoropropyl(cyclohexylmethyl) phosphinic Acid (128)

Following the procedure of Example 68 and replacing 3-aminopropyl(cyclohexylmethyl)phosphinic acid with 3-amino-(2R)-fluoropropyl(cyclohexylmethyl)phosphinic acid affords the title compound (128) as a white solid.

Example 99

Synthesis of 3-{[(1R)-Isobutanoyloxyisobutoxy]carbonylamino}-(2R)-fluoropropyl(cyclohexylmethyl)phosphinic Acid (129)

Following the procedure of Example 69 and replacing 3-aminopropyl(cyclohexylmethyl)phosphinic acid with 3-amino-(2R)-fluoropropyl(cyclohexylmethyl)phosphinic acid affords the title compound (129) as a white solid.

Example 100

Synthesis of 3-{[(1S)-Isobutanoyloxyisobutoxy]carbonylamino}-(2R)-fluoropropyl(cyclohexylmethyl) phosphinic Acid (130)

Following the procedure of Example 70 and replacing 3-aminopropyl(cyclohexylmethyl)phosphinic acid with 3-amino-(2R)-fluoropropyl(cyclohexylmethyl)phosphinic acid affords the title compound (130) as a white solid.

Example 101

Synthesis of 3-{[1-Isobutanoyloxyethoxy]carbonylamino}-(2S)-fluoropropyl(cyclohexylmethyl)phosphinic Acid (131)

Following the procedure of Example 61 and replacing 3-aminopropyl(cyclohexylmethyl)phosphinic acid with 3-amino-(2S)-fluoropropyl(cyclohexylmethyl)phosphinic acid affords the title compound (131) as a white solid.

Example 102

Synthesis of 3-{[1-Butanoyloxyethoxy]carbonylamino}-(2S)-fluoropropyl(cyclohexylmethyl)phosphinic Acid (132)

Following the procedure of Example 62 and replacing 3-aminopropyl(cyclohexylmethyl)phosphinic acid with 3-amino-(2S)-fluoropropyl(cyclohexylmethyl)phosphinic acid affords the title compound (132) as a white solid.

Example 103

Synthesis of 3-{[1-Pivaloyloxyethoxy]carbonylamino}-(2S)-fluoropropyl(cyclohexylmethyl)phosphinic Acid (133)

Following the procedure of Example 63 and replacing 3-aminopropyl(cyclohexylmethyl)phosphinic acid with 3-amino-(2S)-fluoropropyl(cyclohexylmethyl)phosphinic acid affords the title compound (133) as a white solid.

Example 104

Synthesis of 3-{[1-Cyclohexanoyloxyethoxy]carbonylamino}-(2S)-fluoropropyl(cyclohexylmethyl)phosphinic Acid (134)

Following the procedure of Example 64 and replacing 3-aminopropyl(cyclohexylmethyl)phosphinic acid with 3-amino-(2S)-fluoropropyl(cyclohexylmethyl)phosphinic acid affords the title compound (134) as a white solid.

Example 105

Synthesis of 3-{[Isobutanoyloxymethoxy]carbonylamino}-(2S)-fluoropropyl(cyclohexylmethyl)phosphinic Acid (135)

Following the procedure of Example 65 and replacing 3-aminopropyl(cyclohexylmethyl)phosphinic acid with 3-amino-(2S)-fluoropropyl(cyclohexylmethyl)phosphinic acid affords the title compound (135) as a white solid.

Example 106

Synthesis of 3-{[Butanoyloxymethoxy]carbonylamino}-(2S)-fluoropropyl(cyclohexylmethyl)phosphinic Acid (136)

Following the procedure of Example 66 and replacing 3-aminopropyl(cyclohexylmethyl)phosphinic acid with 3-amino-(2S)-fluoropropyl(cyclohexylmethyl)phosphinic acid affords the title compound (136) as a white solid.

Example 107

Synthesis of 3-{[Pivaloyloxymethoxy]carbonylamino}-(2S)-fluoropropyl(cyclohexylmethyl)phosphinic Acid (137)

Following the procedure of Example 67 and replacing 3-aminopropyl(cyclohexylmethyl)phosphinic acid with 3-amino-(2S)-fluoropropyl(cyclohexylmethyl)phosphinic acid affords the title compound (137) as a white solid.

Example 108

Synthesis of 3-{[Cyclohexanoyloxymethoxy]carbonylamino}-(2S)-fluoropropyl(cyclohexylmethyl)phosphinic Acid (138)

Following the procedure of Example 68 and replacing 3-aminopropyl(cyclohexylmethyl)phosphinic acid with 3-amino-(2S)-fluoropropyl(cyclohexylmethyl)phosphinic acid affords the title compound (138) as a white solid.

Example 109

Synthesis of 3-{[(1R)-Isobutanoyloxyisobutoxy]carbonylamino}-(2S)-fluoropropyl(cyclohexylmethyl)phosphinic Acid (139)

Following the procedure of Example 69 and replacing 3-aminopropyl(cyclohexylmethyl)phosphinic acid with 3-amino-(2S)-fluoropropyl(cyclohexylmethyl)phosphinic acid affords the title compound (139) as a white solid.

Example 110

Synthesis of 3-{[(1S)-Isobutanoyloxyisobutoxy]carbonylamino}-(2S)-fluoropropyl(cyclohexylmethyl)phosphinic Acid (140)

Following the procedure of Example 70 and replacing 3-aminopropyl(cyclohexylmethyl)phosphinic acid with 3-amino-(2S)-fluoropropyl(cyclohexylmethyl)phosphinic acid affords the title compound (140) as a white solid.

Example 111

Synthesis of 3-{[1-Isobutanoyloxyethoxy]carbonylamino}-2-oxopropyl(cyclohexylmethyl)phosphinic Acid (141)

Following the procedure of Example 61 and replacing 3-aminopropyl(cyclohexylmethyl)phosphinic acid with 3-amino-2-oxopropyl(cyclohexylmethyl)phosphinic acid affords the title compound (141) as a white solid.

Example 112

Synthesis of 3-{[1-Butanoyloxyethoxy]carbonylamino}-2-oxopropyl(cyclohexylmethyl)phosphinic Acid (142)

Following the procedure of Example 62 and replacing 3-aminopropyl(cyclohexylmethyl)phosphinic acid with 3-amino-2-oxopropyl(cyclohexylmethyl)phosphinic acid affords the title compound (142) as a white solid.

Example 113

Synthesis of 3-{[1-Pivaloyloxyethoxy]carbonylamino}-2-oxopropyl(cyclohexylmethyl)phosphinic Acid (143)

Following the procedure of Example 63 and replacing 3-aminopropyl(cyclohexylmethyl)phosphinic acid with 3-amino-2-oxopropyl(cyclohexylmethyl)phosphinic acid affords the title compound (143) as a white solid.

Example 114

Synthesis of 3-{[1-Cyclohexanoyloxyethoxy]carbonylamino}-2-oxopropyl(cyclohexylmethyl)phosphinic Acid (144)

Following the procedure of Example 64 and replacing 3-aminopropyl(cyclohexylmethyl)phosphinic acid with 3-amino-2-oxopropyl(cyclohexylmethyl)phosphinic acid affords the title compound (144) as a white solid.

Example 115

Synthesis of 3-{[Isobutanoyloxymethoxy]carbonylamino}-2-oxopropyl(cyclohexylmethyl)phosphinic Acid (145)

Following the procedure of Example 65 and replacing 3-aminopropyl(cyclohexylmethyl)phosphinic acid with 3-amino-2-oxopropyl(cyclohexylmethyl)phosphinic acid affords the title compound (145) as a white solid.

Example 116

Synthesis of 3-{[Butanoyloxymethoxy]carbonylamino}-2-oxopropyl(cyclohexylmethyl)phosphinic Acid (146)

Following the procedure of Example 66 and replacing 3-aminopropyl(cyclohexylmethyl)phosphinic acid with 3-amino-2-oxopropyl(cyclohexylmethyl)phosphinic acid affords the title compound (146) as a white solid.

Example 117

Synthesis of 3-{[Pivaloyloxymethoxy]carbonylamino}-2-oxopropyl(cyclohexylmethyl)phosphinic Acid (147)

Following the procedure of Example 67 and replacing 3-aminopropyl(cyclohexylmethyl)phosphinic acid with 3-amino-2-oxopropyl(cyclohexylmethyl)phosphinic acid affords the title compound (147) as a white solid.

Example 118

Synthesis of 3-{[Cyclohexanoyloxymethoxy]carbonylamino}-2-oxopropyl(cyclohexylmethyl)phosphinic Acid (148)

Following the procedure of Example 68 and replacing 3-aminopropyl(cyclohexylmethyl)phosphinic acid with 3-amino-2-oxopropyl(cyclohexylmethyl)phosphinic acid affords the title compound (148) as a white solid.

Example 119

Synthesis of 3-{[(1R)-Isobutanoyloxyisobutoxy]carbonylamino}-2-oxopropyl(cyclohexylmethyl)phosphinic Acid (149)

Following the procedure of Example 69 and replacing 3-aminopropyl(cyclohexylmethyl)phosphinic acid with 3-amino-2-oxopropyl(cyclohexylmethyl)phosphinic acid affords the title compound (149) as a white solid.

Example 120

Synthesis of 3-{[(1S)-Isobutanoyloxyisobutoxy]carbonylamino}-2-oxopropyl(cyclohexylmethyl)phosphinic Acid (150)

Following the procedure of Example 70 and replacing 3-aminopropyl(cyclohexylmethyl)phosphinic acid with 3-amino-2-oxopropyl(cyclohexylmethyl)phosphinic acid affords the title compound (150) as a white solid.

Example 121

Synthesis of 3-{N-(1'-Isobutanoyloxyethoxy)carbonyl-N-[1(R)-(3,4-dichlorophenyl)ethyl]amino}propyl(cyclohexylmethyl)phosphinic Acid (151)

To a solution of 3-{N-[1(R)-(3,4-dichlorophenyl)ethyl]amino}-propyl(cyclohexylmethyl)phosphinic acid (10 mmol) and sodium bicarbonate (20 mmol) in water (40 mL) is added a solution of compound (17) (10 mmol) in acetonitrile (20 mL) over 1 min. The reaction is stirred at ambient temperature for 16 h. The reaction mixture is diluted with diethyl ether (100 mL) and washed with 0.1 M aqueous potassium bisulfate (3×100 mL). The organic phase is separated, dried over anhydrous magnesium sulfate, filtered, and concentrated in vacuo to afford the title compound (151) as a white solid.

Example 122

Synthesis of 3-{N-(1'-Butanoyloxyethoxy)carbonyl-N-[1(R)-(3,4-dichlorophenyl)ethyl]amino}propyl(cyclohexylmethyl)phosphinic Acid (152)

Following the procedure of Example 121 and replacing compound (17) with compound (18) affords the title compound (152) as a white solid.

Example 123

Synthesis of 3-{N-(1'-Pivaloyloxyethoxy)carbonyl-N-[1(R)-(3,4-dichlorophenyl)ethyl]amino}propyl(cyclohexylmethyl)phosphinic Acid (153)

Following the procedure of Example 121 and replacing compound (17) with compound (19) affords the title compound (153) as a white solid.

Example 124

Synthesis of 3-{N-(1'-Cyclohexanoyloxyethoxy)carbonyl-N-[1(R)-(3,4-dichlorophenyl)ethyl]amino}propyl(cyclohexylmethyl)phosphinic Acid (154)

Following the procedure of Example 121 and replacing compound (17) with compound (20) affords the title compound (154) as a white solid.

Example 125

Synthesis of 3-{N-(Isobutanoyloxymethoxy]carbonyl-N-[1(R)-(3,4-dichlorophenyl)ethyl]amino}propyl(cyclohexylmethyl)phosphinic Acid (155)

Following the procedure of Example 121 and replacing compound (17) with compound (21) affords the title compound (155) as a white solid.

Example 126

Synthesis of 3-{N-(Butanoyloxymethoxy)carbonyl-N-[1(R)-(3,4-dichlorophenyl)ethyl]amino}propyl(cyclohexylmethyl)phosphinic Acid (156)

Following the procedure of Example 121 and replacing compound (17) with compound (22) affords the title compound (156) as a white solid.

Example 127

Synthesis of 3-{N-(Pivaloyloxymethoxy)carbonyl-N-[1(R)-(3,4-dichlorophenyl)ethyl]amino}propyl (cyclohexylmethyl)phosphinic Acid (157)

Following the procedure of Example 121 and replacing compound (17) with compound (23) affords the title compound (157) as a white solid.

Example 128

Synthesis of 3-{N-(Cyclohexanoyloxymethoxy)carbonyl-N-[1(R)-(3,4-dichlorophenyl)ethyl]amino}propyl(cyclohexylmethyl)phosphinic Acid (158)

Following the procedure of Example 121 and replacing compound (17) with compound (24) affords the title compound (158) as a white solid.

Example 129

Synthesis of 3-{N-((1'R)-Isobutanoyloxyisobutoxy)carbonyl-N-[1(R)-(3,4-dichlorophenyl)ethyl]amino}propyl(cyclohexylmethyl)phosphinic Acid (159)

To a 3 L three necked round bottom flask fitted with a mechanical stirrer, temperature probe, and nitrogen inlet is added compound (25) (100 mmol), 3-{N-[1(R)-(3,4-dichlorophenyl)ethyl]amino}-propyl(cyclohexylmethyl)phosphinic acid (100 mmol), THF (1 L), and water (100 mL). The suspension is stirred under a nitrogen atmosphere at 18-20° C. for 4 h during which time the reaction mixture becomes homogeneous. The THF is removed in vacuo and the reaction mixture is diluted with methyl tert-butyl ether (250 mL) and washed with 1N HCl (1×500 mL) and water (2×200 mL). The organic phase is separated and concentrated in vacuo to leave a white solid. The solid is purified by flash chromatography to afford the product (159) as a white solid.

Example 130

Synthesis of 3-{N-((1'S)-Isobutanoyloxyisobutoxy)carbonyl-N-[1(R)-(3,4-dichlorophenyl)ethyl]amino}propyl(cyclohexylmethyl)phosphinic Acid (160)

Following the procedure of Example 129 and replacing compound (25) with compound (28) affords the title compound (160) as a white solid.

Example 131

Synthesis of 3-{N-(1'-Isobutanoyloxyethoxy)carbonyl-N-[1(R)-(3,4-dichlorophenyl)ethyl]amino}-(2R)-hydroxypropyl(cyclohexylmethyl)phosphinic Acid (161)

Following the procedure of Example 121 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2R)-hydroxypropyl(cyclohexylmethyl)phosphinic acid affords the title compound (161) as a white solid.

Example 132

Synthesis of 3-{N-(1'-Butanoyloxyethoxy)carbonyl-N-[1(R)-(3,4-dichlorophenyl)ethyl]amino}-(2R)-hydroxypropyl(cyclohexylmethyl)phosphinic Acid (162)

Following the procedure of Example 122 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2R)-hydroxypropyl(cyclohexylmethyl)phosphinic acid affords the title compound (162) as a white solid.

Example 133

Synthesis of 3-{N-(1'-Pivaloyloxyethoxy)carbonyl-N-[1(R)-(3,4-dichlorophenyl)ethyl]amino}-(2R)-hydroxypropyl(cyclohexylmethyl)phosphinic Acid (163)

Following the procedure of Example 123 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2R)-hydroxypropyl(cyclohexylmethyl)phosphinic acid affords the title compound (163) as a white solid.

Example 134

Synthesis of 3-{N-(1'-Cyclohexanoyloxyethoxy)carbonyl-N-[1(R)-(3,4-dichlorophenyl)ethyl]amino}-(2R)-hydroxypropyl(cyclohexylmethyl)phosphinic Acid (164)

Following the procedure of Example 124 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2R)-hydroxypropyl(cyclohexylmethyl)phosphinic acid affords the title compound (164) as a white solid.

Example 135

Synthesis of 3-{N-(Isobutanoyloxymethoxy)carbonyl-N-[1(R)-(3,4-dichlorophenyl)ethyl]amino}-(2R)-hydroxypropyl(cyclohexylmethyl)phosphinic Acid (165)

Following the procedure of Example 125 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2R)-hydroxypropyl(cyclohexylmethyl)phosphinic acid affords the title compound (165) as a white solid.

Example 136

Synthesis of 3-{N-(Butanoyloxymethoxy)carbonyl-N-[1(R)-(3,4-dichlorophenyl)ethyl]amino}-(2R)-hydroxypropyl(cyclohexylmethyl)phosphinic Acid (166)

Following the procedure of Example 126 and replacing 3-{N-[1(R)-(3,4-dichlorophenyl)ethyl]amino}-propyl(cyclohexylmethyl)phosphinic acid with 3-{N-[1(R)-(3,4-

Example 137

Synthesis of 3-{N-(Pivaloyloxymethoxy)carbonyl-N-[1(R)-(3,4-dichlorophenyl)ethyl]amino}-(2R)-hydroxypropyl(cyclohexylmethyl)phosphinic Acid (167)

Following the procedure of Example 127 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2R)-hydroxypropyl(cyclohexylmethyl)phosphinic acid affords the title compound (167) as a white solid.

Example 138

Synthesis of 3-{N-(Cyclohexanoyloxymethoxy)carbonyl-N-[1(R)-(3,4-dichlorophenyl)ethyl]amino}-(2R)-hydroxypropyl(cyclohexylmethyl)phosphinic Acid (168)

Following the procedure of Example 128 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2R)-hydroxypropyl(cyclohexylmethyl)phosphinic acid affords the title compound (168) as a white solid.

Example 139

Synthesis of 3-{N-((1'R)-Isobutanoyloxyisobutoxy)carbonyl-N-[1(R)-(3,4-dichlorophenyl)ethyl]amino}-(2R)-hydroxypropyl(cyclohexylmethyl)phosphinic Acid (169)

Following the procedure of Example 129 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2R)-hydroxypropyl(cyclohexylmethyl)phosphinic acid affords the title compound (169) as a white solid.

Example 140

Synthesis of 3-{N-((1'S)-Isobutanoyloxyisobutoxy)carbonyl-N-[1(R)-(3,4-dichlorophenyl)ethyl]amino}-(2R)-hydroxypropyl(cyclohexylmethyl)phosphinic Acid (170)

Following the procedure of Example 130 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2R)-hydroxypropyl(cyclohexylmethyl)phosphinic acid affords the title compound (170) as a white solid.

Example 141

Synthesis of 3-{N-(1'-Isobutanoyloxyethoxy)carbonyl-N-[1(R)-(3,4-dichlorophenyl)ethyl]amino}-(2S)-hydroxypropyl(cyclohexylmethyl)phosphinic Acid (171)

Following the procedure of Example 121 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2S)-hydroxypropyl(cyclohexylmethyl)phosphinic acid affords the title compound (171) as a white solid.

Example 142

Synthesis of 3-{N-(1'-Butanoyloxyethoxy)carbonyl-N-[1(R)-(3,4-dichlorophenyl)ethyl]amino}-(2S)-hydroxypropyl(cyclohexylmethyl)phosphinic Acid (172)

Following the procedure of Example 122 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2S)-hydroxypropyl(cyclohexylmethyl)phosphinic acid affords the title compound (172) as a white solid.

Example 143

Synthesis of 3-{N-(1'-Pivaloyloxyethoxy)carbonyl-N-[1(R)-(3,4-dichlorophenyl)ethyl]amino}-(2S)-hydroxypropyl(cyclohexylmethyl)phosphinic Acid (173)

Following the procedure of Example 123 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2S)-hydroxypropyl(cyclohexylmethyl)phosphinic acid affords the title compound (173) as a white solid.

Example 144

Synthesis of 3-{N-(1'-Cyclohexanoyloxyethoxy)carbonyl-N-[1(R)-(3,4-dichlorophenyl)ethyl]amino}-(2S)-hydroxypropyl(cyclohexylmethyl)phosphinic Acid (174)

Following the procedure of Example 124 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2S)-hydroxypropyl(cyclohexylmethyl)phosphinic acid affords the title compound (174) as a white solid.

Example 145

Synthesis of 3-{N-(Isobutanoyloxymethoxy]carbonyl-N-[1(R)-(3,4-dichlorophenyl)ethyl]amino}-(2S)-hydroxypropyl(cyclohexylmethyl)phosphinic Acid (175)

Following the procedure of Example 125 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2S)-hydroxypropyl(cyclohexylmethyl)phosphinic acid affords the title compound (175) as a white solid.

Example 146

Synthesis of 3-{N-(Butanoyloxymethoxy)carbonyl-N-[1(R)-(3,4-dichlorophenyl)ethyl]amino}-(2S)-hydroxypropyl(cyclohexylmethyl)phosphinic Acid (176)

Following the procedure of Example 126 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2S)-hydroxypropyl(cyclohexylmethyl)phosphinic acid affords the title compound (176) as a white solid.

Example 147

Synthesis of 3-{N-(Pivaloyloxymethoxy)carbonyl-N-[1(R)-(3,4-dichlorophenyl)ethyl]amino}-(2S)-hydroxypropyl(cyclohexylmethyl)phosphinic Acid (177)

Following the procedure of Example 127 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2S)-hydroxypropyl(cyclohexylmethyl)phosphinic acid affords the title compound (177) as a white solid.

Example 148

Synthesis of 3-{N-(Cyclohexanoyloxymethoxy)carbonyl-N-[1(R)-(3,4-dichlorophenyl)ethyl]amino}-(2S)-hydroxypropyl(cyclohexylmethyl)phosphinic Acid (178)

Following the procedure of Example 128 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2S)-hydroxypropyl(cyclohexylmethyl)phosphinic acid affords the title compound (178) as a white solid.

Example 149

Synthesis of 3-{N-((1'R)-Isobutanoyloxyisobutoxy)carbonyl-N-[1(R)-(3,4-dichlorophenyl)ethyl]amino}-(2S)-hydroxypropyl(cyclohexylmethyl)phosphinic Acid (179)

Following the procedure of Example 129 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2S)-hydroxypropyl(cyclohexylmethyl)phosphinic acid affords the title compound (179) as a white solid.

Example 150

Synthesis of 3-{N-((1'S)-Isobutanoyloxyisobutoxy)carbonyl-N-[1(R)-(3,4-dichlorophenyl)ethyl]amino}-(2S)-hydroxypropyl(cyclohexylmethyl)phosphinic Acid (180)

Following the procedure of Example 130 and replacing 3-{N-[1(R)-(3,4-dichlorophenyl)ethyl]amino}-propyl(cyclohexylmethyl)phosphinic acid with 3-{N-[1(R)-(3,4-dichlorophenyl)ethyl]amino}-(2S)-hydroxypropyl(cyclohexylmethyl)phosphinic acid affords the title compound (180) as a white solid.

Example 151

Synthesis of 3-{N-(1'-Isobutanoyloxyethoxy)carbonyl-N-[1(S)-(3,4-dichlorophenyl)ethyl]amino}propyl(cyclohexylmethyl)phosphinic Acid (181)

To a solution of 3-{N-[1(S)-(3,4-dichlorophenyl)ethyl]amino}-propyl(cyclohexylmethyl)phosphinic acid (10 mmol) and sodium bicarbonate (20 mmol) in water (40 mL) is added a solution of compound (17) (10 mmol) in acetonitrile (20 mL) over 1 min. The reaction is stirred at ambient temperature for 16 h. The reaction mixture is diluted with diethyl ether (100 mL) and washed with 0.1 M aqueous potassium bisulfate (3×100 mL). The organic phase is separated, dried over anhydrous magnesium sulfate, filtered, and concentrated in vacuo to afford the title compound (181) as a white solid.

Example 152

Synthesis of 3-{N-(1'-Butanoyloxyethoxy)carbonyl-N-[1(S)-(3,4-dichlorophenyl)ethyl]amino}propyl(cyclohexylmethyl)phosphinic Acid (182)

Following the procedure of Example 151 and replacing compound (17) with compound (18) affords the title compound (182) as a white solid.

Example 153

Synthesis of 3-{N-(1'-Pivaloyloxyethoxy)carbonyl-N-[1(S)-(3,4-dichlorophenyl)ethyl]amino}propyl(cyclohexylmethyl)phosphinic Acid (183)

Following the procedure of Example 151 and replacing compound (17) with compound (19) affords the title compound (183) as a white solid.

Example 154

Synthesis of 3-{N-(1'-Cyclohexanoyloxyethoxy)carbonyl-N-[1(S)-(3,4-dichlorophenyl)ethyl]amino}propyl(cyclohexylmethyl)phosphinic Acid (184)

Following the procedure of Example 151 and replacing compound (17) with compound (20) affords the title compound (184) as a white solid.

Example 155

Synthesis of 3-{N-(Isobutanoyloxymethoxy)carbonyl-N-[1(S)-(3,4-dichlorophenyl)ethyl]amino}propyl(cyclohexylmethyl)phosphinic Acid (185)

Following the procedure of Example 151 and replacing compound (17) with compound (21) affords the title compound (185) as a white solid.

Example 156

Synthesis of 3-{N-(Butanoyloxymethoxy)carbonyl-N-[1(S)-(3,4-dichlorophenyl)ethyl]amino}propyl (cyclohexylmethyl)phosphinic Acid (186)

Following the procedure of Example 151 and replacing compound (17) with compound (22) affords the title compound (186) as a white solid.

Example 157

Synthesis of 3-{N-(Pivaloyloxymethoxy)carbonyl-N-[1(S)-(3,4-dichlorophenyl)ethyl]amino}propyl (cyclohexylmethyl)phosphinic Acid (187)

Following the procedure of Example 151 and replacing compound (17) with compound (23) affords the title compound (187) as a white solid.

Example 158

Synthesis of 3-{N-(Cyclohexanoyloxymethoxy)carbonyl-N-[1(S)-(3,4-dichlorophenyl)ethyl]amino}propyl(cyclohexylmethyl)phosphinic Acid (188)

Following the procedure of Example 151 and replacing compound (17) with compound (24) affords the title compound (188) as a white solid.

Example 159

Synthesis of 3-{N-((1'R)-Isobutanoyloxyisobutoxy)carbonyl-N-[1(S)-(3,4-dichlorophenyl)ethyl]amino}propyl(cyclohexylmethyl)phosphinic Acid (189)

To a 3 L three necked round bottom flask fitted with a mechanical stirrer, temperature probe, and nitrogen inlet is added compound (25) (100 mmol), 3-{N-[1(S)-(3,4-dichlorophenyl)ethyl]amino}-propyl(cyclohexylmethyl)phosphinic acid (100 mmol), THF (1 L), and water (100 mL). The suspension is stirred under a nitrogen atmosphere at 18-20° C. for 4 h during which time the reaction mixture becomes homogeneous. The THF is removed in vacuo and the reaction mixture is diluted with methyl tert-butyl ether (250 mL) and washed with 1N HCl (1×500 mL) and water (2×200 mL). The organic phase is separated and concentrated in vacuo to leave a white solid. The solid is purified by flash chromatography to afford the product (189) as a white solid.

Example 160

Synthesis of 3-{N-((1'S)-Isobutanoyloxyisobutoxy)carbonyl-N-[1(S)-(3,4-dichlorophenyl)ethyl]amino}propyl(cyclohexylmethyl)phosphinic Acid (190)

Following the procedure of Example 159 and replacing compound (25) with compound (28) affords the title compound (190) as a white solid.

Example 161

Synthesis of 3-{N-(1'-Isobutanoyloxyethoxy)carbonyl-N-[1(S)-(3,4-dichlorophenyl)ethyl]amino}-(2R)-hydroxypropyl(cyclohexylmethyl)phosphinic Acid (191)

Following the procedure of Example 151 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2R)-hydroxypropyl(cyclohexylmethyl)phosphinic acid affords the title compound (191) as a white solid.

Example 162

Synthesis of 3-{N-(1'-Butanoyloxyethoxy)carbonyl-N-[1(S)-(3,4-dichlorophenyl)ethyl]amino}-(2R)-hydroxypropyl(cyclohexylmethyl)phosphinic Acid (192)

Following the procedure of Example 152 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2R)-hydroxypropyl(cyclohexylmethyl)phosphinic acid affords the title compound (192) as a white solid.

Example 163

Synthesis of 3-{N-(1'-Pivaloyloxyethoxy)carbonyl-N-[1(S)-(3,4-dichlorophenyl)ethyl]amino}-(2R)-hydroxypropyl(cyclohexylmethyl)phosphinic Acid (193)

Following the procedure of Example 153 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2R)-hydroxypropyl(cyclohexylmethyl)phosphinic acid affords the title compound (193) as a white solid.

Example 164

Synthesis of 3-{N-(1'-Cyclohexanoyloxyethoxy)carbonyl-N-[1(S)-(3,4-dichlorophenyl)ethyl]amino}-(2R)-hydroxypropyl(cyclohexylmethyl)phosphinic Acid (194)

Following the procedure of Example 154 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2R)-hydroxypropyl(cyclohexylmethyl)phosphinic acid affords the title compound (194) as a white solid.

Example 165

Synthesis of 3-{N-(Isobutanoyloxymethoxy)carbonyl-N-[1(S)-(3,4-dichlorophenyl)ethyl]amino}-(2R)-hydroxypropyl(cyclohexylmethyl)phosphinic Acid (195)

Following the procedure of Example 155 and replacing 3-{N-[1(S)-(3,4-dichlorophenyl)ethyl]amino}-propyl(cyclohexylmethyl)phosphinic acid with 3-{N-[1(S)-(3,4- dichlorophenyl)ethyl]amino}-(2R)-hydroxypropyl(cyclohexylmethyl)phosphinic acid affords the title compound (195) as a white solid.

Example 166

Synthesis of 3-{N-(Butanoyloxymethoxy)carbonyl-N-[1(S)-(3,4-dichlorophenyl)ethyl]amino}-(2R)-hydroxypropyl(cyclohexylmethyl)phosphinic Acid (196)

Following the procedure of Example 156 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2R)-hydroxypropyl(cyclohexylmethyl)phosphinic acid affords the title compound (196) as a white solid.

Example 167

Synthesis of 3-{N-(Pivaloyloxymethoxy)carbonyl-N-[1(S)-(3,4-dichlorophenyl)ethyl]amino}-(2R)-hydroxypropyl(cyclohexylmethyl)phosphinic Acid (197)

Following the procedure of Example 157 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2R)-hydroxypropyl(cyclohexylmethyl)phosphinic acid affords the title compound (197) as a white solid.

Example 168

Synthesis of 3-{N-(Cyclohexanoyloxymethoxy)carbonyl-N-[1(S)-(3,4-dichlorophenyl)ethyl]amino}-(2R)-hydroxypropyl(cyclohexylmethyl)phosphinic Acid (198)

Following the procedure of Example 158 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2R)-hydroxypropyl(cyclohexylmethyl)phosphinic acid affords the title compound (198) as a white solid.

Example 169

Synthesis of 3-{N-((1'R)-Isobutanoyloxyisobutoxy)carbonyl-N-[1(S)-(3,4-dichlorophenyl)ethyl]amino}-(2R)-hydroxypropyl(cyclohexylmethyl)phosphinic Acid (199)

Following the procedure of Example 159 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2R)-hydroxypropyl(cyclohexylmethyl)phosphinic acid affords the title compound (199) as a white solid.

Example 170

Synthesis of 3-{N-((1'S)-Isobutanoyloxyisobutoxy)carbonyl-N-[1(S)-(3,4-dichlorophenyl)ethyl]amino}-(2R)-hydroxypropyl(cyclohexylmethyl)phosphinic Acid (200)

Following the procedure of Example 160 and replacing 3-{N-[1(S)-(3,4-dichlorophenyl)ethyl]amino}-propyl(cyclohexylmethyl)phosphinic acid with 3-{N-[1(s)-(3,4-dichlorophenyl)ethyl]amino}-(2R)-hydroxypropyl(cyclohexylmethyl)phosphinic acid affords the title compound (200) as a white solid.

Example 171

Synthesis of 3-{N-(1'-Isobutanoyloxyethoxy)carbonyl-N-[1(S)-(3,4-dichlorophenyl)ethyl]amino}-(2S)-hydroxypropyl(cyclohexylmethyl)phosphinic Acid (201)

Following the procedure of Example 151 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2S)-hydroxypropyl(cyclohexylmethyl)phosphinic acid affords the title compound (201) as a white solid.

Example 172

Synthesis of 3-{N-(1'-Butanoyloxyethoxy)carbonyl-N-[1(S)-(3,4-dichlorophenyl)ethyl]amino}-(2S)-hydroxypropyl(cyclohexylmethyl)phosphinic Acid (202)

Following the procedure of Example 152 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2S)-hydroxypropyl(cyclohexylmethyl)phosphinic acid affords the title compound (202) as a white solid.

Example 173

Synthesis of 3-{N-(1'-Pivaloyloxyethoxy)carbonyl-N-[1(S)-(3,4-dichlorophenyl)ethyl]amino}-(2S)-hydroxypropyl(cyclohexylmethyl)phosphinic Acid (203)

Following the procedure of Example 153 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2S)-hydroxypropyl(cyclohexylmethyl)phosphinic acid affords the title compound (203) as a white solid.

Example 174

Synthesis of 3-{N-(1'-Cyclohexanoyloxyethoxy)carbonyl-N-[1(S)-(3,4-dichlorophenyl)ethyl]amino}-(2S)-hydroxypropyl(cyclohexylmethyl)phosphinic Acid (204)

Following the procedure of Example 154 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2S)-hydroxypropyl(cyclohexylmethyl)phosphinic acid affords the title compound (204) as a white solid.

Example 175

Synthesis of 3-{N-(Isobutanoyloxymethoxy)carbonyl-N-[1(S)-(3,4-dichlorophenyl)ethyl]amino}-(2S)-hydroxypropyl(cyclohexylmethyl)phosphinic Acid (205)

Following the procedure of Example 155 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2S)-hydroxypropyl(cyclohexylmethyl)phosphinic acid affords the title compound (205) as a white solid.

Example 176

Synthesis of 3-{N-(Butanoyloxymethoxy)carbonyl-N-[1(S)-(3,4-dichlorophenyl)ethyl]amino}-(2S)-hydroxypropyl(cyclohexylmethyl)phosphinic Acid (206)

Following the procedure of Example 156 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2S)-hydroxypropyl(cyclohexylmethyl)phosphinic acid affords the title compound (206) as a white solid.

Example 177

Synthesis of 3-{N-(Pivaloyloxymethoxy)carbonyl-N-[1(S)-(3,4-dichlorophenyl)ethyl]amino}-(2S)-hydroxypropyl(cyclohexylmethyl)phosphinic Acid (207)

Following the procedure of Example 157 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2S)-hydroxypropyl(cyclohexylmethyl)phosphinic acid affords the title compound (207) as a white solid.

Example 178

Synthesis of 3-{N-(Cyclohexanoyloxymethoxy)carbonyl-N-[1(S)-(3,4-dichlorophenyl)ethyl]amino}-(2S)-hydroxypropyl(cyclohexylmethyl)phosphinic Acid (208)

Following the procedure of Example 158 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2S)-hydroxypropyl(cyclohexylmethyl)phosphinic acid affords the title compound (208) as a white solid.

Example 179

Synthesis of 3-{N-((1'R)-Isobutanoyloxyisobutoxy)carbonyl-N-[1(S)-(3,4-dichlorophenyl)ethyl]amino}-(2S)-hydroxypropyl(cyclohexylmethyl)phosphinic Acid (209)

Following the procedure of Example 159 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2S)-hydroxypropyl(cyclohexylmethyl)phosphinic acid affords the title compound (209) as a white solid.

Example 180

Synthesis of 3-{N-((1'S)-Isobutanoyloxyisobutoxy)carbonyl-N-[1(S)-(3,4-dichlorophenyl)ethyl]amino}-(2S)-hydroxypropyl(cyclohexylmethyl)phosphinic Acid (210)

Following the procedure of Example 160 and replacing 3-{N-[1(S)-(3,4-dichlorophenyl)ethyl]amino}-propyl(cyclohexylmethyl)phosphinic acid with 3-{N-[1(S)-(3,4-dichlorophenyl)ethyl]amino}-(2S)-hydroxypropyl(cyclohexylmethyl)phosphinic acid affords the title compound (210) as a white solid.

Example 181

Synthesis of 3-{[1-Benzoyloxyethoxy]carbonylamino}propyl(n-butyl)phosphinic Acid (211)

Following the procedure of Example 1 and replacing compound (17) with compound (214) afforded the title compound (211) as a white solid. $^1$H-NMR (400 MHz, CDCl$_3$): δ 8.03 (d, J=8 Hz, 2H), 7.53 (t, J=8.8 Hz, 1H), 7.41 (t, J=8 Hz, 2H), 7.06 (q, J=5.2 Hz, 1H), 3.48 (s, 1H), 3.25-3.28 (m, 2H), 1.53-1.81 (m, 10H), 1.36-1.41 (m, 2H), 0.9 (t, J=7.2 Hz, 3H). Phosphorus (162 MHz, CD$_3$OD) 60.33. MS (ESI) m/z 372 (M+H)$^+$.

Example 182

Synthesis of 3-{[1-Benzoyloxymethoxy]carbonylamino}propyl(n-butyl)phosphinic Acid (212)

Following the procedure of Example 1 and replacing compound (17) with compound (216) afforded the title compound (212) as a white solid. $^1$H-NMR (400 MHz, CDCl$_3$): δ 8.03 (dd, J=1.6 Hz, 1.6 Hz, 2H), 7.55 (t, J=7.2 Hz, 1H), 7.41 (t, J=8 Hz, 2H), 5.95 (s, 2H), 3.28 (t, J=6.8 Hz, 2H), 1.80-1.84 (m, 2H), 1.61-1.74 (m, 4H 0, 1.51-1.53 (m, 2H), 1.34-1.39 (m, 2H), 0.88 (t, J=7.2 Hz, 3H). Phosphorus (162 MHz, CD$_3$OD) 59.50. MS (ESI) m/z 358 (M+H)$^+$.

Example 183

Synthesis of 3-{(Isobutanoyloxyisobutoxy]carbonylamino}propyl(n-butyl)phosphinic Acid Sodium Salt (213)

Compound 39 was dissolved in a mixture of water and acetonitrile, an aqueous solution of 1 eq. NaHCO$_3$ was added, the mixture stirred for about 10 min, and lyophilized to afford the title compound (213). $^1$H-NMR (400 MHz, CDCl$_3$): δ 6.55 (d, J=4.8 Hz, 1H), 3.10 (t, J=6.4 Hz, 2H), 2.53-2.56 (m, 1H), 1.97-2.00 (m, 1H), 1.79-1.83 (m, 2H), 1.70-1.74 (m, 2H), 1.53-1.58 (m, 2H), 1.37-1.43 (m, 2H), 1.15 (t, J=6.8 Hz, 6H), 0.90 (t, J=7.2 Hz, 9H).

Phosphorus (162 MHz, CD$_3$OD) 60.36; MS (ESI) m/z 366 (M+H)$^+$.

Example 184

Synthesis of 3-{(Butanoyloxyethoxy] carbonylamino}propyl(n-butyl)phosphinic Acid Sodium Salt (214)

Following the procedure of Example 1 and replacing compound (17) with compound (18) afforded 3-{[1-butanoyloxyethoxy]carbonylamino}propyl(n-butyl)phosphinic acid. 3-{[1-Butanoyloxyethoxy]carbonylamino}propyl(n-butyl) phosphinic acid was dissolved in a mixture of water and acetonitrile, an aqueous solution of 1 eq. NaHCO$_3$ was added, the mixture stirred for about 10 min, and lyophilized to afford the title compound (214). $^1$H-NMR (400 MHz, CD$_3$OD): δ 6.75-6.71 (q, J=5.6, 16.4 Hz, 1H), 3.15-3.08 (m, 2H), 2.29-2.25 (d, J=1.6 Hz, 2H), 1.73-1.35 (m, 16H), 0.95-0.90 (q, J=7.6 Hz, 3H). Phosphorus (162 MHz, CD$_3$OD): 42.747; MS (ESI) m/z 337 (M+H)$^+$.

Example 185

Methods for Determination of Enzmmatic Cleavage of Prodrugs in Vitro

The stabilities of prodrugs were evaluated in one or more in vitro systems using a variety of tissue preparations following methods known in the art. The chemical stability of prodrugs in aqueous buffers at a pH of 2.0, 7.4, and 8.0 were also measured. Tissues were obtained from commercial sources (e.g., Pel-Freez Biologicals, Rogers, Ark., or GenTest Corporation, Woburn, Mass.). Experimental conditions used for the in vitro studies are described in Table 1. Each preparation was incubated with test compound at 37° C. for one hour. Aliquots (50 µL) were removed at 0, 30, and 60 min and quenched with 0.1% trifluoroacetic acid in acetonitrile. Samples were then centrifuged and analyzed by LC/MS/MS. Stability of prodrugs towards specific enzymes (e.g., peptidases, etc.) was also assessed in vitro by incubation with the purified enzyme.

Pancreatin Stability: Stability studies were conducted by incubating prodrug (5 µM) with 1% (w/v) pancreatin (Sigma, P-1625, from porcine pancreas) in 0.025 M Tris buffer containing 0.5 M NaCl (pH 7.5) at 37° C. for 60 min. The reaction was stopped by addition of 2 volumes of methanol. After centrifugation at 14,000 rpm for 10 min, the supernatant was removed and analyzed by LC/MS/MS.

Caco-2 Homogenate S9 Stability: Caco-2 cells were grown for 21 days prior to harvesting. Culture medium was removed and cell monolayers were rinsed and scraped off into ice-cold 10 mM sodium phosphate/0.15 M potassium chloride, pH 7.4. Cells were lysed by sonication at 4° C. using a probe sonicator. Lysed cells were then transferred into 1.5 mL centrifuge vials and centrifuged at 9,000 g for 20 min at 4° C. The resulting supernatant (Caco-2 cell homogenate S9 fraction) was aliquoted into 0.5 mL vials and stored at −80° C. until used.

TABLE 1

Conditions for Prodrug In Vitro Metabolism Studies

| Preparation | Substrate Concentration | Cofactors |
|---|---|---|
| Rat Plasma | 2.0 µM | None |
| Human Plasma | 2.0 µM | None |
| Rat Liver S9 (0.5 mg/mL) | 2.0 µM | NADPH* |
| Human Liver S9 (0.5 mg/mL) | 2.0 µM | NADPH* |
| Human Intestine S9 (0.5 mg/mL) | 2.0 µM | NADPH* |
| CarboxypeptidaseA (10 units/mL) | 2.0 µM | None |
| Caco-2 Homogenate | 5.0 µM | None |
| Pancreatin | 5.0 µM | None |

*NADPH generating system, e.g., 1.3 mM NADP$^+$, 3.3 mM glucose-6-phosphate, 0.4 U/mL glucose-6-phosphate dehydrogenase, 3.3 mM magnesium chloride and 0.95 mg/mL potassium phosphate, pH 7.4.

For stability studies, prodrug (5 µM) was incubated in Caco-2 homogenate S9 fraction (0.5 mg protein per mL) for 60 min at 37° C. Concentrations of intact prodrug and released tranexamic acid were determined at zero time and 60 min using LC/MS/MS.

pH-Dependent Stability: The long-term pH-dependent stability of tranexamic acid prodrug at 37° C. was measured by LC/MS/MS at five different representative pH values from pH 2.0 to pH 8.0 was determined. The test concentration was 5 µM. The amount of remaining prodrug and the amount of tranexamic acid released from the prodrug was determined at 0 hour and after 24 hours.

Compounds 31, 35, 39/40, 211, and 212, for example, showed good stability from pH 2 to pH 8, and are hydrolyzed to release the corresponding 3-aminopropylphosphinic acid analogs in the presence of the tissue preparations.

Example 186

In Vitro Determination of Caco-2 Cellular Permeability of Prodrugs

The passive permeability of the prodrugs of the present disclosure can be assessed in vitro using standard methods well known in the art (See, e.g., Stewart, et al., *Pharm. Res.*, 1995, 12, 693). For example, passive permeability can be evaluated by examining the flux of a prodrug across a cultured polarized cell monolayer (e.g., Caco-2 cells).

Caco-2 cells are obtained from continuous culture (passage less than 28) were seeded at high density onto Transwell polycarbonate filters. Cells are maintained with DMEM/10% fetal bovine serum, 1 mM nonessential amino acids, and 6 mM L-Gln, 5% CO$_2$/95% O$_2$, at 37° C. until the day of the experiment. Permeability studies are conducted at pH 6.5 apically (in 50 mM MES buffer containing 1 mM CaCl$_2$, 1 mM MgCl$_2$, 150 mM NaCl, 3 mM KCl, 1 mM NaH$_2$PO$_4$, 5 mM glucose) and pH 7.4 basolaterally (in Hanks' balanced salt solution containing 10 mM HEPES) in the presence of efflux pump inhibitors (250 µM MK-571 and 250 µM Verapamil). Inserts are placed in 12 or 24 well plates containing buffer and incubated for 30 min at 37° C. Prodrug (200 µM) is added to the apical or basolateral compartment (donor) and concentrations of prodrug and/or released parent drug in the opposite compartment (receiver) are determined at intervals over 1 hour using LC/MS/MS. Values of apparent permeability (P$_{app}$) are calculated using the equation:

$$P_{app} = V_r(dC/dt)/(AC_o)$$

where V$_r$ is the volume of the receiver compartment in mL; dC/dt is the total flux of prodrug and parent drug (µM/sec), determined from the slope of the plot of concentration in the receiver compartment versus time; $C_0$ is the initial concentration of prodrug in μM; and A is the surface area of the membrane in cm². Prodrugs with significant transcellular permeability can exhibit a value of $P_{app}$ of $\geq 1 \times 10^{-6}$, a value of $P_{app}$ of $\geq 1 \times 10^{-5}$ cm/sec, or a value of $P_{app}$ of $\geq 5 \times 10^{-5}$ cm/sec. Prodrugs having a high $P_{app}$ should be well absorbed from the intestine. Prodrugs for which the apical-to-basolateral permeabilities exceeds their basolateral-to-apical permeability may be substrates for active transport mechanisms present in the apical membrane of Caco-2 cells (although some component of this transcellular permeability may also be mediated by passive diffusion).

Example 187

Bioavailability of Prodrugs and Metabolites Thereof Following Intracolonic Administration in Rats Step A: Administration Protocol Rats are obtained commercially and are pre-cannulated in the both the ascending colon and the jugular vein. Animals are conscious at the time of the experiment. All animals are fasted overnight and until 4 hours post-dosing of a prodrug of 3-aminopropylphosphinic or analog thereof. 3-aminopropylphosphinic or analog thereof or the corresponding prodrug is administered as a solution (in water) directly into the colon via the cannula at a dose equivalent to about 75 mg or other appropriate dose of a 3-aminopropylphosphinic or analog thereof per kg body weight. Blood samples (0.3 mL) are obtained from the jugular cannula at intervals over 8 hours and are quenched immediately by addition of sodium metabisulfite to prevent oxidation of the 3-aminopropylphosphinic or analog thereof. Blood is then further quenched with methanol/perchloric acid to prevent hydrolysis of the prodrug. Blood samples are analyzed as described in Steps B and C.

Step B: Sample Preparation for Colonically Absorbed Drug

300 μL of methanol is added to 1.5 mL tubes. Rat blood (100 μL) is collected at different times into the tubes and vortexed to mix. 90 μL of rat blood is quenched with 300 μL methanol. 10 μL of a standard stock solution containing an α-amino acid (0.04, 0.2, 1, 5, 25, and 100 μg/1 mL) and 20 μL of p-chlorophenylalanine is added to 90 μL of rat blood to make up a final calibration standard (0.004, 0.02, 0.1, 0.5, 2.5, and 10 μg/mL). Samples are vortexed and centrifuged at 3400 rpm for 20 min. The supernatant is analyzed by LC/MS/MS.

Step C: LC/MS/MS Analysis

An API 4000 LC/MS/MS spectrometer equipped with Agilent 1100 binary pumps and a CTC HTS-PAL autosampler are used in the analysis. A ThermoHypersil-Keystone Betasil C18 100×4.6 mm, 5 μM column is used during the analysis. The mobile phase is 0.1% formic acid in water (A) and 0.1% formic acid in acetonitrile (B). The flow rate is 1.2 mL/min. The gradient condition is: 1% B for 0.5 min, then to 95% B for 1.8 min, and maintained at 95% B for 1.7 min. Then the mobile phase is returned to 1% B for 2.5 min. A TurboIonSpray source is used on the API 4000. The analysis is done in either negative ion mode or positive ion mode as appropriate and the MRM transition for each analyte is optimized using standard solution. 20 μL of the samples are injected. Non-compartmental analysis is performed using WinNonlin software (v. 3.1 Professional Version, Pharsight Corporation, Mountain View, Calif.) on individual animal profiles. Summary statistics on major parameter estimates is performed for $C_{max}$ (peak observed concentration following dosing), $T_{max}$ (time to maximum concentration is the time at which the peak concentration was observed), $AUC_{(0-t)}$ (area under the plasma concentration-time curve from time zero to last collection time, estimated using the log-linear trapezoidal method), $AUC_{(0-\infty)}$, (area under the plasma concentration time curve from time zero to infinity, estimated using the log-linear trapezoidal method to the last collection time with extrapolation to infinity), and $t_{1/2,z}$ (terminal half-life).

Prodrugs that provide a bioavailability of the corresponding 3-aminopropylphosphinic or analog thereof that is greater than the bioavailability provided by an equimolar dose of the 3-aminopropylphosphinic or analog thereof administered to a patient by the same route (e.g., oral administration) can be useful as therapeutic agents, and more particularly, as sustained release therapeutic agents.

Example 188

Animal Model for Assessing Therapeutic Efficacy of Prodrugs of 3-Aminopropylphosphinic Acid Analogs for Treating Alzheimer's Disease Heterozygous transgenic mice expressing the Swedish AD mutant gene, hAPPK670N, M671L (Tg2576; Hsiao, *Learning & Memory* 2001, 8, 301-308) are used as an animal model of Alzheimer's disease. Animals are housed under standard conditions with a 12:12 light/dark cycle and food and water available ad libitum. Beginning at 9 months of age, mice are divided into two groups. The first two groups of animals receive increasing doses of 3-aminopropylphosphinic acid analog prodrug, over six weeks. The remaining control group receives daily saline injections for six weeks.

Behavioral testing is performed at each drug dose using the same sequence over two weeks in all experimental groups: 1) spatial reversal learning, 2) locomotion, 3) fear conditioning, and 4) shock sensitivity. This order is selected to minimize interference among testing paradigms.

Acquisition of the spatial learning paradigm and reversal learning are tested during the first five days of test compound administration using a water T-maze as described in Bardgett et al., *Brain Res Bull* 2003, 60, 131-142. Mice are habituated to the water T-maze during days 1-3, and task acquisition begins on day 4. On day 4, mice are trained to find the escape platform in one choice arm of the maze until 6 to 8 correct choices are made on consecutive trails. The reversal learning phase is then conducted on day 5. During the reversal learning phase, mice are trained to find the escape platform in the choice arm opposite from the location of the escape platform on day 4. The same performance criterion and inter-trial interval are used as during task acquisition.

Large ambulatory movements are assessed to determine that the results of the spatial reversal learning paradigm are not influenced by the capacity for ambulation. After a rest period of two days, horizontal ambulatory movements, excluding vertical and fine motor movements, are assessed in a chamber equipped with a grid of motion-sensitive detectors on day 8. The number of movements accompanied by simultaneous blocking and unblocking of a detector in the horizontal dimension are measured during a one-hour period.

The animals' capacity for contextual and cued memory is tested using a fear conditioning paradigm beginning on day 9. Testing takes place in a chamber that contains a piece of absorbent cotton soaked in an odor-emitting solution such as mint extract placed below the grid floor. A 5-min, 3 trial 80 db, 2800 Hz tone-foot shock sequence is administered to train the animals on day 9. On day 10, memory for context is tested by returning each mouse to the chamber without exposure to the tone and foot shock, and recording the presence or absence of freezing behavior every 10 seconds for 8 minutes. Freezing is defined as no movement, such as ambulation, sniffing or stereotypy, other than respiration.

On day 11, the animals' response to an alternate context and to the auditory cue is tested. Coconut extract is placed in a cup and the 80 dB tone is presented, but no foot shock is delivered. The presence or absence of freezing in response to the alternate context is then determined during the first 2 minutes of the trial. The tone is then presented continuously for the remaining 8 minutes of the trial, and the presence or absence of freezing in response to the tone is determined.

On day 12, the animals are tested to assess their sensitivity to the conditioning stimulus, i.e., foot shock.

Following the last day of behavioral testing, animals are anesthetized and the brains removed, post-fixed overnight, and sections cut through the hippocampus. The sections are stained to image β-amyloid plaques (see e.g., Dong et al., *Neuroscience* 2004, 127, 601-609).

Data are analyzed using appropriate statistical methods.

Example 189

Animal Model for Assessing Therapeutic Efficacy of Prodrugs of 3-Aminopropylphosphinic Acid Analogs for Treating Depression Forced Swim Test in Rats Male Wistar rats weighting 230-270 g are acclimated to the colony room for a minimum of 1 week, handled daily for at least 4 days and habituated to saline injections for 2 days before the experiments.

Two glass cylinders (20 cm dia×40 cm height) are separated by black opaque partitions and filled with water at about 24° C. to a depth of 30 cm. At this depth a rat cannot stand on the cylinder bottom. The water level is 10 cm from the top. Water is changed before each animal is placed into the water tank. An experimental session consists of two trials. During the conditioning trial, rats are gently placed into the cylinders for 15 min. After the trial, rats are dried and placed into a warm cage with the paper towels for 10-15 min before being returned to their home cages. Twenty-four hours later, for the test trial, animals are placed again into the cylinders for a 5-min test session. Tests are video taped for subsequent quantitative behavioral analysis. The frequency and/or total duration are calculated for each of the following categories: passive/immobile behavior (floating is scored when an animal remains in the water with all four limbs motionless, except for occasional alternate movements of paws and tail necessary to prevent sinking and to keep head/nose above the water); active/mobile behaviors (swimming characterized by rigorous movements with all four legs; paddling characterized by floating with rhythmical simultaneous kicks and occasional pushes off the wall to give speed and direction to the drift), including escape-oriented behaviors (climbing characterized by intense movements with all four limbs, with the two forepaws breaking the surface of the water and being directed against the walls of the cylinder; diving characterized by movements towards the bottom of the cylinder with the rat's head below its hind limbs), and self-directed behaviors (headshakes, vigorous headshakes to get water off the snout and eyes; wiping, rubbing water away from the snout). In addition, at the end of each test trial, fecal boli are counted. A test compound, control, or positive control (e.g., imipramine) is administered prior to the test.

Tail Suspension Test in Mice

Mice are housed in standard laboratory cages and acclimated. Mice are moved from the housing room to the testing area in their home cages and allowed to adapt to the new environment for at least 1 h before testing. Immobility is induced by tail suspension according to the procedure of Steru et al., *Psychopharmacology* 1985, 85, 367-370. Mice are lying individually on a paper adhesive tape, 65 cm above a tabletop. Tape is placed approximately 1 cm from the tip of the tail. Animals are allowed to hang for 6 min and the duration of immobility is recorded. Mice are considered immobile only when hanging passively and completely motionless. Mice from these experiments are used one week later in locomotor activity studies. A test compound, control, or positive control (e.g., imipramine) is administered prior to the test.

Locomotor Activity

The spontaneous locomotor activity of mice is measured in photoresistor actometers (circular cages, 25 cm in dia, 15 cm high, two light sources, two photoresistors), wherein the animals are placed individually 1 h after injection of a test compound. The number of crossings of light beams is measured during the first 30 min of the experimental session. The first measurement is performed 6 min after placing an animal into the actometer.

The spontaneous locomotor activity of rats is measured in photoresistor actometers (40×40×25 cm, two light sources, two photoresistors), where the animals are placed after administration of a test compound. The number of crossings of light beams is measured during the first 30 min of an experimental session. The first measurement is performed 5 min after placing an animal in the actometer.

Example 190

Animal Model for Assessing Therapeutic Efficacy of Prodrugs of 3-Aminopropylphosphinic Acid Analogs for Treating Anxiety A method for assessing the effects of test compounds on anxiety described by Pellow and File, Pharmacol Biochem Behav 1986, 24, 524-529, i.e., the elevated plus-maze test, is used. A plus-maze is consists of two open arms (50×10 cm) and two closed arms (50×10×40 cm). The arms extend from a central platform (10×10 cm) and are raised 50 cm. Each mouse is placed at the center of the maze facing a closed arm and is allowed to explore the maze for 5 min. The time spent in the open arms and the time spent in the closed arms is monitored, and the percent of time spent in the open arms determined. Increased time spent in the open arms indicates an anxiolytic effect for the test condition. A test that measures spontaneous locomotor activity such as measurement in an activity cage can be used to determine whether the test compound also affects locomotor activity. It is desirable that a compound exhibiting an anxiolytic effect not decrease locomotor activity.

Example 191

Animal Model for Assessing Therapeutic Efficacy of Prodrugs of 3-Aminopropylphosphinic Acid Analogs for Treating Epilepsy El Mouse Model The "epilepsy" (El) mouse model to monitor seizure susceptibility after administration of a prodrug of 3-aminopropylphosphinic acid analog (Murashima et al., *Epilepsia* 2002, 43(Suppl. 5), 130-135).

Seizure susceptible El mice are at least 6 months old at the time of testing. Seizure phenotype in response to tail suspension handling during routine husbandry is recorded for each cage of El mice after weaning in order to match treatment groups.

One experimental trial is completed over a 3 day period and three trials are completed over a 7 day period. On day 1 of each trial, all mice are weighed and singly housed in weight matched groups. Each mouse is provided with a pre-weighed food container with a chow or a test compound wet mash ration at the beginning of each 24 h period. On subsequent days, the food containers are removed, weighed and then refilled with fresh food. Mice in a yoked condition are fed the average amount of food consumed by the test compound group over the previous 24 h period. This procedure assures that non-appetitive actions of the test compound are responsible for anticonvulsion efficacy.

On the final day of diet exposure, a seizure susceptibility test is performed in which mice are picked up by their tails and held 10-20 cm above the floor of their home cage for 30 s. Mice are then placed in a clean cage for 2 min and then lifted by the tail for another 15 s before being returned to their home cage. Behavioral characteristics of seizures in El mice are evident during three specific phases: (1) prodromal: squeaking and transient immobility, followed by "running fits;" (2) ictal: convulsions starting with the hind limbs but rapidly becoming generalized tonic-clonic, loss of postural equilibrium, tail cocked over head (Straub tail), salivation, defecation, and urination; and (3) post-ictal: lethargy, "kangaroo posture" (sitting on hind legs with forepaws drawn up), turning of the head in alternate directions, and occasional hyper-irritability. Seizures are determined to have occurred in mice that exhibited behavioral signs such as squeaking, tonic-clonic jerking, cocked tail over the head, loss of posture and post-ictal ataxia. Seizure activity can be quantified using an all-or-none criterion or by scoring seizure severity.

Pilocarpine Epilepsy Model

Young adult male Wistar-2 rats (210-270 kg; 35-42 days) are injected with pilocarpine (340 mg/kg, i.p.) 30 min after injection of methylscopolamine (1 mg/kg, i.p.) (Kudin et al., Eur J Neurosci 2002, 15, 1105-14). Seizure activity begins 20 to 40 min after pilocarpine administration. After 40 min of status epilepticus (SE), the rats are injected with diazepam (DZP; 4 mg/kg, i.p.) or test compound. In the test compound group(s), the SE is terminated after 120 min by DZP (4 mg/kg, i.p.). Control rats receive methylscopolamine, test compound, DZP, or physiologic salt solution instead of pilocarpine.

To determine the seizure frequency, the behavior of the rats is monitored by video (125 h total time). Monitoring begins 14 days after pilocarpine injection using the following protocol. At day 14 after pilocarpine injection, rats are monitored for a total of 5 h, and on the following 12 days, 10 h per day (during the daytime only). Scoring of behavioral seizures is done according to Cavalheiro et al., Epilepsia 1991, 32, 778-82, applying the kindling stages defined by Racine, Electroencephalogr Clin Neurophysiol 1972, 32, 281-94. Referring to this 5-point rating scale, clearly detectable motor seizures (rearing/stage 1V or rearing and falling/stage V) are counted.

Finally, it should be noted that there are alternative ways of implementing the present disclosure. Accordingly, the present embodiments are to be considered as illustrative and not restrictive, and the invention is not to be limited to the details given herein, but may be modified within the scope and equivalents of the claims issuing here from.

What is claimed is:

1. A compound of Formula (I):

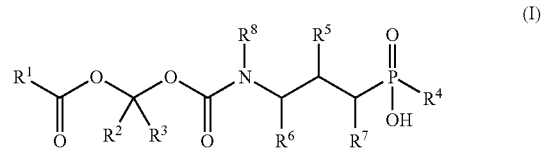

a pharmaceutically acceptable salt thereof, and a pharmaceutically acceptable solvate of any of the foregoing, wherein:

$R^1$ is chosen from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^2$ and $R^3$ is chosen from hydrogen, alkyl, substituted alkyl, alkoxycarbonyl, substituted alkoxycarbonyl, aryl, substituted aryl, arylalkyl, substituted arylalkyl, cycloalkyl, substituted cycloalkyl, heteroaryl, substituted heteroaryl, heteroarylalkyl, and substituted heteroarylalkyl; or $R^2$ and $R^3$ together with the carbon atom to which they are bonded form a cycloalkyl, substituted cycloalkyl, cycloheteroalkyl, or substituted cycloheteroalkyl ring;

$R^4$ is chosen from benzyl, substituted benzyl, $C_{4-7}$ cycloalkyl, $C_{3-7}$ cycloalkylmethyl, and dialkoxymethyl;

$R^5$ is chosen from hydrogen, hydroxy, mercapto, fluoro, oxo, $C_{1-4}$ alkyl, substituted $C_{1-4}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl;

$R^6$ and $R^7$ is chosen from hydrogen, $C_{1-6}$ alkyl, $C_{1-6}$ alkoxy, aryl, substituted aryl, $C_{3-6}$ cycloalkyl, heteroaryl, substituted heteroaryl, $C_{7-9}$ phenylalkyl, and substituted $C_{7-9}$ phenylalkyl; and $R^8$ is chosen from hydrogen, $C_{1-6}$ alkyl, substituted $C_{1-6}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl.

2. The compound of claim 1, wherein $R^1$ is chosen from methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl.

3. The compound of claim 1, wherein $R^1$ is chosen from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl.

4. The compound of claim 1, wherein $R^1$ is chosen from propyl, isopropyl, tert-butyl, cyclohexyl, and phenyl.

5. The compound of claim 1, wherein $R^2$ is chosen from hydrogen, methyl, ethyl, n-propyl, isopropyl, n-butyl, isobutyl, sec-butyl, tert-butyl, phenyl, and cyclohexyl, and $R^3$ is hydrogen.

6. The compound of claim 1, wherein $R^2$ is chosen from hydrogen, methyl, and isopropyl; and $R^3$ is hydrogen.

7. The compound of claim 1, wherein $R^3$ is hydrogen.

8. The compound of claim 1, wherein $R^4$ is chosen from cyclohexyl, cyclopropylmethyl, cyclobutylmethyl, cyclopentylmethyl, cyclohexylmethyl, and cycloheptylmethyl.

9. The compound of claim 1, wherein $R^4$ is chosen from dietihoxylmethyl, cyclohexylmethyl, and benzyl.

10. The compound of claim 1, wherein $R^5$ is chosen from hydrogen, hydroxy, fluoro, oxo, and 4-chlorophenyl.

11. The compound of claim 1, wherein $R^5$ is chosen from hydrogen and hydroxy.

12. The compound of claim 1, wherein each of $R^6$, $R^7$, and $R^8$ is hydrogen.

13. The compound of claim 1, wherein each of $R^6$ and $R^7$ is hydrogen, and $R^8$ is chosen from 3,5-dichlorobenzyl, 1-(3-chlorophenyl)ethyl, 1-(3,4-dichlorophenyl)ethyl, 1-(3-chloro-4-iodophenyl)ethyl, 1-(4-chloro-3-iodophenyl)ethyl, 3,4-dimethylbenzyl, 1-(2,4-dimethoxyphenyl)ethyl, 1-(2,5-dimethoxyphenyl)ethyl, 1-(2,6-dimethoxyphenyl)ethyl, 1-(3,4-dimethoxyphenyl)ethyl, 1-(3,5-dimethoxyphenyl)ethyl, 1-(3,4,5-trimethoxyphenyl)ethyl, 3-carboxybenzyl, 3-cyanobenzyl, 4-carboxybenzyl, 4-cyanobenzyl, 1-(3-carboxyphenyl)ethyl, 1-(3-cyanophenyl)ethyl, 1-(4-carboxyphenyl)ethyl, 1-(4-cyanophenyl)ethyl, 3-phenylprop-2-yl, 2-(3,4-dichlorophenyl)propyl, 3-(3,4-dichlorophenyl)prop-2-yl, and 3-phenyl-3-hydroxyprop-2-yl.

14. The compound of claim 1, wherein each of $R^6$ and $R^7$ is hydrogen, and $R^8$ is chosen from 1-(3,4-dichlorophenyl)ethyl, 1-(3-carboxyphenyl)ethyl, 1-(4-carboxyphenyl)ethyl, 3,5-dichlorobenzyl, 3-carboxybenzyl, and 4-carboxybenzyl.

15. The compound of claim 1, wherein $R^1$ is chosen from propyl, isopropyl, tert-butyl, cyclohexyl, and phenyl; $R^2$ is chosen from hydrogen, methyl, and isopropyl; and each of $R^3$, $R^5$, $R^6$, $R^7$, and $R^8$ is hydrogen.

16. A compound chosen from:
3-{[1-isobutanoyloxyethoxy]carbonylamino}propyl(n-butyl)phosphinic acid;
3-{[benzoyloxyethoxy]carbonylamino}propyl(n-butyl) phosphinic acid;
3-{[1-isobutanoyloxymethoxy]carbonylamino}propyl(n-butyl)phosphinic acid;
3-{[benzoyloxymethoxycarbonylamino}propyl(n-butyl) phosphinic acid;
3-{[1-isobutanoyloxyisobutoxy]carbonylamino}propyl (n-butyl)phosphinic acid;
3-{[1-cyclohexanoyloxyethoxy]carbonylamino}propyl (n-butyl)phosphinic acid;
3-{[1-isobutanoyloxyisobutoxy]carbonylamino}propyl (n-butyl)phosphinic acid sodium salt;
3-{[butanoyloxyethoxy]carbonylamino}propyl(n-butyl) phosphinic acid sodium salt; and a pharmaceutically acceptable solvate of any of the foregoing.

17. A pharmaceutical composition comprising a therapeutically effective amount of at least one pharmaceutically acceptable vehicle and at least one compound of Formula (I):

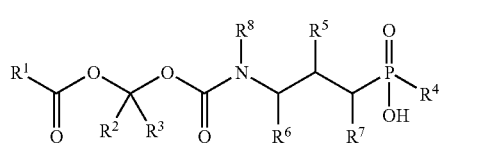

(I)

a pharmaceutically acceptable salt thereof, and a pharmaceutically acceptable solvate of any of the foregoing, wherein:
$R^1$ is chosen from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylailcyl;
$R^2$ and $R^3$ is chosen from hydrogen, alkyl, substituted alkyl, alkoxycarbonyl, substituted alkoxycarbonyl, aryl, substituted aryl, arylalkyl, substituted arylalkyl, cycloalkyl, substituted cycloalkyl, heteroaryl, substituted heteroaryl, heteroarylalkyl, and substituted heteroarylalkyl, or $R^2$ and $R^3$ together with the carbon atom to which they are bonded form a cycloalkyl, substituted cycloalkyl, cycloheteroalkyl, or substituted cycloheteroalkyl ring;
$R^4$ is chosen from benzyl, substituted benzyl, $C_{4-7}$ cycloalkyl, $C_{3-7}$ cycloalkylmethyl, and dialkoxymethyl;
$R^5$ is chosen from hydrogen, hydroxy, mercapto, fluoro, oxo, $C_{1-4}$ alkyl, substituted $C_{1-4}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl;
$R^6$ and $R^7$ is chosen from hydrogen, $C_{1-6}$ alkyl, $C_{1-6}$ alkoxy, aryl, substituted aryl, $C_{3-6}$ cycloalkyl, heteroaryl, substituted heteroaryl, $C_{7-9}$ phenylalkyl, and substituted $C_{7-9}$ phenylalkyl; and
$R^8$ is chosen from hydrogen, $C_{1-6}$ alkyl, substituted $C_{1-6}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl.

18. The pharmaceutical composition of claim 17, wherein the therapeutically effective amount is effective for treating a disease chosen from mild cognitive impairment, cognitive impairment associated with Alzheimer's disease, depression, anxiety, and epilepsy.

19. The pharmaceutical composition of claim 17, wherein the pharmaceutical composition is a sustained release oral formulation.

20. A method of treating a disease chosen from a mild cognitive impairment, cognitive impairment associated with Alzheimer's disease, depression, anxiety, and epilepsy in a patient comprising administering to a patient in need of such treatment the pharmaceutical composition of claim 17.

21. The method of claim 20, wherein a therapeutically effective concentration of the corresponding 3-aminopropylphosphinic acid analog is maintained in the plasma of the patient for at least about 4 hours after the pharmaceutical composition is orally administered to the patient.

22. A pharmaceutical composition comprising a therapeutically effective amount of at least one pharmaceutically acceptable vehicle and at least one compound chosen from:
3-{[1-isobutanoyloxyethoxy]carbonylamino}propyl(n-butyl)phosphinic acid;
3-{[benzoyloxyethoxy]carbonylamino}propyl(n-butyl) phosphinic acid;
3-{[1-isobutanoyloxymethoxy]carbonylamino}propyl(n-butyl)phosphinic acid;
3-{[benzoyloxymethoxycarbonylamino}propyl(n-butyl) phosphinic acid;
3-{[1-isobutanoyloxyisobutoxy]carbonylamino}propyl (n-butyl)phosphinic acid;
3-{[1-cyclohexanoyloxyethoxy]carbonylamino}propyl (n-butyl)phosphinic acid;
3-{[1-isobutanoyloxyisobutoxy]carbonylamino}propyl (n-butyl)phosphinic acid sodium salt;
3-{[butanoyloxyethoxy]carbonylamino}propyl(n-butyl) phosphinic acid sodium salt; and a pharmaceutically acceptable solvate of any of the foregoing.

23. The pharmaceutical composition of claim 17, wherein the therapeutically effective amount is effective for treating a disease chosen from mild cognitive impairment, cognitive impairment associated with Alzheimer's disease, depression, anxiety, and epilepsy.

24. The pharmaceutical composition of claim 22, wherein the pharmaceutical composition is a sustained release oral formulation.

25. A method of treating a disease chosen from a mild cognitive impairment, cognitive impairment associated with Alzheimer's disease, depression, anxiety, and epilepsy in a patient comprising administering to a patient in need of such treatment the pharmaceutical composition of claim 22.

26. The method of claim 25, wherein a therapeutically effective concentration of the corresponding 3-aminopropylphosphinic acid analog is maintained in the plasma of the patient for at least about 4 hours after the pharmaceutical composition is orally administered to the patient.

27. The compound of claim 1, wherein the compound is chosen from:
- 3-{[1-Isobutanoyloxyethoxy]carbonylamino}propyl(cyclohexylmethyl)phosphinic acid;
- 3-{[1-Butanoyloxyethoxylcarbonylamino}propyl(cyclohexylmethyl)phosphinic acid;
- 3-{[1-Pivaloyloxyethoxy]carbonylamino}propyl(cyclohexylmethyl)phosphinic acid;
- 3-{[1-Cyclohexanoyloxyethoxy]carbonylamino}propyl(cyclohexylmethyl)phosphinic acid;
- 3-{[Isobutanoyloxymethoxy]carbonylamino}propyl(cyclohexylmethyl)phosphinic acid;
- 3-{[Butanoyloxymethoxy]carbonylamino}propyl(cyclohexylmethyl)phosphinic acid;
- 3-{[Pivaloyloxymethoxy]carbonylamino}propyl(cyclohexylmethyl)phosphinic acid;
- 3-{[Cyclohexanoyloxymethoxy]carbonylamino}propyl(cyclohexylmethyl)phosphinic acid;
- 3-{[(1R)-Isobutanoyloxyisobutoxy]carbonylamino}propyl(cyclohexylmethyl)phosphinic acid;
- 3-{[(1S)-Isobutanoyloxyisobutoxy]carbonylamino}propyl(cyclohexylmethyl)phosphinic acid;
- 3-{[1-Isobutanoyloxyethoxy]carbonylamino}-(2R)-hydroxypropyl(cyclohexylmethyl)phosphinic acid;
- 3-{[1-Butanoyloxyethoxy]carbonylamino}-(2R)-hydroxypropyl(cyclohexylmethyl)phosphinic acid;
- 3-{[1-Pivaloyloxyethoxy]carbonylamino}-(2R)-hydroxypropyl(cyclohexyhnethyl)phosphinic acid;
- 3-{[1-Cyclohexanoyloxyethoxy]carbonylamino}-(2R)-hydroxypropyl(cyclohexylmethyl)phosphinic acid;
- 3-{[Isobutanoyloxymethoxyllcarbonylamino}-(2R)-hydroxypropyl(cyclohexylmethyl)phosphinic acid;
- 3-{[Butanoyloxymethoxy]carbonylamino}-(2R)-hydroxypropyl(cyclohexylmethyl)phosphinic acid;
- 3-{[Pivaloyloxymethoxy]carbonylamino}-(2R)-hydroxypropyl(cyclohexylmethyl)phosphinic acid;
- 3-{[Cyclohexanoyloxymethoxy]carbonylamino}-(2R)-hydroxypropyl(cyclohexylmethyl)phosphinic acid;
- 3-{[(1R)-Isobutanoyloxyisobutoxy]carbonylamino}-(2R)-hydroxypropyl(cyclohexylmethyl)phosphinic acid;
- 3-{[(1S)-Isobutanoyloxyisobutoxy]carbonylamino}-(2R)-hydroxypropyl(cyclohexylmethyl)phosphinic acid;
- 3-{[1-Isobutanoyloxyothoxy]carbonylamino}-(2S)-hydroxypropyl(cyclohexylmethyl)phosphinic acid;
- 3-{[1-Butanoyloxyethoxy]carbonylamino}-(2S)-hydroxypropyl(cyclohexylmethyl)phosphinic acid;
- 3-{[1-Pivaloyloxyethoxy]carbonylamino}-(2S)-hydroxypropyl(cyclohexylmethyl)phosphinic acid;
- 3-{[1-Cyclohexanoyloxyethoxy]carbonylamino}-(2S)-hydroxypropyl(cyclohexylmethyl)phosphinic acid;
- 3-{[Isobutanoyloxymethoxy]carbonylamino}-(2S)-hydroxypropyl(cyclohexylmethyl)phosphinic acid;
- 3-{[Butanoyloxymethoxy]carbonylamino}-(2S)-hydroxypropyl(cyclohexylmethyl)phosphinic acid;
- 3-{[Pivaloyloxymethoxy]carbonylamino}-(2S)-hydroxypropyl(cyclohexylmethyl)phosphinic acid;
- 3-{[Cyclohexanoyloxymethoxy]carbonylamino}-(2S)-hydroxypropyl(cyclohexylmethyl)phosphinic acid;
- 3-{[(1R)-Isobutanoyloxyisobutoxy]carbonylamino}-(2S)-hydroxypropyl(cyclohexylmethyl)phosphinic acid;
- 3-{[(1S)-Isobutanoyloxyisobutoxy]carbonylamino}-(2S)-hydroxypropyl(cyclohexylmethyl)phosphinic acid;
- 3-{[1-Isobutanoyloxyethoxy]carbonylamino}-(2S)-fluoropropyl(cyclohexylmethyl)phosphinic acid;
- 3-{[1-Butanoyloxyethoxy]carbonylamino}-(2R)-fluoropropyl(cyclohexylmethyl)phosphinic acid;
- 3-{[1-Pivaloyloxyethoxy]carbonylamino}-(2R)-fluoropropyl(cyclohexylmethyl)phosphinic acid;
- 3-{[1-Cyclohexanoyloxyethoxy]carbonylamino}-(2R)-fluoropropyl(cyclohexylmethyl)phosphinic acid;
- 3-{[Isobutanoyloxymethoxy]carbonylamino}-(2R)-fluoropropyl(cyclohexylmethyl)phosphinic acid;
- 3-{[Butanoyloxymethoxy]carbonylamino}-(2R)-fluoropropyl(cyclohexylmethyl)phosphinic acid;
- 3-{[Pivaloyloxymethoxy]carbonylamino}-(2R)-fluoropropyl(cyclohexylmethyl)phosphinic acid;
- 3-{[Cyclohexanoyloxymethoxy]carboflylamino}-(2R)-fluoropropyl(cyclohexylmethyl)phosphinic acid;
- 3-{[(1R)-Isobutanoyloxyisobutoxy]carbonylamino}-(2R)-fluoropropyl(cyclohexylmethyl)phosphinic acid;
- 3-{[(1S)-Isobutanoyloxyisobutoxy]carbonylamino}-(2R)-fluoropropyl(cyclohexylmethyl)phosphinic acid;
- 3-{[1-Butanoyloxyethoxy]carbonylamino}-(2S)-fluoropropyl(cyclohexylmethyl)phosphinic acid;
- 3-{[1-Pivaloyloxyethoxy]carbonylamino}-(2S)-fluoropropyl(cyclohexylmethyl)phosphinic acid;
- 3-{[1-Cyclohexanoyloxyethoxy]carbonylamino}-(2S)-fluoropropyl(cyclohexylmethyl)phosphinic acid;
- 3-{[Isobutanoyloxymethoxy]carbonylamino}-(2S)-fluoropropyl(cyclohexylmethyl)phosphinic acid;
- 3-{[Butanoyloxymethoxy]carbonylamino}-(2S)-fluoropropyl(cyclohexylmethyl)phosphinic acid;
- 3-{[Pivaloyloxymethoxy]carbonylamino}-(2S)-fluoropropyl(cyclohexylmethyl)phosphinic acid;
- 3-{[(1R)-Isobutanoyloxyisobutoxy]carbonylamino}-(2S)-fluoropropyl(cyclohexylmethyl)phosphinic acid;
- 3-{[(1S)-Isobutanoyloxyisobutoxy]carbonylamino}-(2S)-fluoropropyl(cyclohexylmethyl)phosphinic acid;
- 3-{[1-Isobutanoyloxyethoxy]carbonylamino}-2-oxopropyl(cyclohexylmethyl)phosphinic acid;
- 3-{[1-Butanoyloxyethoxy]carbonylamino}-2-oxopropyl(cyclohexylmethyl)phosphinic acid;
- 3-{[1-Pivaloyloxyethoxy]carbonylamino}-2-oxopropyl(cyclohexyhnethyl)phosphinic acid;
- 3-{[1-Cyclohexanoyloxyethoxy]carbonylamino}-2-oxopropyl(cyclohexylmethyl)phosphinic acid;
- 3-{[Isobutanoyloxymethoxy]carbonylamino}-2-oxopropyl(cyclohexylmethyl)phosphinic acid;
- 3-{[Butanoyloxymethoxy]carbonylamino}-2-oxopropyl(cyclohexylmethyl)phosphinic acid;
- 3-{[Pivaloyloxymethoxy)carbonylamino}-2-oxopropyl(cyclohexylmethyl)phosphinic acid;

3-{[Cyclohexanoyloxymethoxy]carbonylamino}-2-oxo-propyl(cyclohexylmethyl)phosphinic acid;

3-{[(1R)-Isobutanoyloxyisobutoxy]carbonylamino}-2-oxopropyl(cyclohexylmethyl)phosphinic acid;

3-{[(1S)-Isobutanoyloxyisobutoxy]carbonylamino}-2-oxopropyl(cyclohexylmethyl)phosphinic acid;

3-{N-(1'-Isobutanoyloxyethoxy)carbonyl-N-[1(R)-(3,4-dichlorophenyl)ethyl]amino}propyl(cyclohexylmethyl)phosphinic acid;

3-{N-(1'-Butanoyloxyethoxy)carbonyl-N-[1(R)-(3,4-dichlorophenyl)ethyl]amino}propyl(cyclohexylmethyl)phosphinic acid;

3-{N-(1'-Pivaloyloxyethoxy)carbonyl-N-[1(R)-(3,4-dichlorophenyl)ethyl]amino}propyl(cyclohexylmethyl)phosphinic acid;

3-{N-(1'-Cyclohexanoyloxyethoxy)carbonyl-N-[1(R)-(3,4-dichlorophenyl)ethyl]amino}propyl(cyclohexylmethyl)phosphinic acid;

3-{N-(Isobutanoyloxymethoxy]carbonyl-N-[1(R)-(3,4-dichlorophenyl)ethyl]amino}propyl(cyclohexylmethyl)phosphinic acid;

3-{N-(Butanoyloxymethoxy)carbonyl-N-[1(R)-(3,4-dichlorophenyl)ethyl]amino}propyl(cyclohexylmethyl)phosphinic acid;

3-{N-(Pivaloyloxymethoxy)carbonyl-N-[1(R)-(3,4-dichlorophenyl)ethyl]amino}propyl(cyclohexylmethyl)phosphinic acid;

3-{N-(Cyclohexanoyloxymethoxy)carbonyl-N-[1(R)-(3,4-dichlorophenyl)ethyl]amino}propyl(cyclohexylmethyl)phosphinic acid;

3-{N-((1'R)-Isobutanoyloxyisobutoxy)carbonyl-N-[1(R)-(3,4-dichlorophenyl)ethyl]amino}propyl(cyclohexylmethyl)phosphinic acid;

3-{N-((1'S)-Isobutanoyloxyisobutoxy)carbonyl-N-[1(R)-(3,4-dichlorophenyl)ethyl]amino}propyl(cyclohexylmethyl)phosphinic acid;

3-{N-(1'-Isobutanoyloxyethoxy)carbonyl-N-[1(R)-(3,4-dichlorophenyl)ethyl]amino}-(2R)-hydroxypropyl(cyclohexylmethyl)phosphinic acid;

3-{N-(1'-Butanoyloxyethoxy)carbonyl-N-[1(R)-(3,4-dichlorophenyl)ethyl]amino}-(2R)-hydroxypropyl(cyclohexylmethyl)phosphinic acid;

3-{N-(1'-Pivaloyloxyethoxy)carbonyl-N-[1(R)-(3,4-dichlorophenyl)ethyl]amino}-(2R)-hydroxypropyl(cyclohexylmethyl)phosphinic acid;

3-{N-(1'-Cyclohexanoyloxyethoxy)carbonyl-N-[1(R)-(3,4-dichlorophenyl)ethyl]amino}-(2R)-hydroxypropyl(cyclohexylmethyl)phosphinic acid;

3-{N-(Isobutanoyloxymethoxy]carbonyl-N-[1(R)-(3,4-dichlorophenyl)ethyl]amino}-(2R)-hydroxypropyl(cyclohexylmethyl)phosphinic acid;

3-{N-(Butanoyloxymethoxy)carbonyl-N-[1(R)-(3,4-dichlorophenyl)ethyl]amino}-(2R)-hydroxypropyl(cyclohexylmethyl)phosphinic acid;

3-{N-(Pivaloyloxymethoxy)carbonyl-N-[1(R)-(3,4-dichlorophenyl)ethyl]amino}-(2R)-hydroxypropyl(cyclohexylmethyl)phosphinic acid;

3-{N-(Cyclohexanoyloxymethoxy)carbonyl-N-[1(R)-(3,4-dichlorophenyl)ethyl]amino}-(2R)-hydroxypropyl(cyclohexylmethyl)phosphinic acid;

3-{N-((1'R)-Isobutanoyloxyisobutoxy)carbonyl-N-[1(R)-(3,4-dichlorophenyl)ethyl]amino}-(2R)-hydroxypropyl(cyclohexylmethyl)phosphinic acid;

3-{N-((1'S)-Isobutanoyloxyisobutoxy)carbonyl-N-[1(R)-(3,4-dichlorophenyl)ethyl]amino}-(2R)-hydroxypropyl(cyclohexylmethyl)phosphinic acid;

3-{N-(1'-Isobutanoyloxyethoxy)carbonyl-N-[1(R)-(3,4-dichlorophenyl)ethyl]amino}-(2S)-hydroxypropyl(cyclohexylmethyl)phosphinic acid;

3-{N-(1'-Butanoyloxyethoxy)carbonyl-N-[1(R)-(3,4-dichlorophenyl)ethyl]amino}-(2S)-hydroxypropyl(cyclohexylmethyl)phosphinic acid;

3-{N-(1'-Pivaloyloxyethoxy)carbonyl-N-[1(R)-(3,4-dichlorophenyl)ethyl]amino}-(2S)-hydroxypropyl(cyclohexylmethyl)phosphinic acid;

3-{N-(1'-Cyclohexanoyloxyethoxy)carbonyl-N-[1(R)-(3,4-dichlorophenyl)ethyl]amino}-(2S)-hydroxypropyl(cyclohexylmethyl)phosphinic acid;

3-{N-(Isobutanoyloxymethoxy]carbonyl-N-[1(R)-(3,4-dichlorophenyl)ethyl]amino}-(2S)-hydroxypropyl(cyclohexylmethyl)phosphinic acid;

3-{N-(Butanoyloxymethoxy)carbonyl-N-[1(R)-(3,4-dichlorophenyl)ethyl]amino}-(2S)-hydroxypropyl(cyclohexylmethyl)phosphinic acid;

3-{N-(Pivaloyloxymethoxy)carbonyl-N-[1(R)-(3,4-dichlorophenyl)ethyl]amino}-(2S)-hydroxypropyl(cyclohexylmethyl)phosphinic acid;

3-{N-(Cyclohexanoyloxymethoxy)carbonyl-N-[1(R)-(3,4-dichlorophenyl)ethyl]amino}-(2S)-hydroxypropyl(cyclohexylmethyl)phosphinic acid;

3-{N-((1'R)-Isobutanoyloxyisobutoxy)carbonyl-N-[1(R)-(3,4-dichlorophenyl)ethyl]amino}-(2S)-hydroxypropyl(cyclohexylmethyl)phosphinic acid;

3-{N-((1'S)-Isobutanoyloxyisobutoxy)carbonyl-N-[1(R)-(3,4-dichlorophenyl)ethyl]amino}-(2S)-hydroxypropyl(cyclohexylmethyl)phosphinic acid;

3-{N-(1'-Isobutanoyloxyethoxy)carbonyl-N-[1(S)-(3,4-dichlorophenyl)ethyl]amino}propyl(cyclohexylmethyl)phosphinic acid;

3-{N-(1'-Butanoyloxyethoxy)carbonyl-N-[1(S)-(3,4-dichlorophenyl)ethyl]amino}propyl(cyclohexylmethyl)phosphinic acid;

3-{N-(1'-Pivaloyloxyethoxy)carbonyl-N-[1(S)-(3,4-dichlorophenyl)ethyl]amino}propyl(cyclohexylmethyl)phosphinic acid;

3-{N-(1'-Cyclohexanoyloxyethoxy)carbonyl-N-[1(S)-(3,4-dichlorophenyl)ethyl]amino}propyl(cyclohexylmethyl)phosphinic acid;

3-{N-(Isobutanoyloxymethoxy]carbonyl-N-[1(S)-(3,4-dichlorophenyl)ethyl]amino}propyl(cyclohexylmethyl)phosphinic acid;

3-{N-(Butanoyloxymethoxy)carbonyl-N-[1(S)-(3,4-dichlorophenyl)ethyl]amino}propyl(cyclohexylmethyl)phosphinic acid;

3-{N-(Pivaloyloxymethoxy)carbonyl-N-[1(S)-(3,4-dichlorophenyl)ethyl]arnino}propyl(cyclohexylmethyl)phosphinic acid;

3-{N-(Cyclohexanoyloxymethoxy)carbonyl-N-[1(S)-(3,4-dichlorophenyl)ethyl]amino}propyl(cyclohexylmethyl)phosphinic acid;

3-{N-((1'R)-Isobutanoyloxyisobutoxy)carbonyl-N-[1(S)-(3,4-dichlorophenyl)ethyl]amino}propyl(cyclohexylmethyl)phosphinic acid;

3-{N-((1'S)-Isobutanoyloxyisobutoxy)carbonyl-N-[1(S)-(3,4-dichlorophenyl)ethyl]amino}propyl(cyclohexylmethyl)phosphinic acid;

3-{N-(1'-Isobutanoyloxyethoxy)carbonyl-N-[1(S)-(3,4-dichlorophenyl)ethyl]amino}-(2R)-hydroxypropyl(cyclohexylmethyl)phosphinic acid;

3-{N-(1'-Butanoyloxyethoxy)carbonyl-N-[1(S)-(3,4-dichlorophenyl)ethyl]amino}-(2R)-hydroxypropyl(cyclohexylmethyl)phosphinic acid;

3-{N-(1'-Pivaloyloxyethoxy)carbonyl-N-[1(S)-(3,4-dichlorophenyl)ethyl]amino}-(2R)-hydroxypropyl(cyclohexylmethyl)phosphinic acid;

3-{N-(1'-Cyclohexanoyloxyethoxy)carbonyl-N-[1(S)-(3,4-dichlorophenyl)ethyl]amino}-(2R)-hydroxypropyl(cyclohexylmethyl)phosphinic acid;

3-{N-(Isobutanoyloxymethoxy]carbonyl-N-[1(S)-(3,4-dichlorophenyl)ethyl]amino}-(2R)-hydroxypropyl(cyclohexyhnethyl)phosphinic acid;

3-{N-(Butanoyloxymethoxy)carbonyl-N-[1(S)-(3,4-dichlorophenyl)ethyl]amino}-(2R)-hydroxypropyl(cyclohexylmethyl)phosphinic acid;

3-{N-(Pivaloyloxymethoxy)carbonyl-N-[1(S)-(3,4-dichlorophenyl)ethyl]amino}-(2R)-hydroxypropyl(cyclohexylmethyl)phosphinic acid;

3-{N-(Cyclohexanoyloxymethoxy)carbonyl-N-[1(S)-(3,4-dichlorophenyl)ethyl]amino}-(2R)-hydroxypropyl(cyclohexylmethyl)phosphinic acid;

3-{N-((1'R)-Isobutanoyloxyisobutoxy)carbonyl-N-[1(S)-(3,4-dichlorophenyl)ethyl]amino}-(2R)-hydroxypropyl(cyclohexylmethyl)phosphinic acid;

3-{N-((1'S)-Isobutanoyloxyisobutoxy)carbonyl-N-[1(S)-(3,4-dichlorophenyl)ethyl]amino}-(2R)-hydroxypropyl(cyclohexylmethyl)phosphinic acid;

3-{N-(1'-Isobutanoyloxyethoxy)carbonyl-N-[1(S)-(3,4-dichlorophenyl)ethyl]amino}-(2S)-hydroxypropyl(cyclohexylmethyl)phosphinic acid;

3-{N-(1'-Butanoyloxyethoxy)carbonyl-N-[1(S)-(3,4-dichlorophenyl)ethyl]amino}-(2S)-hydroxypropyl(cyclohexylmethyl)phosphinic acid;

3-{N-(1'-Pivaloyloxyethoxy)carbonyl-N-[1(S)-(3,4-dichlorophenyl)ethyl]amino}-(2S)-hydroxypropyl(cyclohexylmethyl)phosphinic acid;

3-{N-(1'-Cyclohexanoyloxyethoxy)carbonyl-N-[1(S)-(3,4-dichlorophenyl)ethyl]amino}-(2S)-hydroxypropyl(cyclohexylmethyl)phosphinic acid;

3-{N-(Isobutanoyloxymethoxy]carbonyl-N-[1(S)-(3,4-dichlorophenyl)ethyl]amino}-(2S)-hydroxypropyl(cyclohexylmethyl)phosphinic acid;

3-{N-(Butanoyloxymethoxy)carbonyl-N-[1(S)-(3,4-dichlorophenyl)ethyl]amino}-(2S)-hydroxypropyl(cyclohexylmethyl)phosphinic acid;

3-{N-(Pivaloyloxymethoxy)carbonyl-N-[1(S)-(3,4-dichlorophenyl)ethyl]amino}-(2S)-hydroxypropyl(cyclohexylmethyl)phosphinic acid;

3-{N-(Cyclohexanoyloxymethoxy)carbonyl-N-[1(S)-(3,4-dichlorophenyl)ethyl]amino}-(2S)-hydroxypropyl(cyclohexylmethyl)phosphinic acid;

3-{N-((1'R)-Isobutanoyloxyisobutoxy)carbonyl-N-[1(S)-(3,4-dichlorophenyl)ethyl]amino}-(2S)-hydroxypropyl(cyclohexylmethyl)phosphinic acid;

3-{N-((1'S)-Isobutanoyloxyisobutoxy)carbonyl-N-[1(S)-(3,4-dichlorophenyl)ethyl]amino}-(2S)-hydroxypropyl(cyclohexylmethyl)phosphinic acid;

a pharmaceutically acceptable salt thereof, and a pharmaceutically acceptable solvate of any of the foregoing.

\* \* \* \* \*

UNITED STATES PATENT AND TRADEMARK OFFICE
CERTIFICATE OF CORRECTION

PATENT NO. : 7,585,996 B2
APPLICATION NO. : 11/901194
DATED : September 8, 2009
INVENTOR(S) : Gallop et al.

It is certified that error appears in the above-identified patent and that said Letters Patent is hereby corrected as shown below:

Claim 17, col. 334, line 2, "heteroarylailcyl" should read --heteroarylalkyl--.

Claim 27, col. 336, line 32, "carboflylamino" should read --carbonylamino--.

Claim 27, col. 337, lines 32-33, "cyciohexylmethyl" should read --cyclohexylmethyl--.

Claim 27, col. 339, lines 8-9, "cyclohexyhnethyl" should read --cyclohexylmethyl--.

Signed and Sealed this

Twenty-second Day of December, 2009

David J. Kappos
*Director of the United States Patent and Trademark Office*